United States Patent
Kubota et al.

(10) Patent No.: US 7,098,013 B2
(45) Date of Patent: Aug. 29, 2006

(54) POLYPEPTIDE HAVING α-ISOMALTOSYL-TRANSFERASE ACTIVITY

(75) Inventors: Michio Kubota, Okayama (JP); Kazuhiko Maruta, Okayama (JP); Takuo Yamamoto, Okayama (JP); Shigeharu Fukuda, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 647 days.

(21) Appl. No.: 10/181,183

(22) PCT Filed: Nov. 16, 2001

(86) PCT No.: PCT/JP01/10044

§ 371 (c)(1), (2), (4) Date: Jul. 15, 2002

(87) PCT Pub. No.: WO02/40659

PCT Pub. Date: May 23, 2002

(65) Prior Publication Data

US 2004/0121431 A1    Jun. 24, 2004

(30) Foreign Application Priority Data

Nov. 16, 2000  (JP)  .............. 2000-350142

(51) Int. Cl.
- *C12N 9/10*  (2006.01)
- *C12N 5/00*  (2006.01)
- *C12N 15/00*  (2006.01)
- *C12N 1/20*  (2006.01)
- *C12N 1/14*  (2006.01)
- *C12N 1/16*  (2006.01)
- *C12P 19/04*  (2006.01)
- *C12P 21/06*  (2006.01)
- *C07H 21/04*  (2006.01)

(52) U.S. Cl. ................ 435/193; 435/325; 435/252.31; 435/69.1; 435/252.33; 435/41; 435/252.2; 435/320.1; 435/254.2; 536/23.2

(58) Field of Classification Search .................. None
See application file for complete search history.

(56) References Cited

U.S. PATENT DOCUMENTS

| | | |
|---|---|---|
| 5,786,196 A | 7/1998 | Cote et al. |
| 5,888,776 A | 3/1999 | Cote et al. |
| 5,889,179 A | 3/1999 | Cote et al. |

FOREIGN PATENT DOCUMENTS

| | | |
|---|---|---|
| EP | 0606753 A2 | 7/1994 |
| EP | 0628630 A2 | 12/1994 |
| EP | 1 229 112 A | 8/2002 |
| JP | 23799/83 A | 2/1983 |
| JP | 72598/83 A | 4/1983 |
| JP | 213283/95 A | 8/1985 |
| JP | 143876/95 A | 6/1995 |
| WO | WO-02/10361 A1 | 8/2000 |
| WO | WO-01/90338 A1 | 11/2001 |

OTHER PUBLICATIONS

M. Abdullah and W. J. Whelan Biochemical Journal, (1960) 75, p. 12.*
Dexter French et al "Studies on the Schardinger Dextrins. The Preparation and Solubility Characteristics of Alpha, Beta and Gamma Dextrins" Journal of American Chemica Society, Jan. 1949, vol. 71, pp. 353-358.
Gregory L. Cote et al "Enzymically produced cyclic α-1, 3-linked and α-1, 6-linked oligosaccharides of D-glucose", European Journal of Biochemistry, 1994, vol. 226, pp. 641-648.
U.K. Laemmli "Cleavage of Structural Proteins during the Assembly of the Head of Bacteriophage T4" Laemmli in Nature, 1970, vol. 227, pp. 680-685.
H.A. Wyckoff et al Isolation and Characterization of Microorganisms with Alternan Hydrolytic Activity, Current Microbiology, 1996, vol. 32, No. 6, pp. 343-348.

* cited by examiner

*Primary Examiner*—Rebecca E. Prouty
*Assistant Examiner*—Mohammad Meah
(74) *Attorney, Agent, or Firm*—Browdy and Neimark, PLLC

(57) ABSTRACT

The object of the present invention is to provide a polypeptide which can be used to produce a saccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→}, a DNA encoding the polypeptide, and uses thereof. The present invention solves the above object by establishing a polypeptide which has an enzymatic activity to produce a saccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide with a glucose polymerization degree of 3 or higher and bearing both the α-1,6 glucosidic linkage as a linkage at the non-reducing end and the α-1,4 glucosidic linkage other than the linkage at the non-reducing end by catalyzing the α-isomaltosyl-transfer, and having an amino acid sequence of either SEQ ID NO:1 or SEQ ID NO:2, or that which is a member selected from the group consisting of amino acid sequences having deletion, replacement, or addition of one or more amino acid residues therein or thereto, a DNA encoding the polypeptide, and uses thereof.

9 Claims, 5 Drawing Sheets

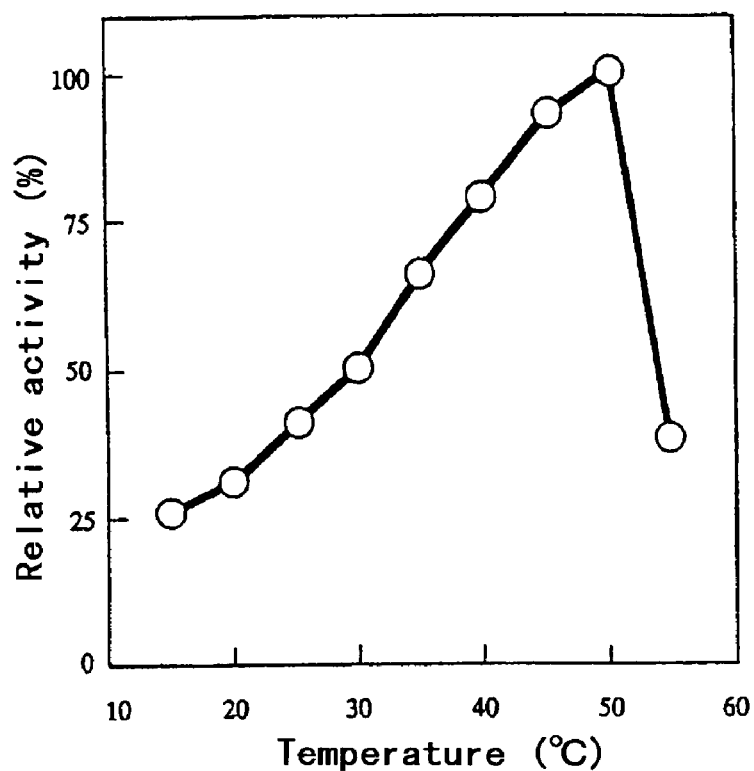
F I G. 1
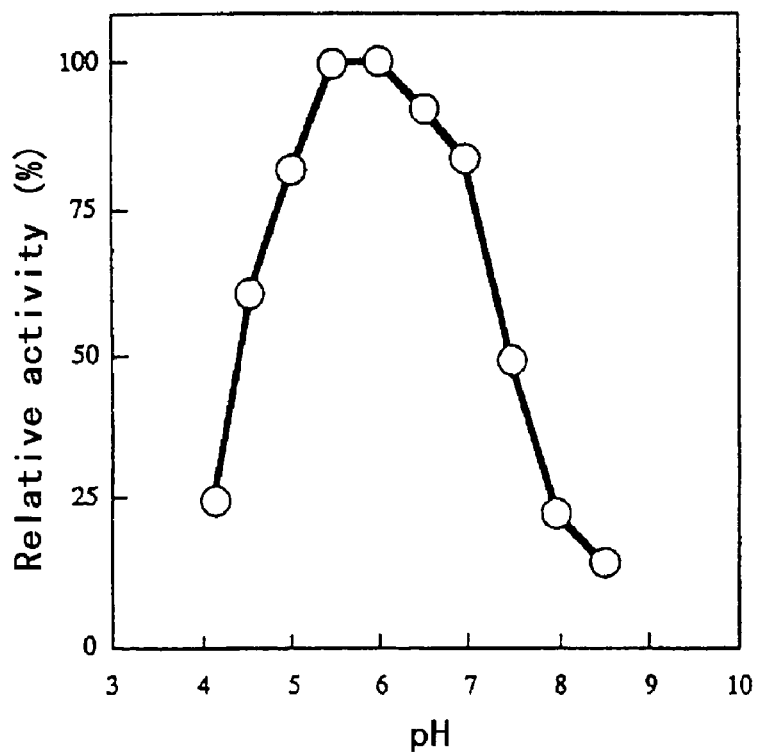
F I G. 2

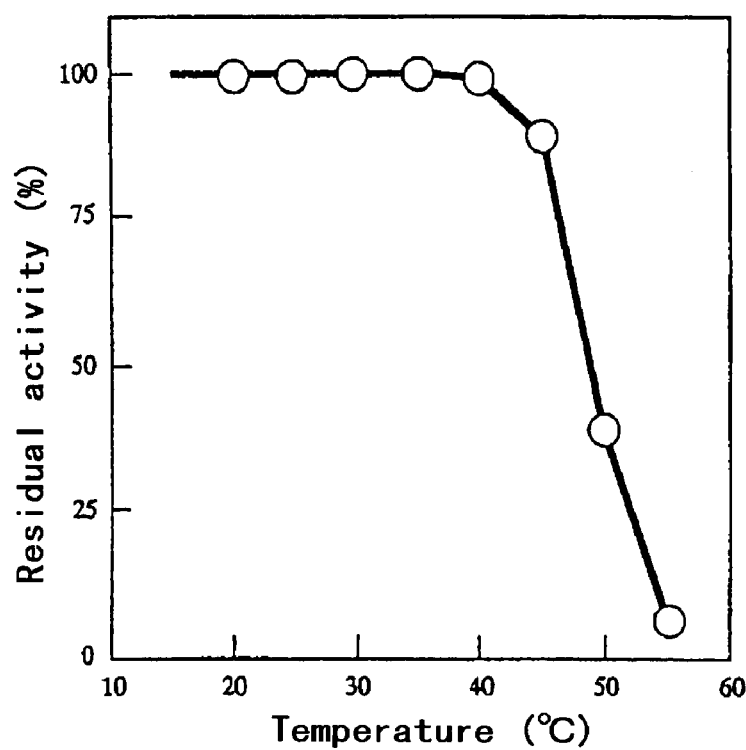
F I G. 3
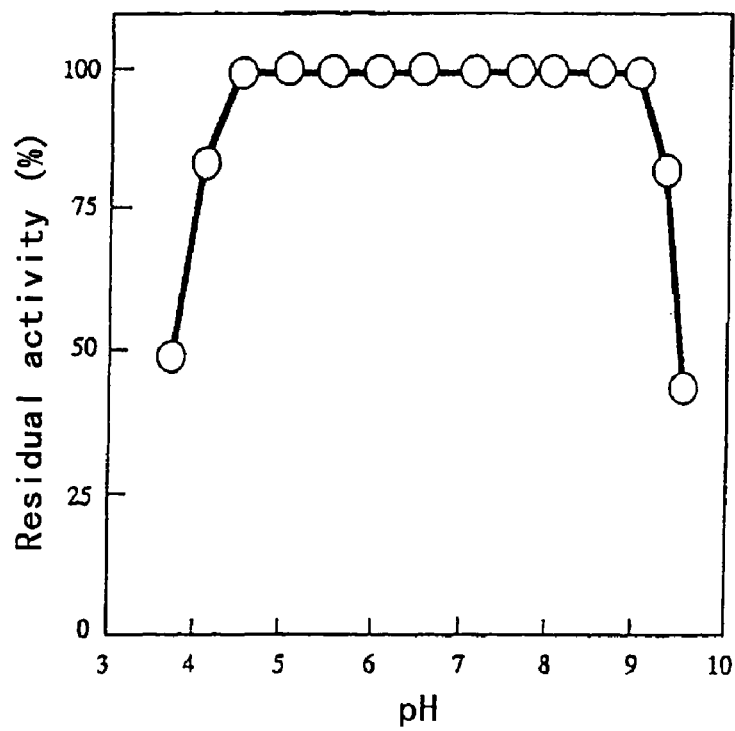
F I G. 4

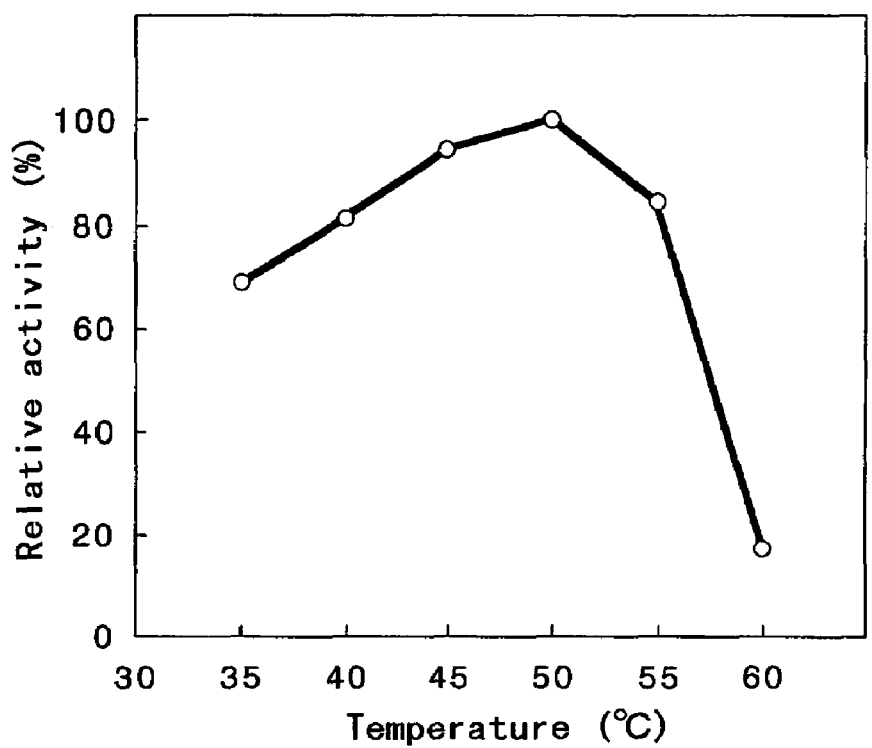
F I G. 5
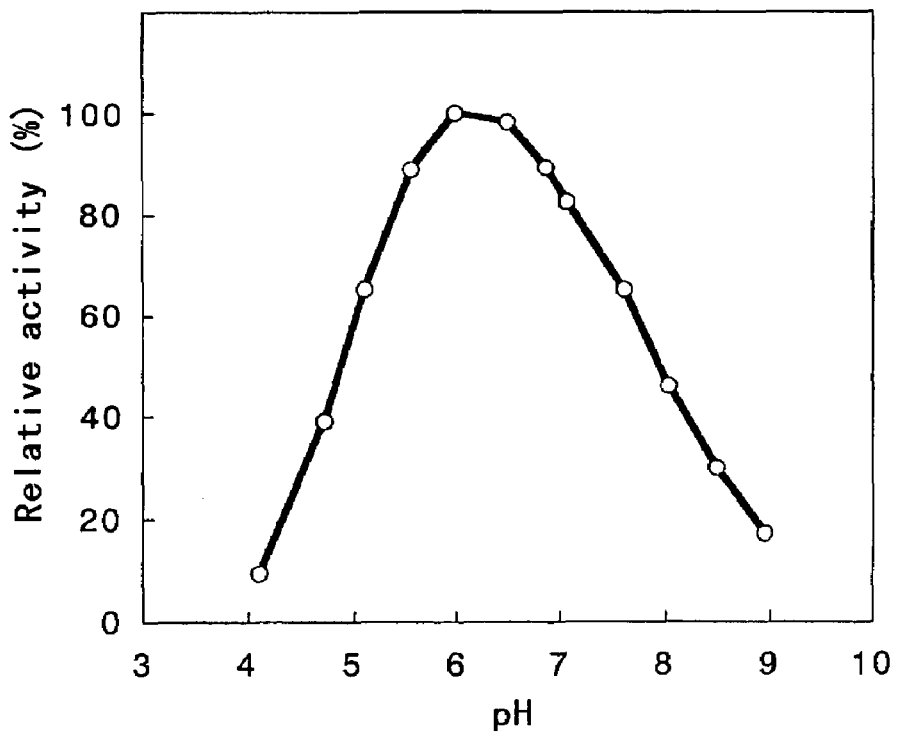
F I G. 6

SEQUENCE LISTING

```
<160> NUMBER OF SEQ ID NOS: 19

<210> SEQ ID NO 1
<211> LENGTH: 1064
<212> TYPE: PRT
<213> ORGANISM: Bacillus globisporus

<400> SEQUENCE: 1

Ile Asp Gly Val Tyr His Ala Pro Tyr Gly Ile Asp Asp Leu Tyr Glu
1               5                   10                  15

Ile Gln Ala Thr Glu Arg Ser Pro Arg Asp Pro Val Ala Gly Asp Thr
            20                  25                  30

Val Tyr Ile Lys Ile Thr Thr Trp Pro Ile Glu Ser Gly Gln Thr Ala
        35                  40                  45

Trp Val Thr Trp Thr Lys Asn Gly Val Asn Gln Ala Ala Val Gly Ala
    50                  55                  60

Ala Phe Lys Tyr Asn Ser Gly Asn Asn Thr Tyr Trp Glu Ala Asn Leu
65                  70                  75                  80

Gly Thr Phe Ala Lys Gly Asp Val Ile Ser Tyr Thr Val His Gly Asn
                85                  90                  95

Lys Asp Gly Ala Asn Glu Lys Val Ile Gly Pro Phe Thr Phe Thr Val
            100                 105                 110

Thr Gly Trp Glu Ser Val Ser Ser Ile Ser Ser Ile Thr Asp Asn Thr
        115                 120                 125

Asn Arg Val Val Leu Asn Ala Val Pro Asn Thr Gly Thr Leu Lys Pro
    130                 135                 140

Lys Ile Asn Leu Ser Phe Thr Ala Asp Asp Val Leu Arg Val Gln Val
```

-continued

```
145                 150                 155                 160
Ser Pro Thr Gly Thr Gly Thr Leu Ser Ser Gly Leu Ser Asn Tyr Thr
                165                 170                 175
Val Ser Asp Thr Ala Ser Thr Thr Trp Leu Thr Thr Ser Lys Leu Lys
            180                 185                 190
Val Lys Val Asp Lys Asn Pro Phe Lys Leu Ser Val Tyr Lys Pro Asp
        195                 200                 205
Gly Thr Thr Leu Ile Ala Arg Gln Tyr Asp Ser Thr Thr Asn Arg Asn
    210                 215                 220
Ile Ala Trp Leu Thr Asn Gly Ser Thr Ile Ile Asp Lys Val Glu Asp
225                 230                 235                 240
His Phe Tyr Ser Pro Ala Ser Glu Glu Phe Gly Phe Gly Glu His
                245                 250                 255
Tyr Asn Asn Phe Arg Lys Arg Gly Asn Asp Val Asp Thr Tyr Val Phe
                260                 265                 270
Asn Gln Tyr Lys Asn Gln Asn Asp Arg Thr Tyr Met Ala Ile Pro Phe
            275                 280                 285
Met Leu Asn Ser Ser Gly Tyr Gly Ile Phe Val Asn Ser Thr Tyr Tyr
        290                 295                 300
Ser Lys Phe Arg Leu Ala Thr Glu Arg Thr Asp Met Phe Ser Phe Thr
305                 310                 315                 320
Ala Asp Thr Gly Gly Ser Ala Ala Ser Met Leu Asp Tyr Tyr Phe Ile
                325                 330                 335
Tyr Gly Asn Asp Leu Lys Asn Val Val Ser Asn Tyr Ala Asn Ile Thr
            340                 345                 350
Gly Lys Pro Thr Ala Leu Pro Lys Trp Ala Phe Gly Leu Trp Met Ser
        355                 360                 365
Ala Asn Glu Trp Asp Arg Gln Thr Lys Val Asn Thr Ala Ile Asn Asn
    370                 375                 380
Ala Asn Ser Asn Asn Ile Pro Ala Thr Ala Val Val Leu Glu Gln Trp
385                 390                 395                 400
Ser Asp Glu Asn Thr Phe Tyr Ile Phe Asn Asp Ala Thr Tyr Thr Pro
                405                 410                 415
Lys Thr Gly Ser Ala Ala His Ala Tyr Thr Asp Phe Thr Phe Pro Thr
            420                 425                 430
Ser Gly Arg Trp Thr Asp Pro Lys Ala Met Ala Asp Asn Val His Asn
        435                 440                 445
Asn Gly Met Lys Leu Val Leu Trp Gln Val Pro Ile Gln Lys Trp Thr
    450                 455                 460
Ser Thr Pro Tyr Thr Gln Lys Asp Asn Asp Glu Ala Tyr Met Thr Ala
465                 470                 475                 480
Gln Asn Tyr Ala Val Gly Asn Gly Ser Gly Gln Tyr Arg Ile Pro
                485                 490                 495
Ser Gly Gln Trp Phe Glu Asn Ser Leu Leu Asp Phe Thr Asn Thr
            500                 505                 510
Ala Ala Lys Asn Trp Trp Met Ser Lys Arg Ala Tyr Leu Phe Asp Gly
        515                 520                 525
Val Gly Ile Asp Gly Phe Lys Thr Asp Gly Gly Glu Met Val Trp Gly
    530                 535                 540
Arg Ser Asn Thr Phe Ser Asn Gly Lys Lys Gly Asn Glu Met Arg Asn
545                 550                 555                 560
Gln Tyr Pro Asn Glu Tyr Val Lys Ala Tyr Asn Glu Tyr Ala Arg Ser
                565                 570                 575
```

```
Lys Lys Ala Asp Ala Val Ser Phe Ser Arg Ser Gly Thr Gln Gly Ala
            580                 585                 590

Gln Ala Asn Gln Ile Phe Trp Ser Gly Asp Gln Glu Ser Thr Phe Gly
        595                 600                 605

Ala Phe Gln Gln Ala Val Asn Ala Gly Leu Thr Ala Ser Met Ser Gly
        610                 615                 620

Val Pro Tyr Trp Ser Trp Asp Met Ala Gly Phe Thr Gly Thr Tyr Pro
625                 630                 635                 640

Thr Ala Glu Leu Tyr Lys Arg Ala Thr Glu Met Ala Ala Phe Ala Pro
                645                 650                 655

Val Met Gln Phe His Ser Glu Ser Asn Gly Ser Ser Gly Ile Asn Glu
            660                 665                 670

Glu Arg Ser Pro Trp Asn Ala Gln Ala Arg Thr Gly Asp Asn Thr Ile
        675                 680                 685

Ile Ser His Phe Ala Lys Tyr Thr Asn Thr Arg Met Asn Leu Leu Pro
        690                 695                 700

Tyr Ile Tyr Ser Glu Ala Lys Met Ala Ser Asp Thr Gly Val Pro Met
705                 710                 715                 720

Met Arg Ala Met Ala Leu Glu Tyr Pro Lys Asp Thr Asn Thr Tyr Gly
                725                 730                 735

Leu Thr Gln Gln Tyr Met Phe Gly Gly Asn Leu Leu Ile Ala Pro Val
            740                 745                 750

Met Asn Gln Gly Glu Thr Asn Lys Ser Ile Tyr Leu Pro Gln Gly Asp
        755                 760                 765

Trp Ile Asp Phe Trp Phe Gly Ala Gln Arg Pro Gly Gly Arg Thr Ile
        770                 775                 780

Ser Tyr Thr Ala Gly Ile Asp Asp Leu Pro Val Phe Val Lys Phe Gly
785                 790                 795                 800

Ser Ile Leu Pro Met Asn Leu Asn Ala Gln Tyr Gln Val Gly Gly Thr
                805                 810                 815

Ile Gly Asn Ser Leu Thr Ser Tyr Thr Asn Leu Ala Phe Arg Ile Tyr
            820                 825                 830

Pro Leu Gly Thr Thr Thr Tyr Asp Trp Asn Asp Asp Ile Gly Gly Ser
        835                 840                 845

Val Lys Thr Ile Thr Ser Thr Glu Gln Tyr Gly Leu Asn Lys Glu Thr
        850                 855                 860

Val Thr Val Pro Ala Ile Asn Ser Thr Lys Thr Leu Gln Val Phe Thr
865                 870                 875                 880

Thr Lys Pro Ser Ser Val Thr Val Gly Gly Ser Val Met Thr Glu Tyr
                885                 890                 895

Ser Thr Leu Thr Ala Leu Thr Gly Ala Ser Thr Gly Trp Tyr Tyr Asp
            900                 905                 910

Thr Val Gln Lys Phe Thr Tyr Val Lys Leu Gly Ser Ser Ala Ser Ala
        915                 920                 925

Gln Ser Val Val Leu Asn Gly Val Asn Lys Val Glu Tyr Glu Ala Glu
        930                 935                 940

Phe Gly Val Gln Ser Gly Val Ser Thr Asn Thr Asn His Ala Gly Tyr
945                 950                 955                 960

Thr Gly Thr Gly Phe Val Asp Gly Phe Glu Thr Leu Gly Asp Asn Val
                965                 970                 975

Ala Phe Asp Val Ser Val Lys Ala Ala Gly Thr Tyr Thr Met Lys Val
            980                 985                 990
```

-continued

```
Arg Tyr Ser Ser Gly Ala Gly Asn  Gly Ser Arg Ala Ile  Tyr Val Asn
        995                 1000                 1005

Asn Thr  Lys Val Thr Asp Leu  Ala Leu Pro Gln Thr  Thr Ser Trp
    1010                 1015                 1020

Asp Thr  Trp Gly Thr Ala Thr  Phe Ser Val Ser Leu  Ser Thr Gly
    1025                 1030                 1035

Leu Asn  Thr Val Lys Val Ser  Tyr Asp Gly Thr Ser  Ser Leu Gly
    1040                 1045                 1050

Ile Asn  Phe Asp Asn Ile Ala  Ile Val Glu Gln
    1055                 1060

<210> SEQ ID NO 2
<211> LENGTH: 1064
<212> TYPE: PRT
<213> ORGANISM: Bacillus globisporus

<400> SEQUENCE: 2

Ile Asp Gly Val Tyr His Ala Pro Tyr Gly Ile Asp Asp Leu Tyr Glu
 1               5                  10                  15

Ile Gln Ala Thr Glu Arg Ser Pro Arg Asp Pro Val Ala Gly Glu Thr
            20                  25                  30

Val Tyr Ile Lys Ile Thr Thr Trp Pro Ile Glu Pro Gly Gln Thr Ala
        35                  40                  45

Trp Val Thr Trp Thr Lys Asn Gly Val Ala Gln Pro Ala Val Gly Ala
    50                  55                  60

Ala Tyr Lys Tyr Asn Ser Gly Asn Asn Thr Tyr Trp Glu Ala Asn Leu
65                  70                  75                  80

Gly Ser Phe Ala Lys Gly Asp Val Ile Ser Tyr Thr Val Arg Gly Asn
                85                  90                  95

Lys Asp Gly Ala Asn Glu Lys Thr Ala Gly Pro Phe Thr Phe Thr Val
            100                 105                 110

Thr Asp Trp Glu Tyr Val Ser Ser Ile Gly Ser Val Thr Asn Asn Thr
        115                 120                 125

Asn Arg Val Leu Leu Asn Ala Val Pro Asn Thr Gly Thr Leu Ser Pro
    130                 135                 140

Lys Ile Asn Ile Ser Phe Thr Ala Asp Asp Val Phe Arg Val Gln Leu
145                 150                 155                 160

Ser Pro Thr Gly Ser Gly Thr Leu Ser Thr Gly Leu Ser Asn Phe Thr
                165                 170                 175

Val Thr Asp Ser Ala Ser Thr Ala Trp Ile Ser Thr Ser Lys Leu Lys
            180                 185                 190

Leu Lys Val Asp Lys Asn Pro Phe Lys Leu Ser Val Tyr Lys Pro Asp
        195                 200                 205

Gly Thr Thr Leu Ile Ala Arg Gln Tyr Asp Ser Thr Ala Asn Arg Asn
    210                 215                 220

Leu Ala Trp Leu Thr Asn Gly Ser Thr Val Ile Asn Lys Ile Glu Asp
225                 230                 235                 240

His Phe Tyr Ser Pro Ala Ser Glu Glu Phe Gly Phe Gly Glu Arg
                245                 250                 255

Tyr Asn Asn Phe Arg Lys Arg Gly Thr Asp Val Asp Thr Tyr Val Tyr
            260                 265                 270

Asn Gln Tyr Lys Asn Gln Asn Asp Arg Thr Tyr Met Ala Ile Pro Phe
        275                 280                 285

Met Leu Asn Ser Ser Gly Tyr Gly Ile Phe Val Asn Ser Thr Tyr Tyr
    290                 295                 300
```

```
Ser Lys Phe Arg Leu Ala Thr Glu Arg Ser Asp Met Tyr Ser Phe Thr
305                 310                 315                 320

Ala Asp Thr Gly Gly Ser Ala Asn Ser Thr Leu Asp Tyr Tyr Phe Ile
            325                 330                 335

Tyr Gly Asn Asp Leu Lys Gly Val Val Ser Asn Tyr Ala Asn Ile Thr
                340                 345                 350

Gly Lys Pro Ala Ala Leu Pro Lys Trp Ala Phe Gly Leu Trp Met Ser
            355                 360                 365

Ala Asn Glu Trp Asp Arg Gln Ser Lys Val Ala Thr Ala Ile Asn Asn
370                 375                 380

Ala Asn Thr Asn Asn Ile Pro Ala Thr Ala Val Val Leu Glu Gln Trp
385                 390                 395                 400

Ser Asp Glu Asn Thr Phe Tyr Met Phe Asn Asp Ala Gln Tyr Thr Ala
                405                 410                 415

Lys Pro Gly Gly Ser Thr His Ser Tyr Thr Asp Tyr Ile Phe Pro Ala
                420                 425                 430

Ala Gly Arg Trp Pro Asn Pro Lys Gln Met Ala Asp Asn Val His Ser
            435                 440                 445

Asn Gly Met Lys Leu Val Leu Trp Gln Val Pro Ile Gln Lys Trp Thr
            450                 455                 460

Ala Ala Pro His Leu Gln Lys Asp Asn Asp Glu Ser Tyr Met Ile Ala
465                 470                 475                 480

Gln Asn Tyr Ala Val Gly Asn Gly Ser Gly Gln Tyr Arg Ile Pro
                485                 490                 495

Ser Gly Gln Trp Phe Glu Asn Ser Leu Leu Leu Asp Phe Thr Asn Pro
            500                 505                 510

Ser Ala Lys Asn Trp Trp Met Ser Lys Arg Ala Tyr Leu Phe Asp Gly
            515                 520                 525

Val Gly Ile Asp Gly Phe Lys Thr Asp Gly Gly Glu Met Val Trp Gly
            530                 535                 540

Arg Trp Asn Thr Phe Ala Asn Gly Lys Lys Gly Asp Glu Met Arg Asn
545                 550                 555                 560

Gln Tyr Pro Asn Asp Tyr Val Lys Ala Tyr Asn Glu Tyr Ala Arg Ser
                565                 570                 575

Lys Lys Ser Asp Ala Val Ser Phe Ser Arg Ser Gly Thr Gln Gly Ala
            580                 585                 590

Gln Ala Asn Gln Ile Phe Trp Ser Gly Asp Gln Glu Ser Thr Phe Gly
            595                 600                 605

Ala Phe Gln Gln Ala Val Gln Ala Gly Leu Thr Ala Gly Leu Ser Gly
610                 615                 620

Val Pro Tyr Trp Ser Trp Asp Leu Ala Gly Phe Thr Gly Ala Tyr Pro
625                 630                 635                 640

Ser Ala Glu Leu Tyr Lys Arg Ala Thr Ala Met Ser Ala Phe Ala Pro
                645                 650                 655

Ile Met Gln Phe His Ser Glu Ala Asn Gly Ser Ser Gly Ile Asn Glu
                660                 665                 670

Glu Arg Ser Pro Trp Asn Ala Gln Ala Arg Thr Gly Asp Asn Thr Ile
            675                 680                 685

Ile Ser His Phe Ala Lys Tyr Thr Asn Thr Arg Met Asn Leu Leu Pro
            690                 695                 700

Tyr Ile Tyr Ser Glu Ala Lys Ala Ala Ser Asp Thr Gly Val Pro Met
705                 710                 715                 720
```

```
Met Arg Ala Met Ala Leu Glu Tyr Pro Ser Asp Thr Gln Thr Tyr Gly
            725                 730                 735
Leu Thr Gln Gln Tyr Met Phe Gly Gly Ser Leu Leu Val Ala Pro Val
        740                 745                 750
Leu Asn Gln Gly Glu Thr Asn Lys Asn Ile Tyr Leu Pro Gln Gly Asp
        755                 760                 765
Trp Ile Asp Phe Trp Phe Gly Ala Gln Arg Pro Gly Gly Arg Thr Ile
    770                 775                 780
Ser Tyr Tyr Ala Gly Val Asp Asp Leu Pro Val Phe Val Lys Ser Gly
785                 790                 795                 800
Ser Ile Leu Pro Met Asn Leu Asn Gly Gln Tyr Gln Val Gly Gly Thr
                805                 810                 815
Ile Gly Asn Ser Leu Thr Ala Tyr Asn Asn Leu Thr Phe Arg Ile Tyr
            820                 825                 830
Pro Leu Gly Thr Thr Thr Tyr Ser Trp Asn Asp Asp Ile Gly Gly Ser
        835                 840                 845
Val Lys Thr Ile Thr Ser Thr Glu Gln Tyr Gly Leu Asn Lys Glu Thr
    850                 855                 860
Val Thr Leu Pro Ala Ile Asn Ser Ala Lys Thr Leu Gln Val Phe Thr
865                 870                 875                 880
Thr Lys Pro Ser Ser Val Thr Leu Gly Gly Thr Ala Leu Thr Ala His
                885                 890                 895
Ser Thr Leu Ser Ala Leu Ile Gly Ala Ser Ser Gly Trp Tyr Tyr Asp
            900                 905                 910
Thr Val Gln Lys Leu Ala Tyr Val Lys Leu Gly Ala Ser Ser Ser Ala
        915                 920                 925
Gln Thr Val Val Leu Asp Gly Val Asn Lys Val Glu Tyr Glu Ala Glu
    930                 935                 940
Phe Gly Thr Leu Thr Gly Val Thr Thr Asn Thr Asn His Ala Gly Tyr
945                 950                 955                 960
Met Gly Thr Gly Phe Val Asp Gly Phe Asp Ala Ala Gly Asp Ala Val
                965                 970                 975
Thr Phe Asp Val Ser Val Lys Ala Ala Gly Thr Tyr Ala Leu Lys Val
            980                 985                 990
Arg Tyr Ala Ser Ala Gly Gly Asn Ala Ser Arg Ala Ile Tyr Val Asn
        995                 1000                1005
Asn Ala Lys Val Thr Asp Leu Ala Leu Pro Ala Thr Ala Asn Trp Asp
    1010                1015                1020
Thr Trp Gly Thr Ala Thr Val Asn Val Ala Leu Asn Ala Gly Tyr Asn
1025                1030                1035                1040
Ser Ile Lys Val Ser Tyr Asp Asn Thr Asn Thr Leu Gly Ile Asn Leu
                1045                1050                1055
Asp Asn Ile Ala Ile Val Glu His
            1060
```

<210> SEQ ID NO 3
<211> LENGTH: 3192
<212> TYPE: DNA
<213> ORGANISM: Bacillus globisporus

<400> SEQUENCE: 3
attgatggtg tttatcatgc gccatacgga atcgatgatc tgtacgagat tcaggcgacg    60
gagcggagtc caagagatcc cgttgcaggc gatactgtgt atatcaagat aacaacgtgg   120

```
cccattgaat caggacaaac ggcttgggtg acctggacga aaaacggtgt caatcaagct      180
gctgtcggag cagcattcaa atacaacagc ggcaacaaca cttactggga agcgaacctt      240
ggcacttttg caaaggggga cgtgatcagt ataccgttc atggcaacaa ggatggcgcg       300
aatgagaagg ttatcggtcc ttttactttt accgtaacgg gatgggaatc cgttagcagt      360
atcagctcta ttacggataa tacgaaccgt gttgtgctga atgcggtgcc gaatacaggc      420
acattgaagc caaagatcaa cctttccttt acggcggatg atgtcctccg cgtacaggtt      480
tctccaaccg gaacaggaac gttaagcagt ggacttagta attacacagt ttcagatacc      540
gcctcaacca cttggcttac aacttccaag ctgaaggtga aggtggataa gaatccattc      600
aaacttagtg tgtataagcc tgatggaacg acgttgattg cccgtcaata tgacagcact      660
acgaatcgta acattgcctg gttaaccaat ggcagtacaa tcatcgacaa ggtagaagat      720
cattttatt caccggcttc cgaggagttt tttggctttg gagagcatta caacaacttc       780
cgtaaacgcg gaaatgatgt ggacacctat gtgttcaacc agtataagaa tcaaaatgac      840
cgcacctaca tggcaattcc ttttatgctt aacagcagcg gttatggcat tttcgtaaat      900
tcaacgtatt attccaaatt tcggttggca accgaacgca ccgatatgtt cagctttacg      960
gctgatacag ggggtagtgc cgcctcgatg ctggattatt atttcattta cggtaatgat     1020
ttgaaaaatg tggtgagtaa ctacgctaac attaccggta agccaacagc gctgccgaaa     1080
tgggctttcg ggttatggat gtcagctaac gagtgggatc gtcaaaccaa ggtgaataca     1140
gccattaata acgcgaactc caataatatt ccggctacag cggttgtgct cgaacagtgg     1200
agtgatgaga cacgttttta tattttcaat gatgccacct ataccccgaa aacgggcagt     1260
gctgcgcatg cctataccga tttcactttc ccgacatctg ggagatggac ggatccaaaa     1320
gcgatggcag acaatgtgca taacaatggg atgaagctgg tgctttggca ggtccctatt     1380
cagaaatgga cttcaacgcc ctatacccag aaagataatg atgaagccta tatgacgggct    1440
cagaattatg cagttggcaa cggtagcgga ggccagtaca ggataccttc aggacaatgg     1500
ttcgagaaca gtttgctgct tgattttacg aatacggccg ccaaaaactg gtggatgtct     1560
aaacgcgctt atctgtttga tggtgtgggt atcgacggct tcaaaacaga tggcggtgaa     1620
atggtatggg gtcgctcaaa tactttctca acggtaagaa aaggcaatga aatgcgcaat     1680
caatacccga tgagtatgt gaaagcctat aacgagtacg cgcgctcgaa gaaagccgat      1740
gcggtctcct ttagccgttc cggcacgcaa ggcgcacagg cgaatcagat tttctggtcc     1800
ggtgaccaag agtcgacgtt tggtgctttt caacaagctg tgaatgcagg gcttacggca     1860
agtatgtctg cgcttcctta ttggagctgg gatatggcag gctttacagg cacttatcca     1920
acggctgagt tgtacaaacg tgctactgaa atggctgctt ttgcaccggt catgcagttt     1980
cattccgagt ctaacggcag ctctggtatc aacgaggaac gttctccatg gaacgcacaa     2040
gcgcgtacag gcgacaatac gatcattagt catttgcca aatatacgaa tacgcgcatg      2100
aatttgcttc cttatattta tagcgaagcg aagatggcta gtgatactgg cgttcccatg     2160
atgcgcgcca tggcgcttga atatccgaag gacacgaaca cgtacggttt gacacaacag     2220
tatatgttcg gaggtaattt acttattgct cctgttatga atcagggaga aacaaacaag     2280
agtatttatc ttccgcaggg ggattggatc gatttctggt tcggtgctca gcgtcctggc     2340
ggtcgaacaa tcagctacac ggccggcatc gatgatctac cggttttgt gaagtttggc      2400
agtattcttc cgatgaattt gaacgcgcaa tatcaagtgg gcgggaccat tggcaacagc     2460
```

-continued

| | |
|---|---|
| ttgacgagct acacgaatct cgcgttccgc atttatccgc ttgggacaac aacgtacgac | 2520 |
| tggaatgatg atattggcgg ttcggtgaaa accataactt ctacagagca atatgggttg | 2580 |
| aataaagaaa ccgtgactgt tccagcgatt aattctacca agacattgca agtgtttacg | 2640 |
| actaagcctt cctctgtaac ggtgggtggt tctgtgatga cagagtacag tactttaact | 2700 |
| gccctaacgg gagcgtcgac aggctggtac tatgatactg tacagaaatt cacttacgtc | 2760 |
| aagcttggtt caagtgcatc tgctcaatcc gttgtgctaa atggcgttaa taaggtggaa | 2820 |
| tatgaagcag aattcggcgt gcaaagcggc gtttcaacga acacgaacca tgcaggttat | 2880 |
| actggtacag gatttgtgga cggctttgag actcttggag acaatgttgc ttttgatgtt | 2940 |
| tccgtcaaag ccgcaggtac ttatacgatg aaggttcggt attcatccgg tgcaggcaat | 3000 |
| ggctcaagag ccatctatgt gaataacacc aaagtgacgg accttgcctt gccgcaaaca | 3060 |
| acaagctggg atacatgggg gactgctacg tttagcgtct cgctgagtac aggtctcaac | 3120 |
| acggtgaaag tcagctatga tggtaccagt tcacttggca ttaatttcga taacatcgcg | 3180 |
| attgtagagc aa | 3192 |

<210> SEQ ID NO 4
<211> LENGTH: 3192
<212> TYPE: DNA
<213> ORGANISM: Bacillus globisporus

<400> SEQUENCE: 4

| | |
|---|---|
| attgacggcg tataccacgc gccttacggg atcgacgatc tttatgagat tcaggcgacg | 60 |
| gagcgcagtc cgagagaccc tgtggccggg gagacggtgt atatcaaaat cacaacatgg | 120 |
| ccgatcgagc ccggacagac ggcatgggtg acctggacga aaaacggcgt cgcccagccg | 180 |
| gcggtcggtg ccgcctacaa gtacaacagc ggcaacaaca cctactggga ggcgaacctg | 240 |
| ggcagcttcg ccaaaggaga cgtaatttcc tacaccgttc gcggcaataa ggacggtgcc | 300 |
| aatgaaaaaa cggccggacc gttcaccttt accgtaaccg actgggaata cgtcagcagc | 360 |
| atcggctcgg tcacgaataa cacgaaccgt gtcctgctga atgcggtgcc gaacacgggg | 420 |
| acgctgtccc ccaagatcaa catttcgttc acggcggacg atgtgttccg cgttcagctc | 480 |
| tccctacgg gatcggggac gttgagcacg ggcctgagta attttaccgt cacggacagt | 540 |
| gcgtccacgg cctggatctc tacatccaaa ttaaagctga aggtggataa gaatccgttc | 600 |
| aaactgagcg tgtacaagcc ggacggcacg acgctgatcg cgcgccagta tgacagcacg | 660 |
| gccaaccgca atctcgcttg gctgaccaat ggcagcactg tcatcaataa aatcgaggac | 720 |
| cacttctact cgccggcgtc cgaggagttt ttcggcttcg gggagcgcta caacaacttc | 780 |
| cgcaagcgcg gaaccgacgt ggacacgtat gtctacaatc agtacaaaaa tcaaaacgac | 840 |
| cgcaccctata tggcaatccc cttcatgctg aacagcagcg ggtacggtat cttcgtaaac | 900 |
| tccacgtact actccaaatt ccgcttggca actgagcgct ccgatatgta cagttttacg | 960 |
| gccgataccg ggggcagcgc caattcgacg ctggattact actttatttta cggcaatgac | 1020 |
| ttgaagggcg tcgtcagcaa ttatgcgaac atcacaggca agccggctgc tctgcccaaa | 1080 |
| tgggcgtttg gcctctggat gtcggccaat gagtgggacc ggcaatccaa agtagcgact | 1140 |
| gcgatcaata acgccaatac gaacaacatc ccggcgacgg ccgtcgtgct ggagcagtgg | 1200 |
| agtgacgaga atacgttcta tatgttcaac gatgcgcagt atacggccaa acctggcggc | 1260 |
| agcacacact cctatacgga ctatatcttc ccggcggccg gccgttggcc gaatccgaag | 1320 |
| caaatggcgg ataatgtaca cagtaacggg atgaagctgg tgctgtggca ggtgccgatt | 1380 |

-continued

```
cagaaatgga ccgccgctcc tcatctgcag aaggacaacg acgaaagcta tatgatcgcg    1440
caaaattatg ccgtaggcaa cggcagcgga ggccagtacc gcatccctag cgggcaatgg    1500
tttgagaaca gcctgctgct ggacttcacg aacccgagcg ccaaaaactg gtggatgtcc    1560
aagcgcgcct atctgtttga tggcgtcggc atcgacgggt tcaagacgga cggaggggag    1620
atggtctggg gccgctggaa cacgttcgcc aatggcaaaa aaggcgatga atgcgcaac    1680 cagtacccga acgattacgt gaaggcctac aacgaatatg cgcgctcgaa gaaaagcgat    1740
gccgtcagct tcagccgttc gggcacgcaa ggggcgcaag cgaatcagat cttctggtcc    1800
ggtgaccagg aatcgacgtt cggtgccttc cagcaagccg tccaggcggg actgaccgca    1860
ggcttgtccg cgcgttccgta ttggagctgg gacttggctg gattcaccgg cgcttatccg    1920
tcggccgagc tatataaacg cgcgacggca atgtcggcat tgccccgat tatgcagttc    1980 cactccgaag ccaacggcag ttccggcatc aatgaggagc ggtccccgtg aatgctcag    2040 gcccggactg gcgacaacac gatcatcagc cattttgcca agtatacgaa cacccggatg    2100
aacctgcttc cttatattta cagcgaggct aaagcagcaa gcgatactgg cgtgccgatg    2160
atgcgcgcga tggcgctgga gtatccgagc gatacccaga cgtacggatt gacgcagcag    2220
tacatgttcg gcggcagcct gctggtggcg cctgtcttga accaaggcga gacgaataag    2280
aatatctacc ttccgcaagg agattggatc gacttctggt tcgcgcgcgca cgtccgggc    2340 gggcgaacga tcagctacta cgcgggcgtg gacgatcttc ccgtcttcgt gaagtccggc    2400
agcatcctgc cgatgaatct gaacgggcag tatcaggttg gcggcacgat cggcaacagc    2460
ttgaccgcct acaacaacct gacgttccgg atttatccac tgggtacgac gacgtacagc    2520
tggaatgatg acatcggcgg ctcggtgaag acgattacgt cgacagagca gtatggactg    2580
aataaagaga cggtgacgct tccggcgatc aactcggcga agacgctcca ggtgttcacg    2640
accaagccgt cgtcggtgac gctgggcggc acggcctca ccgcgcatag cacattaagc    2700
gcattgatcg cgcttcctc cggctggtat tacgatacgg tgcaaaagct cgcctatgtg    2760
aagctcggcg ccagctcatc ggcgcaaacc gtcgtgcttg acggcgtcaa caaggtcgag    2820
tatgaggctg agttcggcac acttaccggc gtcacgacca atacgaatca tgccggctat    2880
atgggtaccg gcttgtcga cggcttcgat gcggcaggcg atgcagtgac cttcgacgta    2940
tccgtcaaag cggccggcac gtatgcgctc aaggtccggt acgcttccgc tggtggcaac    3000
gcttcacgcg ctatctatgt caacaacgcc aaggtgaccg atctggcgct tccggcaacg    3060
gccaactggg acacctgggg gacggcaacc gtcaacgtag ccttaaacgc cggctacaac    3120
tcgatcaagg tcagctacga caacaccaat acgctcggca ttaatctcga taacattgcg    3180
atcgtggagc at                                                        3192
```

<210> SEQ ID NO 5
<211> LENGTH: 19
<212> TYPE: PRT
<213> ORGANISM: Bacillus globisporus

<400> SEQUENCE: 5

Ile Asp Gly Val Tyr His Ala Pro Tyr Gly Ile Asp Asp Leu Tyr Glu
 1               5                  10                  15

Ile Gln Ala

<210> SEQ ID NO 6
<211> LENGTH: 14

```
<212> TYPE: PRT
<213> ORGANISM: Bacillus globisporus

<400> SEQUENCE: 6

Gly Asn Glu Met Arg Asn Gln Tyr Pro Asn Glu Tyr Val Lys
 1               5                  10

<210> SEQ ID NO 7
<211> LENGTH: 14
<212> TYPE: PRT
<213> ORGANISM: Bacillus globisporus

<400> SEQUENCE: 7

Arg Gly Asn Asp Val Asp Thr Tyr Val Phe Asn Gln Tyr Lys
 1               5                  10

<210> SEQ ID NO 8
<211> LENGTH: 6
<212> TYPE: PRT
<213> ORGANISM: Bacillus globisporus

<400> SEQUENCE: 8

Asn Trp Trp Met Ser Lys
 1               5

<210> SEQ ID NO 9
<211> LENGTH: 12
<212> TYPE: PRT
<213> ORGANISM: Bacillus globisporus

<400> SEQUENCE: 9

Ile Thr Thr Trp Pro Ile Glu Ser Gly Gln Thr Ala
 1               5                  10

<210> SEQ ID NO 10
<211> LENGTH: 11
<212> TYPE: PRT
<213> ORGANISM: Bacillus globisporus

<400> SEQUENCE: 10

Trp Ala Phe Gly Leu Trp Met Ser Ala Asn Glu
 1               5                  10

<210> SEQ ID NO 11
<211> LENGTH: 18
<212> TYPE: PRT
<213> ORGANISM: Bacillus globisporus

<400> SEQUENCE: 11

Thr Asp Gly Gly Glu Met Val Trp Gly Arg Trp Asn Thr Phe Ala Asn
 1               5                  10                  15

Gly Lys

<210> SEQ ID NO 12
<211> LENGTH: 18
<212> TYPE: PRT
<213> ORGANISM: Bacillus globisporus

<400> SEQUENCE: 12

Ile Thr Thr Trp Pro Ile Glu Pro Gly Gln Thr Ala Trp Val Thr Trp
 1               5                  10                  15

Thr Lys
```

-continued

```
<210> SEQ ID NO 13
<211> LENGTH: 17
<212> TYPE: PRT
<213> ORGANISM: Bacillus globisporus

<400> SEQUENCE: 13

Trp Ala Phe Gly Leu Trp Met Ser Ala Asn Glu Trp Asp Arg Glu Ser
 1               5                  10                  15
Lys

<210> SEQ ID NO 14
<211> LENGTH: 20
<212> TYPE: PRT
<213> ORGANISM: Bacillus globisporus

<400> SEQUENCE: 14

Asn Ile Tyr Leu Pro Gln Gly Asp Trp Ile Asp Phe Trp Phe Gly Ala
 1               5                  10                  15
Gln Arg Pro Gly

<210> SEQ ID NO 15
<211> LENGTH: 3869
<212> TYPE: DNA
<213> ORGANISM: Bacillus globisporus
<220> FEATURE:
<221> NAME/KEY: CDS
<222> LOCATION: (241)...(3522)

<400> SEQUENCE: 15
```

| | |
|---|---:|
| tcatcgctac tggcaatcgg attcaaacaa atggctgcag ctcgcacaga cgattgtgga | 60 |
| aagggaatat ctgatttaac catacggcgg tcgcgattga ttgaatagga ttcgtggccg | 120 |
| cctaatattg aaaggggga tgcgtggagc agcgcatgca cggcgaggaa taactgttgt | 180 |
| tggagcctct aagtcattca tgtttagcaa acaaatttcg gtacgaaagg ggaaatgttt | 240 |

| | | |
|---|---|---:|
| atg tat gta agg aat cta aca ggt tca ttc cga ttt tct ctc tct ttt<br>Met Tyr Val Arg Asn Leu Thr Gly Ser Phe Arg Phe Ser Leu Ser Phe<br>  1                5                   10                  15 | | 288 |
| ttg ctc tgt ttc tgt ctc ttc gtc ccc tct att tat gcc att gat ggt<br>Leu Leu Cys Phe Cys Leu Phe Val Pro Ser Ile Tyr Ala Ile Asp Gly<br>                20                   25                   30 | | 336 |
| gtt tat cat gcg cca tac gga atc gat gat ctg tac gag att cag gcg<br>Val Tyr His Ala Pro Tyr Gly Ile Asp Asp Leu Tyr Glu Ile Gln Ala<br>        35                    40                   45 | | 384 |
| acg gag cgg agt cca aga gat ccc gtt gca ggc gat act gtg tat atc<br>Thr Glu Arg Ser Pro Arg Asp Pro Val Ala Gly Asp Thr Val Tyr Ile<br> 50                  55                   60 | | 432 |
| aag ata aca acg tgg ccc att gaa tca gga caa acg gct tgg gtg acc<br>Lys Ile Thr Thr Trp Pro Ile Glu Ser Gly Gln Thr Ala Trp Val Thr<br> 65                  70                75                   80 | | 480 |
| tgg acg aaa aac ggt gtc aat caa gct gct gtc gga gca gca ttc aaa<br>Trp Thr Lys Asn Gly Val Asn Gln Ala Ala Val Gly Ala Ala Phe Lys<br>                85                   90                   95 | | 528 |
| tac aac agc ggc aac aac act tac tgg gaa gcg aac ctt ggc act ttt<br>Tyr Asn Ser Gly Asn Asn Thr Tyr Trp Glu Ala Asn Leu Gly Thr Phe<br>              100                  105               110 | | 576 |
| gca aaa ggg gac gtg atc agt tat acc gtt cat ggc aac aag gat ggc<br>Ala Lys Gly Asp Val Ile Ser Tyr Thr Val His Gly Asn Lys Asp Gly<br>     115                  120                  125 | | 624 |
| gcg aat gag aag gtt atc ggt cct ttt act ttt acc gta acg gga tgg<br>Ala Asn Glu Lys Val Ile Gly Pro Phe Thr Phe Thr Val Thr Gly Trp<br> 130                  135                  140 | | 672 |

|  |  |  |  |  |  |  |  |  |  |  |  |  |  |  |  |
|---|---|---|---|---|---|---|---|---|---|---|---|---|---|---|---|
| gaa | tcc | gtt | agc | agt | atc | agc | tct | att | acg | gat | aat | acg | aac | cgt | gtt | 720 |
| Glu | Ser | Val | Ser | Ser | Ile | Ser | Ser | Ile | Thr | Asp | Asn | Thr | Asn | Arg | Val |
| 145 |  |  |  |  | 150 |  |  |  |  | 155 |  |  |  |  | 160 |

| gtg | ctg | aat | gcg | gtg | ccg | aat | aca | ggc | aca | ttg | aag | cca | aag | atc | aac | 768 |
| Val | Leu | Asn | Ala | Val | Pro | Asn | Thr | Gly | Thr | Leu | Lys | Pro | Lys | Ile | Asn |
|  |  |  |  | 165 |  |  |  |  | 170 |  |  |  |  | 175 |  |

| ctt | tcc | ttt | acg | gcg | gat | gat | gtc | ctc | cgc | gta | cag | gtt | tct | cca | acc | 816 |
| Leu | Ser | Phe | Thr | Ala | Asp | Asp | Val | Leu | Arg | Val | Gln | Val | Ser | Pro | Thr |
|  |  |  | 180 |  |  |  |  | 185 |  |  |  |  | 190 |  |  |

| gga | aca | gga | acg | tta | agc | agt | gga | ctt | agt | aat | tac | aca | gtt | tca | gat | 864 |
| Gly | Thr | Gly | Thr | Leu | Ser | Ser | Gly | Leu | Ser | Asn | Tyr | Thr | Val | Ser | Asp |
|  |  | 195 |  |  |  |  | 200 |  |  |  |  | 205 |  |  |  |

| acc | gcc | tca | acc | act | tgg | ctt | aca | act | tcc | aag | ctg | aag | gtg | aag | gtg | 912 |
| Thr | Ala | Ser | Thr | Thr | Trp | Leu | Thr | Thr | Ser | Lys | Leu | Lys | Val | Lys | Val |
| 210 |  |  |  |  | 215 |  |  |  |  | 220 |  |  |  |  |  |

| gat | aag | aat | cca | ttc | aaa | ctt | agt | gtg | tat | aag | cct | gat | gga | acg | acg | 960 |
| Asp | Lys | Asn | Pro | Phe | Lys | Leu | Ser | Val | Tyr | Lys | Pro | Asp | Gly | Thr | Thr |
| 225 |  |  |  |  | 230 |  |  |  |  | 235 |  |  |  |  | 240 |

| ttg | att | gcc | cgt | caa | tat | gac | agc | act | acg | aat | cgt | aac | att | gcc | tgg | 1008 |
| Leu | Ile | Ala | Arg | Gln | Tyr | Asp | Ser | Thr | Thr | Asn | Arg | Asn | Ile | Ala | Trp |
|  |  |  |  | 245 |  |  |  |  | 250 |  |  |  |  | 255 |  |

| tta | acc | aat | ggc | agt | aca | atc | atc | gac | aag | gta | gaa | gat | cat | ttt | tat | 1056 |
| Leu | Thr | Asn | Gly | Ser | Thr | Ile | Ile | Asp | Lys | Val | Glu | Asp | His | Phe | Tyr |
|  |  |  | 260 |  |  |  |  | 265 |  |  |  |  | 270 |  |  |

| tca | ccg | gct | tcc | gag | gag | ttt | ttt | ggc | ttt | gga | gag | cat | tac | aac | aac | 1104 |
| Ser | Pro | Ala | Ser | Glu | Glu | Phe | Phe | Gly | Phe | Gly | Glu | His | Tyr | Asn | Asn |
|  |  | 275 |  |  |  |  | 280 |  |  |  |  | 285 |  |  |  |

| ttc | cgt | aaa | cgc | gga | aat | gat | gtg | gac | acc | tat | gtg | ttc | aac | cag | tat | 1152 |
| Phe | Arg | Lys | Arg | Gly | Asn | Asp | Val | Asp | Thr | Tyr | Val | Phe | Asn | Gln | Tyr |
| 290 |  |  |  |  | 295 |  |  |  |  | 300 |  |  |  |  |  |

| aag | aat | caa | aat | gac | cgc | acc | tac | atg | gca | att | cct | ttt | atg | ctt | aac | 1200 |
| Lys | Asn | Gln | Asn | Asp | Arg | Thr | Tyr | Met | Ala | Ile | Pro | Phe | Met | Leu | Asn |
| 305 |  |  |  |  | 310 |  |  |  |  | 315 |  |  |  |  | 320 |

| agc | agc | ggt | tat | ggc | att | ttc | gta | aat | tca | acg | tat | tat | tcc | aaa | ttt | 1248 |
| Ser | Ser | Gly | Tyr | Gly | Ile | Phe | Val | Asn | Ser | Thr | Tyr | Tyr | Ser | Lys | Phe |
|  |  |  |  | 325 |  |  |  |  | 330 |  |  |  |  | 335 |  |

| cgg | ttg | gca | acc | gaa | cgc | acc | gat | atg | ttc | agc | ttt | acg | gct | gat | aca | 1296 |
| Arg | Leu | Ala | Thr | Glu | Arg | Thr | Asp | Met | Phe | Ser | Phe | Thr | Ala | Asp | Thr |
|  |  |  | 340 |  |  |  |  | 345 |  |  |  |  | 350 |  |  |

| ggg | ggt | agt | gcc | gcc | tcg | atg | ctg | gat | tat | tat | ttc | att | tac | ggt | aat | 1344 |
| Gly | Gly | Ser | Ala | Ala | Ser | Met | Leu | Asp | Tyr | Tyr | Phe | Ile | Tyr | Gly | Asn |
|  |  | 355 |  |  |  |  | 360 |  |  |  |  | 365 |  |  |  |

| gat | ttg | aaa | aat | gtg | gtg | agt | aac | tac | gct | aac | att | acc | ggt | aag | cca | 1392 |
| Asp | Leu | Lys | Asn | Val | Val | Ser | Asn | Tyr | Ala | Asn | Ile | Thr | Gly | Lys | Pro |
| 370 |  |  |  |  | 375 |  |  |  |  | 380 |  |  |  |  |  |

| aca | gcg | ctg | ccg | aaa | tgg | gct | ttc | ggg | tta | tgg | atg | tca | gct | aac | gag | 1440 |
| Thr | Ala | Leu | Pro | Lys | Trp | Ala | Phe | Gly | Leu | Trp | Met | Ser | Ala | Asn | Glu |
| 385 |  |  |  |  | 390 |  |  |  |  | 395 |  |  |  |  | 400 |

| tgg | gat | cgt | caa | acc | aag | gtg | aat | aca | gcc | att | aat | aac | gcg | aac | tcc | 1488 |
| Trp | Asp | Arg | Gln | Thr | Lys | Val | Asn | Thr | Ala | Ile | Asn | Asn | Ala | Asn | Ser |
|  |  |  |  | 405 |  |  |  |  | 410 |  |  |  |  | 415 |  |

| aat | aat | att | ccg | gct | aca | gcg | gtt | gtg | ctc | gaa | cag | tgg | agt | gat | gag | 1536 |
| Asn | Asn | Ile | Pro | Ala | Thr | Ala | Val | Val | Leu | Glu | Gln | Trp | Ser | Asp | Glu |
|  |  |  | 420 |  |  |  |  | 425 |  |  |  |  | 430 |  |  |

| aac | acg | ttt | tat | att | ttc | aat | gat | gcc | acc | tat | acc | ccg | aaa | acg | ggc | 1584 |
| Asn | Thr | Phe | Tyr | Ile | Phe | Asn | Asp | Ala | Thr | Tyr | Thr | Pro | Lys | Thr | Gly |
|  |  | 435 |  |  |  |  | 440 |  |  |  |  | 445 |  |  |  |

| agt | gct | gcg | cat | gcc | tat | acc | gat | ttc | act | ttc | ccg | aca | tct | ggg | aga | 1632 |
| Ser | Ala | Ala | His | Ala | Tyr | Thr | Asp | Phe | Thr | Phe | Pro | Thr | Ser | Gly | Arg |

-continued

|     |     |     |
| --- | --- | --- |
| 450 | 455 | 460 |

| | | | | | | | | | | | | | | | |
|---|---|---|---|---|---|---|---|---|---|---|---|---|---|---|---|
| tgg | acg | gat | cca | aaa | gcg | atg | gca | gac | aat | gtg | cat | aac | aat | ggg | atg | 1680 |
| Trp | Thr | Asp | Pro | Lys | Ala | Met | Ala | Asp | Asn | Val | His | Asn | Asn | Gly | Met |
| 465 | | | | 470 | | | | | 475 | | | | | 480 | |

| aag | ctg | gtg | ctt | tgg | cag | gtc | cct | att | cag | aaa | tgg | act | tca | acg | ccc | 1728 |
|---|---|---|---|---|---|---|---|---|---|---|---|---|---|---|---|---|
| Lys | Leu | Val | Leu | Trp | Gln | Val | Pro | Ile | Gln | Lys | Trp | Thr | Ser | Thr | Pro |
| | | | | 485 | | | | | 490 | | | | | 495 | |

| tat | acc | cag | aaa | gat | aat | gat | gaa | gcc | tat | atg | acg | gct | cag | aat | tat | 1776 |
|---|---|---|---|---|---|---|---|---|---|---|---|---|---|---|---|---|
| Tyr | Thr | Gln | Lys | Asp | Asn | Asp | Glu | Ala | Tyr | Met | Thr | Ala | Gln | Asn | Tyr |
| | | | 500 | | | | | 505 | | | | | 510 | | |

| gca | gtt | ggc | aac | ggt | agc | gga | ggc | cag | tac | agg | ata | cct | tca | gga | caa | 1824 |
|---|---|---|---|---|---|---|---|---|---|---|---|---|---|---|---|---|
| Ala | Val | Gly | Asn | Gly | Ser | Gly | Gly | Gln | Tyr | Arg | Ile | Pro | Ser | Gly | Gln |
| | | | 515 | | | | | 520 | | | | | 525 | | |

| tgg | ttc | gag | aac | agt | ttg | ctg | ctt | gat | ttt | acg | aat | acg | gcc | gcc | aaa | 1872 |
|---|---|---|---|---|---|---|---|---|---|---|---|---|---|---|---|---|
| Trp | Phe | Glu | Asn | Ser | Leu | Leu | Leu | Asp | Phe | Thr | Asn | Thr | Ala | Ala | Lys |
| | 530 | | | | | 535 | | | | | 540 | | | | |

| aac | tgg | tgg | atg | tct | aaa | cgc | gct | tat | ctg | ttt | gat | ggt | gtg | ggt | atc | 1920 |
|---|---|---|---|---|---|---|---|---|---|---|---|---|---|---|---|---|
| Asn | Trp | Trp | Met | Ser | Lys | Arg | Ala | Tyr | Leu | Phe | Asp | Gly | Val | Gly | Ile |
| 545 | | | | 550 | | | | | 555 | | | | | 560 | |

| gac | ggc | ttc | aaa | aca | gat | ggc | ggt | gaa | atg | gta | tgg | ggt | cgc | tca | aat | 1968 |
|---|---|---|---|---|---|---|---|---|---|---|---|---|---|---|---|---|
| Asp | Gly | Phe | Lys | Thr | Asp | Gly | Gly | Glu | Met | Val | Trp | Gly | Arg | Ser | Asn |
| | | | 565 | | | | | 570 | | | | | 575 | | |

| act | ttc | tca | aac | ggt | aag | aaa | ggc | aat | gaa | atg | cgc | aat | caa | tac | ccg | 2016 |
|---|---|---|---|---|---|---|---|---|---|---|---|---|---|---|---|---|
| Thr | Phe | Ser | Asn | Gly | Lys | Lys | Gly | Asn | Glu | Met | Arg | Asn | Gln | Tyr | Pro |
| | | 580 | | | | | 585 | | | | | 590 | | | |

| aat | gag | tat | gtg | aaa | gcc | tat | aac | gag | tac | gcg | cgc | tcg | aag | aaa | gcc | 2064 |
|---|---|---|---|---|---|---|---|---|---|---|---|---|---|---|---|---|
| Asn | Glu | Tyr | Val | Lys | Ala | Tyr | Asn | Glu | Tyr | Ala | Arg | Ser | Lys | Lys | Ala |
| | 595 | | | | | 600 | | | | | 605 | | | | |

| gat | gcg | gtc | tcc | ttt | agc | cgt | tcc | ggc | acg | caa | ggc | gca | cag | gcg | aat | 2112 |
|---|---|---|---|---|---|---|---|---|---|---|---|---|---|---|---|---|
| Asp | Ala | Val | Ser | Phe | Ser | Arg | Ser | Gly | Thr | Gln | Gly | Ala | Gln | Ala | Asn |
| 610 | | | | 615 | | | | | 620 | | | | | | |

| cag | att | ttc | tgg | tcc | ggt | gac | caa | gag | tcg | acg | ttt | ggt | gct | ttt | caa | 2160 |
|---|---|---|---|---|---|---|---|---|---|---|---|---|---|---|---|---|
| Gln | Ile | Phe | Trp | Ser | Gly | Asp | Gln | Glu | Ser | Thr | Phe | Gly | Ala | Phe | Gln |
| 625 | | | | 630 | | | | | 635 | | | | | 640 | |

| caa | gct | gtg | aat | gca | ggg | ctt | acg | gca | agt | atg | tct | ggc | gtt | cct | tat | 2208 |
|---|---|---|---|---|---|---|---|---|---|---|---|---|---|---|---|---|
| Gln | Ala | Val | Asn | Ala | Gly | Leu | Thr | Ala | Ser | Met | Ser | Gly | Val | Pro | Tyr |
| | | | 645 | | | | | 650 | | | | | 655 | | |

| tgg | agc | tgg | gat | atg | gca | ggc | ttt | aca | ggc | act | tat | cca | acg | gct | gag | 2256 |
|---|---|---|---|---|---|---|---|---|---|---|---|---|---|---|---|---|
| Trp | Ser | Trp | Asp | Met | Ala | Gly | Phe | Thr | Gly | Thr | Tyr | Pro | Thr | Ala | Glu |
| | | | 660 | | | | | 665 | | | | | 670 | | |

| ttg | tac | aaa | cgt | gct | act | gaa | atg | gct | gct | ttt | gca | ccg | gtc | atg | cag | 2304 |
|---|---|---|---|---|---|---|---|---|---|---|---|---|---|---|---|---|
| Leu | Tyr | Lys | Arg | Ala | Thr | Glu | Met | Ala | Ala | Phe | Ala | Pro | Val | Met | Gln |
| | | 675 | | | | | 680 | | | | | 685 | | | |

| ttt | cat | tcc | gag | tct | aac | ggc | agc | tct | ggt | atc | aac | gag | gaa | cgt | tct | 2352 |
|---|---|---|---|---|---|---|---|---|---|---|---|---|---|---|---|---|
| Phe | His | Ser | Glu | Ser | Asn | Gly | Ser | Ser | Gly | Ile | Asn | Glu | Glu | Arg | Ser |
| | 690 | | | | | 695 | | | | | 700 | | | | |

| cca | tgg | aac | gca | caa | gcg | cgt | aca | ggc | gac | aat | acg | atc | att | agt | cat | 2400 |
|---|---|---|---|---|---|---|---|---|---|---|---|---|---|---|---|---|
| Pro | Trp | Asn | Ala | Gln | Ala | Arg | Thr | Gly | Asp | Asn | Thr | Ile | Ile | Ser | His |
| 705 | | | | 710 | | | | | 715 | | | | | 720 | |

| ttt | gcc | aaa | tat | acg | aat | acg | cgc | atg | aat | ttg | ctt | cct | tat | att | tat | 2448 |
|---|---|---|---|---|---|---|---|---|---|---|---|---|---|---|---|---|
| Phe | Ala | Lys | Tyr | Thr | Asn | Thr | Arg | Met | Asn | Leu | Leu | Pro | Tyr | Ile | Tyr |
| | | | 725 | | | | | 730 | | | | | 735 | | |

| agc | gaa | gcg | aag | atg | gct | agt | gat | act | ggc | gtt | ccc | atg | atg | cgc | gcc | 2496 |
|---|---|---|---|---|---|---|---|---|---|---|---|---|---|---|---|---|
| Ser | Glu | Ala | Lys | Met | Ala | Ser | Asp | Thr | Gly | Val | Pro | Met | Met | Arg | Ala |
| | | | 740 | | | | | 745 | | | | | 750 | | |

| atg | gcg | ctt | gaa | tat | ccg | aag | gac | acg | aac | acg | tac | ggt | ttg | aca | caa | 2544 |
|---|---|---|---|---|---|---|---|---|---|---|---|---|---|---|---|---|
| Met | Ala | Leu | Glu | Tyr | Pro | Lys | Asp | Thr | Asn | Thr | Tyr | Gly | Leu | Thr | Gln |
| | | | 755 | | | | | 760 | | | | | 765 | | |

| cag | tat | atg | ttc | gga | ggt | aat | tta | ctt | att | gct | cct | gtt | atg | aat | cag | 2592 |
|---|---|---|---|---|---|---|---|---|---|---|---|---|---|---|---|---|

```
                                                            -continued

Gln Tyr Met Phe Gly Gly Asn Leu Leu Ile Ala Pro Val Met Asn Gln
    770                 775                 780 gga gaa aca aac aag agt att tat ctt ccg cag ggg gat tgg atc gat    2640
Gly Glu Thr Asn Lys Ser Ile Tyr Leu Pro Gln Gly Asp Trp Ile Asp
785                 790                 795                 800 ttc tgg ttc ggt gct cag cgt cct ggc ggt cga aca atc agc tac acg    2688
Phe Trp Phe Gly Ala Gln Arg Pro Gly Gly Arg Thr Ile Ser Tyr Thr
                805                 810                 815 gcc ggc atc gat gat cta ccg gtt ttt gtg aag ttt ggc agt att ctt    2736
Ala Gly Ile Asp Asp Leu Pro Val Phe Val Lys Phe Gly Ser Ile Leu
            820                 825                 830 ccg atg aat ttg aac gcg caa tat caa gtg ggc ggg acc att ggc aac    2784
Pro Met Asn Leu Asn Ala Gln Tyr Gln Val Gly Gly Thr Ile Gly Asn
        835                 840                 845 agc ttg acg agc tac acg aat ctc gcg ttc cgc att tat ccg ctt ggg    2832
Ser Leu Thr Ser Tyr Thr Asn Leu Ala Phe Arg Ile Tyr Pro Leu Gly
    850                 855                 860 aca aca acg tac gac tgg aat gat gat att ggc ggt tcg gtg aaa acc    2880
Thr Thr Thr Tyr Asp Trp Asn Asp Asp Ile Gly Gly Ser Val Lys Thr
865                 870                 875                 880 ata act tct aca gag caa tat ggg ttg aat aaa gaa acc gtg act gtt    2928
Ile Thr Ser Thr Glu Gln Tyr Gly Leu Asn Lys Glu Thr Val Thr Val
                885                 890                 895 cca gcg att aat tct acc aag aca ttg caa gtg ttt acg act aag cct    2976
Pro Ala Ile Asn Ser Thr Lys Thr Leu Gln Val Phe Thr Thr Lys Pro
            900                 905                 910 tcc tct gta acg gtg ggt ggt tct gtg atg aca gag tac agt act tta    3024
Ser Ser Val Thr Val Gly Gly Ser Val Met Thr Glu Tyr Ser Thr Leu
        915                 920                 925 act gcc cta acg gga gcg tcg aca ggc tgg tac tat gat act gta cag    3072
Thr Ala Leu Thr Gly Ala Ser Thr Gly Trp Tyr Tyr Asp Thr Val Gln
    930                 935                 940 aaa ttc act tac gtc aag ctt ggt tca agt gca tct gct caa tcc gtt    3120
Lys Phe Thr Tyr Val Lys Leu Gly Ser Ser Ala Ser Ala Gln Ser Val
945                 950                 955                 960 gtg cta aat ggc gtt aat aag gtg gaa tat gaa gca gaa ttc ggc gtg    3168
Val Leu Asn Gly Val Asn Lys Val Glu Tyr Glu Ala Glu Phe Gly Val
                965                 970                 975 caa agc ggc gtt tca acg aac acg aac cat gca ggt tat act ggt aca    3216
Gln Ser Gly Val Ser Thr Asn Thr Asn His Ala Gly Tyr Thr Gly Thr
            980                 985                 990 gga ttt gtg gac ggc ttt gag act ctt gga gac aat gtt gct ttt gat    3264
Gly Phe Val Asp Gly Phe Glu Thr Leu Gly Asp Asn Val Ala Phe Asp
        995                 1000                1005 gtt tcc gtc aaa gcc gca ggt act tat acg atg aag gtt cgg tat tca    3312
Val Ser Val Lys Ala Ala Gly Thr Tyr Thr Met Lys Val Arg Tyr Ser
    1010                1015                1020 tcc ggt gca ggc aat ggc tca aga gcc atc tat gtg aat aac acc aaa    3360
Ser Gly Ala Gly Asn Gly Ser Arg Ala Ile Tyr Val Asn Asn Thr Lys
1025                1030                1035                1040 gtg acg gac ctt gcc ttg ccg caa aca aca agc tgg gat aca tgg ggg    3408
Val Thr Asp Leu Ala Leu Pro Gln Thr Thr Ser Trp Asp Thr Trp Gly
                1045                1050                1055 act gct acg ttt agc gtc tcg ctg agt aca ggt ctc aac acg gtg aaa    3456
Thr Ala Thr Phe Ser Val Ser Leu Ser Thr Gly Leu Asn Thr Val Lys
            1060                1065                1070 gtc agc tat gat ggt acc agt tca ctt ggc att aat ttc gat aac atc    3504
Val Ser Tyr Asp Gly Thr Ser Ser Leu Gly Ile Asn Phe Asp Asn Ile
        1075                1080                1085
```

-continued

```
gcg att gta gag caa taa                                              3522
Ala Ile Val Glu Gln
       1090 aaggtcggga gggcaagtcc ctcccttaat ttctaatcga aagggagtat ccttgatgcg    3582 tccaccaaac aaagaaattc cacgtattct tgcttttttt acagcgttta cgttgtttgg    3642 ttcaacccct gccttgcttc ctgctccgcc tgcgcatgcc tatgtcagca gcctaggaaa    3702 tctcatttct tcgagtgtca ccggagatac cttgacgcta actgttgata acggtgcgga    3762 gccgagtgat gacctcttga ttgttcaagc ggtgcaaaac ggtattttga aggtggatta    3822 tcgtccaaat agcataacgc cgagcgcgaa gacgccgatg ctggatc                  3869

<210> SEQ ID NO 16
<211> LENGTH: 4986
<212> TYPE: DNA
<213> ORGANISM: Bacillus globisporus
<220> FEATURE:
<221> NAME/KEY: CDS
<222> LOCATION: (667)..(3948)

<400> SEQUENCE: 16
gagctcggga agaacccgtc cctgcaagct tggacgcagg cggtggagga ggcgggagtc      60
tacatcgctt ccgctatggc aggggctggg ggaggtgcat acggcttgat cggccactgc    120
tggggagggc tgctggcgtt cgagaccggc cactggctga aggcttgcgg gatgcaggag    180
ccgacgcatc tgttcgtgtc cgggtgcagc ccgccccatc tgctgcaagc gcggccggac    240
ttgggaacgg gaccatccgg cccggctccg ctccccgatg cctgccggat cgcccaagcg    300
taccgtatgc cttccaggcg cgggccgctg cttgcccggc tgagtgtatt cgccggccgc    360
cgagacccgg gcgtgtatgt ggatagtttg gccgaatggg gccgctatac ggcccgcata    420
tgcgatgttc atattggcga gggcgggcat gcagattggg gacctgatgc agaccgttgg    480
ctgccattcg tgcaaatgat tgcggagagg gaatattcgt cttcttgaag ccaggtgacc    540
tcagataaga tgtcgcacta agctgtatag tttcggaagg gaggtgaggc agagaagcgc    600
accatgagct gttagcttga cgtttaacgg tcaaaaccaa ttttactttg gaaggagca    660 agattt atg cat gga aga aac ata ccg aga ccc atc aag ctc att gtt       708
       Met His Gly Arg Asn Ile Pro Arg Pro Ile Lys Leu Ile Val
         1               5                  10 tct tgg ctg ctg att ttc ttt tta atg gtg cca agc atc tat gca att      756
Ser Trp Leu Leu Ile Phe Phe Leu Met Val Pro Ser Ile Tyr Ala Ile
 15                  20                  25                  30 gac ggc gta tac cac gcg cct tac ggg atc gac gat ctt tat gag att      804
Asp Gly Val Tyr His Ala Pro Tyr Gly Ile Asp Asp Leu Tyr Glu Ile
                 35                  40                  45 cag gcg acg gag cgc agt ccg aga gac cct gtg gcc ggg gag acg gtg      852
Gln Ala Thr Glu Arg Ser Pro Arg Asp Pro Val Ala Gly Glu Thr Val
             50                  55                  60 tat atc aaa atc aca aca tgg ccg atc gag ccc gga cag acg gca tgg      900
Tyr Ile Lys Ile Thr Thr Trp Pro Ile Glu Pro Gly Gln Thr Ala Trp
         65                  70                  75 gtg acc tgg acg aaa aac ggc gtc gcc cag ccg gcg gtc ggt gcc gcc      948
Val Thr Trp Thr Lys Asn Gly Val Ala Gln Pro Ala Val Gly Ala Ala
     80                  85                  90 tac aag tac aac agc ggc aac aac acc tac tgg gag gcg aac ctg ggc      996
Tyr Lys Tyr Asn Ser Gly Asn Asn Thr Tyr Trp Glu Ala Asn Leu Gly
 95                 100                 105                 110 agc ttc gcc aaa gga gac gta att tcc tac acc gtt cgc ggc aat aag     1044
Ser Phe Ala Lys Gly Asp Val Ile Ser Tyr Thr Val Arg Gly Asn Lys
```

```
                         115                 120                 125
gac ggt gcc aat gaa aaa acg gcc gga ccg ttc acc ttt acc gta acc      1092
Asp Gly Ala Asn Glu Lys Thr Ala Gly Pro Phe Thr Phe Thr Val Thr
            130                 135                 140 gac tgg gaa tac gtc agc agc atc ggc tcg gtc acg aat aac acg aac      1140
Asp Trp Glu Tyr Val Ser Ser Ile Gly Ser Val Thr Asn Asn Thr Asn
        145                 150                 155 cgt gtc ctg ctg aat gcg gtg ccg aac acg ggg acg ctg tcc ccc aag      1188
Arg Val Leu Leu Asn Ala Val Pro Asn Thr Gly Thr Leu Ser Pro Lys
    160                 165                 170 atc aac att tcg ttc acg gcg gac gat gtg ttc cgc gtt cag ctc tcc      1236
Ile Asn Ile Ser Phe Thr Ala Asp Asp Val Phe Arg Val Gln Leu Ser
175                 180                 185                 190 cct acg gga tcg ggg acg ttg agc acg ggc ctg agt aat ttt acc gtc      1284
Pro Thr Gly Ser Gly Thr Leu Ser Thr Gly Leu Ser Asn Phe Thr Val
                195                 200                 205 acg gac agt gcg tcc acg gcc tgg atc tct aca tcc aaa tta aag ctg      1332
Thr Asp Ser Ala Ser Thr Ala Trp Ile Ser Thr Ser Lys Leu Lys Leu
            210                 215                 220 aag gtg gat aag aat ccg ttc aaa ctg agc gtg tac aag ccg gac ggc      1380
Lys Val Asp Lys Asn Pro Phe Lys Leu Ser Val Tyr Lys Pro Asp Gly
        225                 230                 235 acg acg ctg atc gcg cgc cag tat gac agc acg gcc aac cgc aat ctc      1428
Thr Thr Leu Ile Ala Arg Gln Tyr Asp Ser Thr Ala Asn Arg Asn Leu
    240                 245                 250 gct tgg ctg acc aat ggc agc act gtc atc aat aaa atc gag gac cac      1476
Ala Trp Leu Thr Asn Gly Ser Thr Val Ile Asn Lys Ile Glu Asp His
255                 260                 265                 270 ttc tac tcg ccg gcg tcc gag gag ttt ttc ggc ttc ggg gag cgc tac      1524
Phe Tyr Ser Pro Ala Ser Glu Glu Phe Phe Gly Phe Gly Glu Arg Tyr
                275                 280                 285 aac aac ttc cgc aag cgc gga acc gac gtg gac acg tat gtc tac aat      1572
Asn Asn Phe Arg Lys Arg Gly Thr Asp Val Asp Thr Tyr Val Tyr Asn
            290                 295                 300 cag tac aaa aat caa aac gac cgc acc tat atg gca atc ccc ttc atg      1620
Gln Tyr Lys Asn Gln Asn Asp Arg Thr Tyr Met Ala Ile Pro Phe Met
        305                 310                 315 ctg aac agc agc ggg tac ggt atc ttc gta aac tcc acg tac tac tcc      1668
Leu Asn Ser Ser Gly Tyr Gly Ile Phe Val Asn Ser Thr Tyr Tyr Ser
    320                 325                 330 aaa ttc cgc ttg gca act gag cgc tcc gat atg tac agt ttt acg gcc      1716
Lys Phe Arg Leu Ala Thr Glu Arg Ser Asp Met Tyr Ser Phe Thr Ala
335                 340                 345                 350 gat acc ggg ggc agc gcc aat tcg acg ctg gat tac tac ttt att tac      1764
Asp Thr Gly Gly Ser Ala Asn Ser Thr Leu Asp Tyr Tyr Phe Ile Tyr
                355                 360                 365 ggc aat gac ttg aag ggc gtc gtc agc aat tat gcg aac atc aca ggc      1812
Gly Asn Asp Leu Lys Gly Val Val Ser Asn Tyr Ala Asn Ile Thr Gly
            370                 375                 380 aag ccg gct gct ctg ccc aaa tgg gcg ttt ggc ctc tgg atg tcg gcc      1860
Lys Pro Ala Ala Leu Pro Lys Trp Ala Phe Gly Leu Trp Met Ser Ala
        385                 390                 395 aat gag tgg gac cgg caa tcc aaa gta gcg act gcg atc aat aac gcc      1908
Asn Glu Trp Asp Arg Gln Ser Lys Val Ala Thr Ala Ile Asn Asn Ala
    400                 405                 410 aat acg aac aac atc ccg gcg acg gcc gtc gtg ctg gag cag tgg agt      1956
Asn Thr Asn Asn Ile Pro Ala Thr Ala Val Val Leu Glu Gln Trp Ser
415                 420                 425                 430 gac gag aat acg ttc tat atg ttc aac gat gcg cag tat acg gcc aaa      2004
```

```
                Asp Glu Asn Thr Phe Tyr Met Phe Asn Asp Ala Gln Tyr Thr Ala Lys
                                435                 440                 445 cct ggc ggc agc aca cac tcc tat acg gac tat atc ttc ccg gcg gcc              2052
Pro Gly Gly Ser Thr His Ser Tyr Thr Asp Tyr Ile Phe Pro Ala Ala
                450                 455                 460 ggc cgt tgg ccg aat ccg aag caa atg gcg gat aat gta cac agt aac              2100
Gly Arg Trp Pro Asn Pro Lys Gln Met Ala Asp Asn Val His Ser Asn
            465                 470                 475 ggg atg aag ctg gtg ctg tgg cag gtg ccg att cag aaa tgg acc gcc              2148
Gly Met Lys Leu Val Leu Trp Gln Val Pro Ile Gln Lys Trp Thr Ala
        480                 485                 490 gct cct cat ctg cag aag gac aac gac gaa agc tat atg atc gcg caa              2196
Ala Pro His Leu Gln Lys Asp Asn Asp Glu Ser Tyr Met Ile Ala Gln
495                 500                 505                 510 aat tat gcc gta ggc aac ggc agc gga ggc cag tac cgc atc cct agc              2244
Asn Tyr Ala Val Gly Asn Gly Ser Gly Gly Gln Tyr Arg Ile Pro Ser
                515                 520                 525 ggg caa tgg ttt gag aac agc ctg ctg ctg gac ttc acg aac ccg agc              2292
Gly Gln Trp Phe Glu Asn Ser Leu Leu Leu Asp Phe Thr Asn Pro Ser
            530                 535                 540 gcc aaa aac tgg tgg atg tcc aag cgc gcc tat ctg ttt gat ggc gtc              2340
Ala Lys Asn Trp Trp Met Ser Lys Arg Ala Tyr Leu Phe Asp Gly Val
        545                 550                 555 ggc atc gac ggg ttc aag acg gac gga ggg gag atg gtc tgg ggc cgc              2388
Gly Ile Asp Gly Phe Lys Thr Asp Gly Gly Glu Met Val Trp Gly Arg
        560                 565                 570 tgg aac acg ttc gcc aat ggc aaa aaa ggc gat gaa atg cgc aac cag              2436
Trp Asn Thr Phe Ala Asn Gly Lys Lys Gly Asp Glu Met Arg Asn Gln
575                 580                 585                 590 tac ccg aac gat tac gtg aag gcc tac aac gaa tat gcg cgc tcg aag              2484
Tyr Pro Asn Asp Tyr Val Lys Ala Tyr Asn Glu Tyr Ala Arg Ser Lys
                595                 600                 605 aaa agc gat gcc gtc agc ttc agc cgt tcg ggc acg caa ggg gcg caa              2532
Lys Ser Asp Ala Val Ser Phe Ser Arg Ser Gly Thr Gln Gly Ala Gln
            610                 615                 620 gcg aat cag atc ttc tgg tcc ggt gac cag gaa tcg acg ttc ggt gcc              2580
Ala Asn Gln Ile Phe Trp Ser Gly Asp Gln Glu Ser Thr Phe Gly Ala
        625                 630                 635 ttc cag caa gcc gtc cag gcg gga ctg acc gca ggc ttg tcc ggc gtt              2628
Phe Gln Gln Ala Val Gln Ala Gly Leu Thr Ala Gly Leu Ser Gly Val
        640                 645                 650 ccg tat tgg agc tgg gac ttg gct gga ttc acc ggc gct tat ccg tcg              2676
Pro Tyr Trp Ser Trp Asp Leu Ala Gly Phe Thr Gly Ala Tyr Pro Ser
655                 660                 665                 670 gcc gag cta tat aaa cgc gcg acg gca atg tcg gca ttt gcc ccg att              2724
Ala Glu Leu Tyr Lys Arg Ala Thr Ala Met Ser Ala Phe Ala Pro Ile
                675                 680                 685 atg cag ttc cac tcc gaa gcc aac ggc agt tcc ggc atc aat gag gag              2772
Met Gln Phe His Ser Glu Ala Asn Gly Ser Ser Gly Ile Asn Glu Glu
            690                 695                 700 cgg tcc ccg tgg aat gct cag gcc cgg act ggc gac aac acg atc atc              2820
Arg Ser Pro Trp Asn Ala Gln Ala Arg Thr Gly Asp Asn Thr Ile Ile
        705                 710                 715 agc cat ttt gcc aag tat acg aac acc cgg atg aac ctg ctt cct tat              2868
Ser His Phe Ala Lys Tyr Thr Asn Thr Arg Met Asn Leu Leu Pro Tyr
        720                 725                 730 att tac agc gag gct aaa gca gca agc gat act ggc gtg ccg atg atg              2916
Ile Tyr Ser Glu Ala Lys Ala Ala Ser Asp Thr Gly Val Pro Met Met
735                 740                 745                 750
```

```
cgc gcg atg gcg ctg gag tat ccg agc gat acc cag acg tac gga ttg        2964
Arg Ala Met Ala Leu Glu Tyr Pro Ser Asp Thr Gln Thr Tyr Gly Leu
                755                 760                 765 acg cag cag tac atg ttc ggc ggc agc ctg ctg gtg gcg cct gtc ttg        3012
Thr Gln Gln Tyr Met Phe Gly Gly Ser Leu Leu Val Ala Pro Val Leu
            770                 775                 780 aac caa ggc gag acg aat aag aat atc tac ctt ccg caa gga gat tgg        3060
Asn Gln Gly Glu Thr Asn Lys Asn Ile Tyr Leu Pro Gln Gly Asp Trp
        785                 790                 795 atc gac ttc tgg ttc ggc gcg cag cgt ccg ggc ggg cga acg atc agc        3108
Ile Asp Phe Trp Phe Gly Ala Gln Arg Pro Gly Gly Arg Thr Ile Ser
    800                 805                 810 tac tac gcg ggc gtg gac gat ctt ccc gtc ttc gtg aag tcc ggc agc        3156
Tyr Tyr Ala Gly Val Asp Asp Leu Pro Val Phe Val Lys Ser Gly Ser
815                 820                 825                 830 atc ctg ccg atg aat ctg aac ggg cag tat cag gtt ggc ggc acg atc        3204
Ile Leu Pro Met Asn Leu Asn Gly Gln Tyr Gln Val Gly Gly Thr Ile
                835                 840                 845 ggc aac agc ttg acc gcc tac aac aac ctg acg ttc cgg att tat cca        3252
Gly Asn Ser Leu Thr Ala Tyr Asn Asn Leu Thr Phe Arg Ile Tyr Pro
            850                 855                 860 ctg ggt acg acg acg tac agc tgg aat gat gac atc ggc ggc tcg gtg        3300
Leu Gly Thr Thr Thr Tyr Ser Trp Asn Asp Asp Ile Gly Gly Ser Val
        865                 870                 875 aag acg att acg tcg aca gag cag tat gga ctg aat aaa gag acg gtg        3348
Lys Thr Ile Thr Ser Thr Glu Gln Tyr Gly Leu Asn Lys Glu Thr Val
    880                 885                 890 acg ctt ccg gcg atc aac tcg gcg aag acg ctc cag gtg ttc acg acc        3396
Thr Leu Pro Ala Ile Asn Ser Ala Lys Thr Leu Gln Val Phe Thr Thr
895                 900                 905                 910 aag ccg tcg tcg gtg acg ctg ggc ggc acg gcc ctc acc gcg cat agc        3444
Lys Pro Ser Ser Val Thr Leu Gly Gly Thr Ala Leu Thr Ala His Ser
                915                 920                 925 aca tta agc gca ttg atc ggc gct tcc tcc ggc tgg tat tac gat acg        3492
Thr Leu Ser Ala Leu Ile Gly Ala Ser Ser Gly Trp Tyr Tyr Asp Thr
            930                 935                 940 gtg caa aag ctc gcc tat gtg aag ctc ggc gcc agc tca tcg gcg caa        3540
Val Gln Lys Leu Ala Tyr Val Lys Leu Gly Ala Ser Ser Ser Ala Gln
        945                 950                 955 acc gtc gtg ctt gac ggc gtc aac aag gtc gag tat gag gct gag ttc        3588
Thr Val Val Leu Asp Gly Val Asn Lys Val Glu Tyr Glu Ala Glu Phe
    960                 965                 970 ggc aca ctt acc ggc gtc acg acc aat acg aat cat gcc ggc tat atg        3636
Gly Thr Leu Thr Gly Val Thr Thr Asn Thr Asn His Ala Gly Tyr Met
975                 980                 985                 990 ggt acc ggc ttt gtc gac ggc ttc gat gcg gca ggc gat gca gtg acc        3684
Gly Thr Gly Phe Val Asp Gly Phe Asp Ala Ala Gly Asp Ala Val Thr
                995                 1000                1005 ttc gac gta tcc gtc aaa gcg gcc ggc acg tat gcg ctc aag gtc cgg        3732
Phe Asp Val Ser Val Lys Ala Ala Gly Thr Tyr Ala Leu Lys Val Arg
            1010                1015                1020 tac gct tcc gct ggt ggc aac gct tca cgc gct atc tat gtc aac aac        3780
Tyr Ala Ser Ala Gly Gly Asn Ala Ser Arg Ala Ile Tyr Val Asn Asn
        1025                1030                1035 gcc aag gtg acc gat ctg gcg ctt ccg gca acg gcc aac tgg gac acc        3828
Ala Lys Val Thr Asp Leu Ala Leu Pro Ala Thr Ala Asn Trp Asp Thr
    1040                1045                1050 tgg ggg acg gca acc gtc aac gta gcc tta aac gcc ggc tac aac tcg        3876
Trp Gly Thr Ala Thr Val Asn Val Ala Leu Asn Ala Gly Tyr Asn Ser
1055                1060                1065                1070
```

-continued

```
atc aag gtc agc tac gac aac acc aat acg ctc ggc att aat ctc gat      3924
Ile Lys Val Ser Tyr Asp Asn Thr Asn Thr Leu Gly Ile Asn Leu Asp
            1075                1080                1085 aac att gcg atc gtg gag cat tga                                      3948
Asn Ile Ala Ile Val Glu His
            1090 cagcaggaat cttcgcgagg aatgagttag cgaagagttc atgcaggcag agggttacc     4008
cataattgta aagcccggcg cagccaggca ccaagtatgc ccgggagggc cgccggccct    4068
cccctttattt caatgatgaa aggcggcatc gatatgggtc tatggaacaa acgagtcact   4128
cgcatcctct ccgtactcgc agcaagcgcg ctgatcggct ctaccgtacc ttctctagcg    4188
ccacctcccg ctcaagccca tgtgagcgcg ctgggcaacc tgctttcctc ggcggtgacc    4248
ggggatacgc tcacgctgac gatcgataac ggcgcggaac cgaatgacga tattctagtt    4308
ctgcaagcag tccagaacgg tattctgaag gtggactacc ggccgaacgg tgtagctcca    4368
agcgcggata cgccgatgct ggatcccaat aaaacctggc cgtccatagg cgccgttatc    4428
aatacagcct ctaatccgat gacgatcaca acgccggcga tgaagattga gattgccaaa    4488
aatccggtgc gcctgaccgt gaaaaaaccg gacggcaccg ctctgttatg ggaaccccccg   4548
accggcggcg tcttctcgga cggcgtccgt ttcttgcacg ggacgggcga caatatgtac    4608
ggcatccgca gcttcaatgc ttttgacagc ggcggggatc tgctgcgcaa cagctccacc    4668
caagccgccc gtgcaggcga ccagggcaac tccggcggcc cgctgatctg agcacagcc     4728
gggtacgggg tgctcgttga cagcgacggt gggtatccgt tcacgacga ggctaccggc     4788
aagctggagt tctattacgg cggcacgcct ccggaaggcc ggcgctatac gaagcaggat    4848
gtggagtact acatcatgct cggcacgccg aaagagatca tgtccggcgt cggggaaatt    4908
acgggcaaac cgccgatgct gcccaagtgg tccctgggct ttatgaactt cgagtgggat    4968
ctgaatgaag ctgagctc                                                  4986
```

<210> SEQ ID NO 17
<211> LENGTH: 17
<212> TYPE: PRT
<213> ORGANISM: Artificial
<220> FEATURE:
<223> OTHER INFORMATION: synthetic

<400> SEQUENCE: 17

Ala Ala Tyr Thr Gly Gly Thr Gly Gly Ala Thr Gly Trp Ser Asn Ala
1               5                   10                  15

Ala

<210> SEQ ID NO 18
<211> LENGTH: 17
<212> TYPE: PRT
<213> ORGANISM: Artificial
<220> FEATURE:
<223> OTHER INFORMATION: synthetic

<400> SEQUENCE: 18

Gly Thr Asn Thr Thr Tyr Ala Ala Tyr Cys Ala Arg Thr Ala Tyr Ala
1               5                   10                  15

Ala

<210> SEQ ID NO 19
<211> LENGTH: 23
<212> TYPE: PRT

```
-continued

<213> ORGANISM: Artificial
<220> FEATURE:
<223> OTHER INFORMATION: synthetic

<400> SEQUENCE: 19

Gly Ala Tyr Thr Gly Gly Ala Thr His Gly Ala Tyr Thr Thr Tyr Thr
1               5                   10                  15

Gly Gly Thr Thr Tyr Gly Gly
            20
```

POLYPEPTIDE HAVING α-ISOMALTOSYL-TRANSFERASE ACTIVITY

FIELD OF THE INVENTION

The present invention relates to polypeptides which forming a cyclic tetrasaccharide having the structure of cyclo{6)-α-D-glucopyranosyl-(1 3)-α-D-glucopyranosyl-(1 6)-α-D-glucopyranosyl-(1 3)-α-D-glucopyranosyl-(1 } from a saccharide with a glucose polymerization degree of 3 or higher and bearing both the α-1,6 glucosidic linkage as a linkage at the non-reducing end and the α-1,4 glucosidic linkage other than the linkage at the non-reducing end, and which comprise an amino acid sequence of either SEQ ID NO:1 or SEQ ID NO:2, or the amino acid sequence having deletion, replacement, or addition of one or more amino acid residues of SEQ ID NO:1 or SEQ ID NO:2; and to uses thereof. More particularly, the present invention relates to polypeptides which form a cyclic tetrasaccharide having a structure of cyclo{6)-α-D-glucopyranosyl-(1 3)-α-D-glucopyranosyl-(1 6)-α-D-glucopyranosyl-(1 3)-α-D-glucopyranosyl-(1} from a saccharide with a glucose polymerization degree of 3 or higher and bearing both the α-1,6 glucosidic linkage as a linkage at the non-reducing end and the α-1,4 glucosidic linkage other than the linkage at the non-reducing end, and which comprise the amino acid sequence of either SEQ ID NO:1 or SEQ ID NO:2, or the amino acid sequence having deletion, replacement or addition of one or more amino acid residues of SEQ ID NO:1 or SEQ ID NO:2, to a DNA encoding the amino acid sequence, to a replicable recombinant DNA which comprises a DNA encoding the polypeptide and an autonomously replicable vector, to transformants which are constructed by introducing the recombinant DNAs into appropriate hosts, to a process for preparing the polypeptides, to the cyclic tetrasaccharide described above, and to uses thereof.

BACKGROUND ART

There have been known several saccharides which are composed of glucose molecules as constituents, for example, partial starch hydrolyzates, produced from starches as materials, including amyloses, amylodextrins, maltodextrins, maltooligosaccharides, and isomaltooligosaccharides. Also, these saccharides are known to have usually non-reducing and reducing groups at their molecular ends and exhibit reducibility. Usually, partial starch hydrolyzates, which have a strong reducing power on a dry solid basis, are known to have properties of a relatively low molecular weight and viscosity, a relatively strong sweetness and reactivity, easy reactivity with amino group-containing substances such as amino acids and proteins by amino carbonyl reaction that may induce browning and unpleasant smell, and easily cause deterioration. Therefore, methods for decreasing or eliminating the reducing power of reducing saccharides without altering glucose residues have been required for a long time. For example, as disclosed in "Journal of American Chemical Society, Vol. 71, 353–358 (1949)", it was reported that methods for forming α-, β- or γ-cyclodextrins that are composed of 6, 7 or 8 glucose molecules linked together via the α-1,4 glucosidic linkage by contacting "macerans amylase" with starches. Nowadays, these cyclodextrins are produced on an industrial scale and are used in diversified fields using their inherent properties such as non-reducibility, tasteless, and inclusion abilities. As disclosed, for example, in Japanese Patent Kokai Nos. 143,876/95 and 213,283 applied for by the same applicant of the present invention, it is known a method for producing trehalose, composed of two glucose molecules linked together via the α,α-linkage, by contacting a non-reducing saccharide-forming enzyme and a trehalose-releasing enzyme with partial starch hydrolyzates such as maltooligosaccharides. At present, trehalose has been industrially produced from starches and used in different fields by using its advantageous non-reducibility, mild- and high quality-sweetness. As described above, trehalose having a glucose polymerization degree of 2, and α-, β- and γ-cyclodextrin having a glucose polymerization degree of 6, 7 and 8, are produced on an industrial scale and used in view of their advantageous properties, however, the types of non- or low-reducing saccharides are limited, so that more diversified saccharides other than these saccharide are greatly required.

Recently, a novel cyclic tetrasaccharide constructed by glucoses has been disclosed. For example, "European Journal of Biochemistry, Vol. 226, 641–648 (1994)" shows that a cyclic tetrasaccharide which has a structure of cyclo{→6)-α-D-glucopyranosyl-(1→3)-α-D-glucopyranosyl-(1→6)-α-D-glucopyranosyl-(1→3)-α-D-glucopyranosyl-(1→} (hereinafter, called "cyclotetrasaccharide" in the present specification, unless specified otherwise.) is formed by contacting a hydrolyzing enzyme, alternanase, with alternan linked with glucose molecules via the alternating α-1,3 and α-1,6 bonds, followed by crystallization under the coexistence of methanol. Since cyclotetrasaccharide is a sugar having a cyclic structure and has no reducing power, it is expected that the saccharide shows no amino-carbonyl reactivity, and is useful to stabilize volatile organic compounds by its inclusion ability, and to be processed without any apprehension of browning and deterioration. However, it has been difficult to obtain alternan as a material and alternanase as an enzyme for preparing cyclotetrasaccharide. In addition, it has been substantially difficult to obtain a microorganism producing the enzyme.

Under these circumstances, the present inventors made every effort to study on a novel process for industrial production of cyclotetrasaccharide. As disclosed in PTC/JP01/04276, the present inventors found microorganisms of the genera *Bacillus* and *Arthrobacter* which produce an absolutely novel and ever unknown enzyme, α-isomaltosyl-transferring enzyme for forming cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end. They found and disclosed in PCT/JP01/06412 that these microorganisms also produced another novel enzyme, α-isomaltosylglucosaccharide-forming enzyme which forms a saccharide with a glucose polymerization degree of 3 or higher and bearing both the α-1,6 glucosidic linkage as a linkage at the non-reducing end and the α-1,4 glucosidic linkage other than the linkage at the non-reducing end from saccharides with a glucose polymerization degree of 2 or higher. Furthermore, the present inventors found that cyclotetrasaccharide can be obtained from starchy saccharides with a glucose polymerization degree of 3 or higher by using α-isomaltosyl-transferring enzyme and α-isomaltosylglucosaccharide-forming enzyme. However, since the productivities of α-isomaltosyl-transferring enzyme of these microorganisms were not enough, a large-scale cultivation of these microorganisms is substantially difficult for industrial scale production of cyclotetrasaccharide.

Now, it has been revealed that the entity of the enzyme is a polypeptide, and the enzymatic activity is controlled by its amino acid sequence, as well as a DNA that encodes the amino acid sequence. Therefore, if a gene which encodes the polypeptide will be isolated, and if its nucleotide sequence will be determined, it will be relatively easy to prepare the desired amount of the polypeptide by a method which comprises the steps of constructing a recombinant DNA containing a gene which encodes the polypeptide, introducing the recombinant DNA into host-cells of microorganisms, animals or plants, and culturing the obtained transformants.

Under these circumstances, required are the isolation of a gene encoding a polypeptide as the entity of α-isomaltosyl-transferring enzyme, sequencing of the nucleotide sequence, and stable preparation of the polypeptide in large scale and at a relatively low cost.

DISCLOSURE OF INVENTION

The first object of the present invention is to establish a polypeptide which has α-isomaltosyl-transferring enzymatic activity which catalyzes the formation of cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end (hereinafter, the polypeptide described above may be abbreviated as "the polypeptide of the present invention").

The second object of the present invention is to provide a DNA encoding the polypeptide of the present invention.

The third object of the present invention is to provide a replicable recombinant DNA comprising the DNA.

The fourth object of the present invention is to provide a transformant transformed by the recombinant DNA.

The fifth object of the present invention is to provide a process for producing the polypeptide of the present invention by using the transformant.

The sixth object of the present invention is to provide a process for forming cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end by using the polypeptide of the present invention.

The seventh object of the present invention is to provide cyclotetrasaccharide, which can be obtained using the polypeptide of the present invention, and to its uses.

The present invention solves the first object by providing a polypeptide which forms cyclotetrasaccharide having a structure of cyclo{→6}-α-D-glucopyranosyl-(1→3)-α-D-glucopyranosyl-(1→6)-α-D-glucopyranosyl-(1→3)-α-D-glucopyranosyl-(1→) from a saccharide with a glucose polymerization degree of 3 or higher and bearing both the α-1,6 glucosidic linkage as a linkage at the non-reducing end and the α-1,4 glucosidic linkage other than the linkage at the non-reducing end, and a polypeptide comprising the amino acid sequence of either SEQ ID NO:1 or SEQ ID NO:2, or the amino acid sequence having deletion, replacement or insertion of one or more amino acids of SEQ ID NO:1 or SEQ ID NO:2

The present invention solves the second object described above by providing a DNA encoding the polypeptide.

The present invention solves the third object described above by providing a replicable recombinant DNA which comprises a DNA encoding the polypeptide and an autonomously replicable vector.

The present invention solves the fourth object described above by providing a transformant constructed by introducing the recombinant DNA into an appropriate host.

The present invention solves the fifth object described above by providing a process for preparing the polypeptide, which comprises the steps of culturing the transformant constructed by introducing a replicable recombinant DNA, which contains a DNA encoding the polypeptide and an autonomously replicable vector, into appropriate hosts, and collecting the polypeptide from the resultant culture.

The present invention solves the sixth object described above by providing a process for producing cyclotetrasaccharide, which comprises a step of forming cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end using the polypeptide of the present invention.

The present invention solves the seventh object described above by producing cyclotetrasaccharide which is obtained by using the polypeptide of the present invention, and providing foods, cosmetics and pharmaceuticals which comprise cyclotetrasaccharide or saccharide compositions containing cyclotetrasaccharide.

BRIEF DESCRIPTION OF DRAWINGS

FIG. 1 shows the optimum temperature of a polypeptide having α-isomaltosyl-transferring enzyme activity from a microorganism of the species *Bacillus globisporus* C11 strain.

FIG. 2 shows the optimum pH of a polypeptide having α-isomaltosyl-transferring enzyme activity from a microorganism of the species *Bacillus globisporus* C11 strain.

FIG. 3 shows the thermal stability of a polypeptide having α-isomaltosyl-transferring enzyme activity from a microorganism of the species *Bacillus globisporus* C11 strain.

FIG. 4 shows the pH stability of a polypeptide having α-isomaltosyl-transferring enzyme activity from a microorganism of the species *Bacillus globisporus* C11 strain.

FIG. 5 shows the optimum temperature of a polypeptide having α-isomaltosyl-transferring enzyme activity from a microorganism of the species *Bacillus globisporus* N75 strain.

FIG. 6 shows the optimum pH of a polypeptide having α-isomaltosyl-transferring enzyme activity from a microorganism of the species *Bacillus globisporus* N75 strain.

BEST MODE FOR CARRYING OUT OF THE INVENTION

Figure 7:
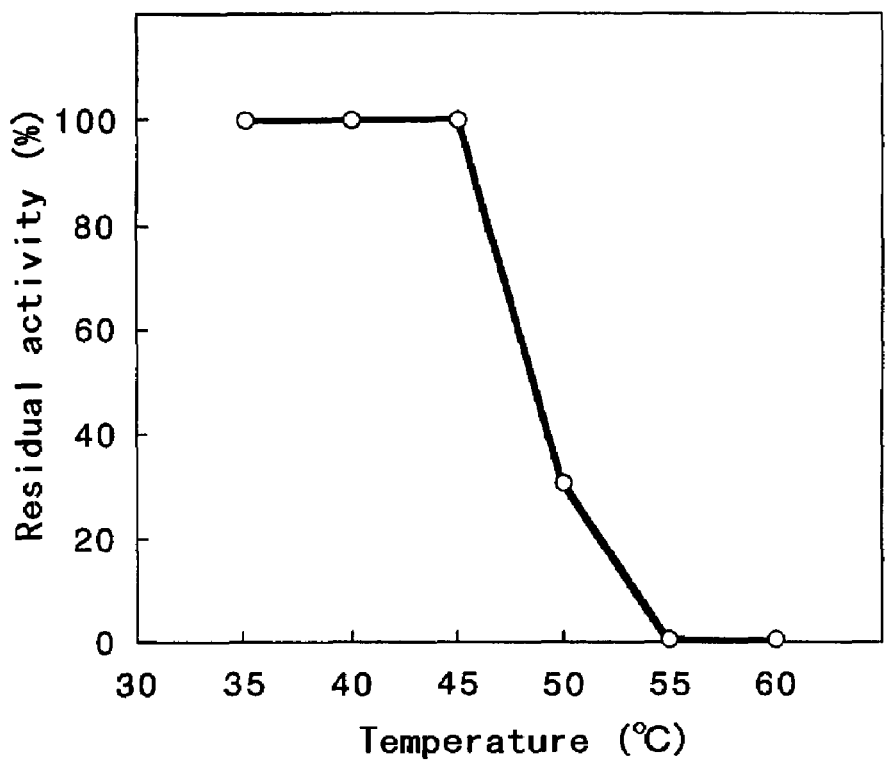
FIG. 7 shows the thermal stability of a polypeptide having α-isomaltosyl-transferring enzyme activity from a microorganism of the species *Bacillus globisporus* N75 strain.

The present invention was made based on the finding of absolutely novel and ever unknown enzymes which catalyze the formation of cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end. These enzymes can be obtained as polypeptides from the culture of novel microorganisms, strain C11 and strain N75, isolated from soils by the present inventors. The present inventors named the strain C11 "*Bacillus globisporus* C11", and deposited it on Apr. 25, 2000, in International Patent Organism Depositary National Institute of Advanced Industrial Science and Technology Tsukuba Central 6, 1-1, Higashi 1-Chome Tsukuba-shi, Ibaraki-ken, 305-8566, Japan. The deposition of the microorganism was accepted under the accession number of FERM BP-7144. The present inventors also named the strain N75 "*Bacillus globisporus* N75", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305-8566, Japan. The deposition of the microorganism was accepted under the accession number of FERM BP-7591. As disclosed by the present inventors in PTC/JP01/06412, the strains C11 and N75 also produce α-isomalosylglucosaccharide-forming enzyme which form a saccharide with a glucose polymerization degree of 3 or higher and bearing both the α-1,6 glucosidic linkage as a linkage at the non-reducing end and the α-1,4 glucosidic linkage other than the linkage at the non-reducing end from maltodextrin with a glucose polymerization degree of 2 or higher.

The following are the bacteriological properties of the strains C11 and N75.

<*Bacillus globisporus* C11>

<A. Morphology>
Characteristic of cells when incubated at 27 ° C. of nutrient broth agar;
Existing usually in a rod shape of 0.5–1.0×1.5–5 μm,
Exhibiting no polymorphism,
Possessing motility,
Forming spherical spores at an intracellular end
And swelled sporangia, and
Gram stain, positive;

<B. Cultural Property>
(1) Characteristics of colonies formed when incubated at 27° C. in nutrient broth agar plate;
Shape: Circular colony having a diameter of 1–2 mm after 2 days incubation
Rim: Entire
Projection: Hemispherical shape
Gloss: Dull
Surface: Smooth
Color: Opaque and pale yellow
(2) Characteristics of colony formed when incubated at 27° C. in nutrient broth agar slant;
Growth: Roughly medium
Shape: Radiative
(3) Characteristics of colony formed when stub cultured at 27° C. in nutrient broth agar plate;
Liquefying the agar plate.

<C. Physiological Properties>
(1) VP-test: Negative
(2) Indole formation: Negative
(3) Gas formation from nitric acid: Positive
(4) Hydrolysis of starch: Positive
(5) Formation of pigment: Forming no soluble pigment
(6) Urease: Positive
(7) Oxidase: Positive
(8) Catalase: Positive
(9) Growth conditions: Growing at a pH of 5.5–9.0 and a temperature of 10–35° C.
(10) Oxygen requirement: Aerobic
(11) Utilization of carbon source and acid formation

| Carbon source | Utilization | Acid formation |
| --- | --- | --- |
| D-Glucose | + | + |
| Glycerol | + | + |
| Sucrose | + | + |
| Lactose | + | + |

Note:
The symbol "+" means yes or positive.

(14) Mol% of guanine (G) plus cytosine (C) of DNA: 39%

<*Bacillus globisporus* N75>

<A. Morphology>
(1) Characteristic of cells when incubated at 27° C. of nutrient broth agar;
Existing usually in a rod shape of 0.5–1.0×1.5–5 μm,
Exhibiting no polymorphism,
Possessing motility,
Forming spherical spores at an intracellular end
And swelled sporangia, and
Gram stain, positive;

<B. Cultural Property>
(1) Characteristics of colonies formed when incubated at 27° C. in nutrient broth agar plate;
Shape: Circular colony having a diameter of 1–2 mm after 2 days incubation
Rim: Entire
Projection: Hemispherical shape
Gloss: Dull
Surface: Smooth
Color: Opaque and pale yellow
(2) Characteristics of colony formed when incubated at 27° C. in nutrient broth agar slant;
Growth: Roughly medium
Shape: Radiative
(3) Characteristics of colony formed when stub cultured at 27° C. in nutrient broth agar plate;
Liquefying the agar plate.

<C. Physiological Properties>
(1) VP-test: Negative
(2) Indole formation: Negative
(3) Gas formation from nitric acid: Positive
(4) Hydrolysis of starch: Positive
(5) Formation of pigment: Forming no soluble pigment
(6) Urease: Positive
(7) Oxidase: Positive
(8) Catalase: Positive
(9) Growth conditions: Growing at a pH of 5.5–9.0 and a temperature of 10–35° C.
(10) Oxygen requirement: Aerobic
(11) Utilization of carbon source and acid formation

| Carbon source | Utilization | Acid formation |
|---|---|---|
| D-Glucose | + | + |
| Glycerol | + | + |
| Sucrose | + | + |
| Lactose | + | + |

Note:
The symbol "+" means yes or positive.

(12) Mol% of guanine (G) plus cytosine (C) of DNA: 40%

The present inventors purified and characterized the α-isomaltosyl-transferring enzyme which is obtainable from the culture of *Bacillus globisporus* C11 (FERM BP-7144) or *Bacillus globisporus* N75 (FERM BP-7591). As a result, it was revealed that the enzyme has an activity to form cyclotetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide with a glucose polymerization degree of 3 or higher and bearing both the α-1,6 glucosidic linkage as a linkage at the non-reducing end and the α-1,4 glucosidic linkage other than the linkage at the non-reducing end, and is polypeptide comprising the amino acid sequences of SEQ ID NO:1 or SEQ ID NO:2. In addition, the physicochemical properties of the polypeptides are as follows;

(1) Molecular weight
   Having a molecular weight of about 82,000 to about 132,000 daltons when determined on SDS-PAGE;
(2) Optimum temperature
   Having an optimum temperature of about 50° C. when incubated at a pH of 6.0 for 30 min;
(3) Optimum pH
   Having an optimum pH of about 5.5 to 6.0 when incubated at 35° C. for 30 min;
(4) Thermal stability
   Having a thermostable region at temperatures of about 45° C. or lower when incubated at a pH of 6.0 for 60 min;
(5) pH Stability
   Having a stable pH region at about 4.5 to 10.0 when incubated at 4° C. for 24 hours;

The following experiments explain the physicochemical properties of the polypeptide having an α-isomaltosyl-transferring enzymatic activity of the present invention.

Experiment 1

Preparation of a Polypeptide from *Bacillus globisporus*

Experiment 1-1

Preparation of Crude Polypeptide

A liquid culture medium consisting 4% (w/v) of "PINE-DEX #4", a partial starchhydrolyzate, 1.8% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 min, cooled and seeded with *Bacillus globisporus* C11 strain, FERM BP-7144, followed by culturing under rotary-shaking conditions at 27° C. and 230 rpm for 48 hours for a seed culture.

About 20 L of a fresh preparation of the same liquid culture medium as used in the above seed culture were placed in a 30 L fermentor, sterilized by heating, and then cooled to 27° C. and inoculated with 1% (v/v) of the seed culture, followed by culturing at 27° C. and pH 6.0 to 8.0 for 48 hours under aeration-agitation conditions. After the completion of the culture, about 1.8 units/ml of α-isomaltosyl-transferring enzyme and about 0.55 unit/ml of α-isomaltosylglucosaccharide-forming enzyme were detected in the resulting culture by measuring enzyme activities. About 18 L of supernatant obtained by centrifugation at 10,000 rpm for 30 min had about 1.7units/ml of α-isomaltosyl-transferring enzyme activity, i.e., a total activity of about 30,400 units; and 0.51 unit of α-isomaltosylglucosaccharide-forming enzyme activity, i.e., a total enzymatic activity of about 9,180 units. It was revealed that these enzymes were secretion polypeptides secreted in the culture.

The activity of α-isomaltosyl-transferring enzyme was measured by the following assay: A substrate solution was prepared by dissolving panose in 100 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 30 min. After stopping the reaction by boiling for 10 min, the amount of glucose formed in the reaction mixture was determined by the glucose oxidase-peroxidase method. One unit of α-isomaltosyl-transferring activity was defined as the amount of the enzyme that forms one µmole of glucose per minute under the above conditions.

The Activity of α-isomaltosylglucosaccharide-forming enzyme was measured by the following assay: A substrate solution was prepared by dissolving maltotriose in 100 mM acetate buffer (pH 6.0) to give a concentration of 2% (w/v). A reaction mixture was prepared by mixing 0.5 ml of the substrate solution and 0.5 ml of an enzyme solution, and incubated at 35° C. for 60 min. After stopping the reaction by boiling for 10 min, the amount of glucose formed in the reaction mixture was determined by high-performance liquid chromatography (HPLC). One unit of α-isomaltosylglucosaccharide-forming activity was defined as the amount of the enzyme that forms one µmole of maltose per minute under the above conditions. HPLC was carried out using- "SHODEX KS-801 column", Showa Denko K.K., Tokyo, Japan, at a column temperature of 60° C. and a flow rate of 0.5 ml/min of water, and using "RI-8012", a differential refractometer commercialized by Tosho Corporation, Tokyo, Japan.

About 18 L of the culture supernatant described above were salted out with 80% saturated ammonium sulfate solution and allowed to stand at 4° C. for 24 hours, and the formed precipitates were collected by centrifugation at 10,000 rpm for 30 min, dissolved in 10 mM sodium phosphate buffer (pH 7.5), and dialyzed against the same buffer to obtain about 416 ml of a crude enzyme solution. The crude enzyme solution had about 28,000 units of α-isomaltosyl-transferring enzyme and 8,440 units of α-isomaltosylglucosaccharide-forming enzyme. The crude enzyme solution was subjected to ion-exchange column chromatography using "SEPABEADS FP-DA13" gel, an ion-exchange resin commercialized by Mitsubishi Chemical Industries, Ltd., Tokyo, Japan. Both α-isomaltosyl-transferring enzyme and α-isomaltosylglucosaccharide-forming enzyme were eluted as non-adsorbed fractions without adsorbing on "SEPABEADS FP-DA13" gel. The non-adsorbed fraction was collected and dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Corp., Div. Amersham International, Arlington heights, Ill., USA. Enzymatically active components adsorbed on "SEPHACRY HR S-200" gel and, when sequentially eluted with a linear gradient decreasing from 1 M to 0 M of ammonium sulfate and a linear gradient increasing from 0 mM to 100 mM of maltotetraose, the α-isomaltosyl-transferring enzyme and the α-isomaltosylglucosaccharide-forming enzyme were separately eluted, i.e., the former was eluted with a linear gradient of ammonium sulfate at about 0 M and the latter was eluted with a linear gradient of maltotetraose at about 30 mM. Thus, fractions with the α-isomaltosyl-transferring enzyme activity and those with the α-isomaltosylglucosaccharide-forming enzyme activity were separately collected as crude polypeptides of α-isomaltosyl-transferring enzyme and α-isomaltosylglucosaccharide-forming enzyme. Further, the polypeptides having an α-isomaltosyl-transferring enzyme activity or α-isomaltosylglucosaccharide-forming enzyme activity were respectively purified and prepared by the methods described in the below.

Experiment 1-2

Purification of a Polypeptide having an α-Isomaltosyl-Transferring Enzyme Acticity The crude polypeptide having an α-Isomaltosyl-transferring enzyme activity obtained in Experiment1-1 was dialyzed against 10 mM sodium phosphate buffer (pH 7.0) with 1 M ammonium sulfate. The dialyzed solution was centrifuged to remove impurities, and subjected to hydrophobic column chromatography using 350 ml of "BUTYL-TOYOPEARL 650M" gel, a hydrophobic gel commercialized by Tosho Corporation, Tokyo, Japan. The enzyme adsorbed on "BUTYL-TOYOPEARL 650M" gel and, when eluted with a linear gradient decreasing from 1 M to 0M of ammonium sulfate, the enzymatically active fractions were eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by affinity chromatography using "SEPHACRYL HR S-200" gel. The amount of enzyme activity, specific activity and yield of the α-isomaltosyl-transferring enzyme in each purification step are in Table 1.

TABLE 1

| Purification step | Enzyme* activity (unit) | Specific activity of enzyme* (unit/mg protein) | Yield (%) |
|---|---|---|---|
| Culture supernatant | 30,400 | 0.45 | 100 |
| Dialyzed solution after salting out with ammonium sulfate | 28,000 | 1.98 | 92.1 |
| Elute from ion-exchange column chromatography | 21,800 | 3.56 | 71.7 |
| Elute from affinity column chromatography | 13,700 | 21.9 | 45.1 |
| Elute from hydrophobic column chromatography | 10,300 | 23.4 | 33.9 |
| Elute from affinity column chromatography | 5,510 | 29.6 | 18.1 |

Note:
The symbol "*" means the α-isomaltosyl-transferring enzyme of the present invention.

The finally purified α-Isomaltosyl-transferring enzyme specimen was assayed for purify on gel electrophoresis using a 7.5% (w/v) polyacrylamide gel and detected on the gel as a single protein band, i.e., a high purity specimen.

Experiment 1-3

Purification of α-Isomaltosylglucosaccharide-Forming Enzyme

The crude polypeptide having α-isomaltosylglucosaccharide-forming enzyme activity, obtained in Experiment 1-1, was dialyzed against 10 mM sodium phosphate buffer (pH 7.0) with 1 M ammonium sulfate. The dialyzed solution was centrifuged to remove impurities, and subjected 15 to hydrophobic column chromatography using 350 ml of "BUTYL-TOYOPEARL 650M" gel, a hydrophobic gel commercialized by Tosho Corporation, Tokyo, Japan. The enzyme was adsorbed on "BUTYL-TOYOPEARL 650M" gel and, when eluted with a linear gradient decreasing from 1 M to 0M of ammonium sulfate, the enzymatic activity was eluted with a linear gradient of ammonium sulfate at about 0.3 M, and fractions with the enzyme activity 5 was collected. The collected solution was dialyzed against 10 mM sodium phosphate buffer (pH 7.0) with 1 M ammonium sulfate, and the dialyzed solution was centrifuged to remove impurities, and purified by affinity chromatography using "SEPHACRYL HR S-200" gel. The amount of enzyme activity, specific activity and yield of the α-isomaltosylglucosaccharide-forming enzyme in each purification step are shown in Table 2.

TABLE 2

| Purification step | Enzyme* activity (unit) | Specific activity of enzyme* (unit/mg protein) | Yield (%) |
|---|---|---|---|
| Culture supernatant | 9,180 | 0.14 | 100 |
| Dialyzed solution after salting out with ammonium sulfate | 8,440 | 0.60 | 91.9 |
| Elute from ion-exchange column chromatography | 6,620 | 1.08 | 72.1 |
| Elute from affinity column chromatography | 4,130 | 8.83 | 45.0 |
| Elute from hydrophobic column chromatography | 3,310 | 11.0 | 36.1 |
| Elute from affinity column chromatography | 2,000 | 13.4 | 21.8 |

Note:
The symbol "*" means the α-isomaltosylglucosaccharide-forming enzyme.

The finally purified α-isomaltosylglucosaccharide-forming enzyme specimen was assayed for purify on gel electrophoresis using a 7.5% (w/v) polyacrylamide gel and detected on the gel as a single protein band, i.e., a high purity specimen.

Experiment 2

Physicochemical Properties of Polypeptide having an α-Isomaltosyl-Transferring Enzyme Activity Experiment 2-1

Action

An aqueous solution containing 10 mM of glucose, 6-O-α-glucosylglucose (isomaltose), $6^2$-O-α-glucosylmaltose (panose), $6^3$-O-α-glucosylmaltotriose (isomaltosylmaltose), $6^4$-O-α-glucosylmaltotetraose, or $6^5$-O-α-glucosylmaltopentaose was prepared as substrate solution. To each of the above substrate solution was added two units/mM-substrate of the purified α-isomaltosyl-transferring enzyme specimen obtained in Experiment 1-2 and incubated at 30° C. and at pH 6.0 for 12 hours. After deionizing by conventional method, the resulting reaction solutions were measured for saccharide composition on HPLC using "MCI GEL CK04SS", a column commercialized by Mitsubishi Chemical Industries, Ltd., Tokyo, Japan, at a column temperature of 80° C. and a flow rate of 0.4 ml/min of water, and using a detector "RI-8012", a differential refractometer commercialized by Tosho Corporation, Tokyo, Japan. The results are shown in Table 3.

TABLE 3

| Substrate | Saccharide in the reaction mixture | Content (%) |
|---|---|---|
| Glucose | Glucose | 100 |
| 6-O-α-Glucosylglucose | 6-O-α-Glucosylglucose | 100 |
| $6^2$-O-α-Glucosylmaltose | Glucose | 32.2 |
| | Isomaltose | 2.1 |
| | $6^2$-O-a-Glucosylmaltose | 4.6 |
| | Cyclotetrasaccharide | 43.5 |
| | Isomaltosylpanose | 4.8 |
| | Isomaltosypanoside | 1.8 |
| | others | 11.0 |
| $6^3$-O-α-Glucosylmaltotriose | Maltose | 50.6 |
| | Isomaltose | 2.0 |
| | $6^3$-O-α-Glucosylmaltotriose | 4.2 |
| | Cyclotetrasaccharide | 30.8 |
| | others | 12.4 |
| $6^4$-O-α-Glucosylmaltotetraose | Isomaltose | 1.9 |
| | Maltotriose | 60.7 |
| | Cyclotetrasaccharide | 25.6 |
| | $6^4$-O-α-Glucosylmaltotetraose | 3.4 |
| | others | 8.4 |
| $6^5$-O-α-Glucosylmaltopentaose | Isomaltose | 1.6 |
| | Maltotetraose | 66.5 |
| | Cyclotetrasaccharide | 18.2 |
| | $6^5$-O-α-Glucosylmaltopentaose | 4.3 |
| | others | 9.4 |

In Table 3, isomaltosylpanose means two forms of saccharides having the structure of structural formula 1 or 2, and isomaltosypanoside is a saccharide having the structure of Formula 3.

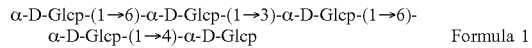

α-D-Glcp-(1→6)-α-D-Glcp-(1→3)-α-D-Glcp-(1→6)-α-D-Glcp-(1→4)-α-D-Glcp    Formula 1

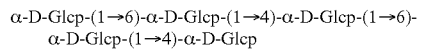

α-D-Glcp-(1→6)-α-D-Glcp-(1→4)-α-D-Glcp-(1→6)-α-D-Glcp-(1→4)-α-D-Glcp    Formula 2

Formula 3

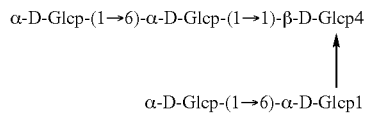

α-D-Glcp-(1→6)-α-D-Glcp-(1→1)-β-D-Glcp4
↑
α-D-Glcp-(1→6)-α-D-Glcp1

As evident from the results in Table 3, it was revealed that the polypeptide having α-isomaltosyl-transferring enzyme activity from *Bacillus globisporus* C11 acted on saccharides with a glucose polymerization degree of 3 or higher and having both the α-1,6-glucosyl linkage at their non-reducing end and the α-1,4 glucosidic linkage other than the linkage at the non-reducing end such as $6^2$-O-α-glucosylmaltose, $6^3$-O-α-glucosylmaltotriose, $6^4$-O-a-glucosylmaltotetraose, and $6^5$-O-α-glucosylmaltopentaose, and produced mainly cyclotetrasaccharide and maltooligosaccharide which decreased a glucose polymerization degree of 2 from the substrate. In addition to cyclotetrasaccharide, maltooligosaccharide which decreased a glucose polymerization degree of 2 from the substrate, and the remaining substrate, trace isomaltose considered to be a hydrolyzed product and other saccharide which differs from cyclotetrasaccharide, and considered to be a glucosyltransfer product were detected in the reaction mixture. The yield of cyclotetrasaccharide in dry basis from each substrates, i.e., $6^2$-O-α-glucosylmaltose, $6^3$-O-α-glucosylmaltotriose, $6^4$-O-a-glucosylmaltotetraose and $6^5$-O-α-glucosylmaltopentaose, were 43.5%, 30.8%, 25.6% and 18.2%, respectively. No product was detected from glucose and 6-O-α-glucosylglucose.

Experiment 2-2

N-terminal Amino Acid Sequence

The polypeptide having α-isomaltosyl-transferring enzyme activity had an amino acid sequence of SEQ ID NO:5 at the N-terminal side when the amino acid sequence was analyzed by "gas-phase protein sequencer model 473A", an apparatus of Applied Biosystems, 850 Lincoln Centre Drive, Foster City, U.S.A.

Experiment 2-3

Partial Amino Acid Sequence

A part of a purified specimen of polypeptide having α-isomaltosyl-transferring enzyme activity, obtained in Experiment 1-2, was dialyzed against 10 mM Tris-HCl buffer (pH 9.0) at 4° C. for 18 hours, and the dialyzed solution was diluted with a fresh preparation of the same buffer to give a concentration of about one mg/ml. One milliliter of the diluted solution as a test sample was admixed with 10 μg of "Lysyl Endopeptidase" commercialized by Wako Pure Chemicals, Ltd, Tokyo, Japan, and incubated at 30° C. for 22 hours to form peptides. The resulting hydrolyzate was subjected to HPLC to separate the peptides using "μ-BONDAPAK C18 column", having a diameter of 2.1 mm and a length of 150 mm, a product of Waters Chromatography Div., MILLIPORE Corp., Milford, USA, pre-equilibrated with 0.1% (v/v) trifluoroacetate containing 8% (v/v) acetonitrile, at a flow rate of 0.9 ml/min and at ambient temperature, and using a linear gradient of acetonitrile increasing from 8% (v/v) to 40% (v/v) in 0.1% (v/v) trifluoroacetate over 120 min. Peptide fragments eluted from the column were detected by monitoring the absorbance at a wavelength of 210 nm. Peptide fractions with a retention time of about 22 min, about 38 min, about 40 min, about 63 min and about 71 min were separately collected and dried in vacuo and then dissolved in a solution of 0.1% (v/v) trifluoroacetate and 50% (v/v) acetonitrile. Five peptide fragments were obtained, and each peptide fragments had amino acid sequences of SEQ ID NO:6 to 10 when these amino acid sequences were analyzed according to the method described in Experiment 2-2.

Experiment 2-4

Molecular Weight

When a purified specimen of polypeptide having α-isomaltosyl-transferring enzyme activity, obtained by the method in Experiment 1-2, was subjected to SDS-PAGE according to the method reported by U. K. Laemmli in *Nature*, Vol. 227, pp. 680–685 (1970), a single protein band having the enzymatic activity was observed at the position corresponding to the molecular weight of about 82,000 to 122,000 daltons. Molecular weight markers used in this experiment were myosin (200,000 daltons), β-galactosidase (116,250 daltons), phosphorylase B (97,400 daltons), serum albumin (66,200 daltons) and ovalbumin (45,000 daltons).

Experiment 2-5

Optimum Temperature

As shown in FIG. 1, when a purified specimen of polypeptide having α-isomaltosyl-transferring enzyme activity, obtained by the method in Experiment 1-2, was acted on the substrate at various temperatures for 30 min by conventional method, the polypeptide had an optimum temperature at about 50° C.

Experiment 2-6

Optimum pH

As shown in FIG. 2, when a purified specimen of polypeptide having α-isomaltosyl-transferring enzyme activity, obtained by the method in Experiment 1-2, was acted on the substrate in MacIlvaine buffer of various pHs at 35° C. for 30 min by conventional method, the polypeptide had an optimum pH at about 5.5 to 6.0.

Experiment 2-7

Thermal Stability

As shown in FIG. 3, when a purified specimen of polypeptide having α-isomaltosyl-transferring enzyme activity, obtained by the method in Experiment 1-2, was incubated in 20 mM acetate buffer (pH 6.0) at various temperatures for 60 min by conventional method, the polypeptide had thermal stability of up to about 40° C.

Experiment 2-8 pH Stability

As shown in FIG. 4, when a purified specimen of polypeptide having α-isomaltosyl-transferring enzyme activity, obtained by the method in Experiment 1-2, was in MacIlvaine buffer or 50 mM disodium carbonate-sodium bicarbonate buffer of various pHs at 4° C. for 24 hours by conventional method, the polypeptide had pH stability of about 4.5 to about 9.0.

Experiment 3

Polypeptide from *Bacillus globisporus* N75

Experiment 3-1

Preparation of Crude Polypeptide

A liquid culture medium consisting 4% (w/v) of "PINE-DEX #4", a partial starch hydrolyzate, 1.8% (w/v) of "ASAHIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 min, cooled and seeded with *Bacillus globisporus* N75 strain, FERM BP-7591, followed by culturing under rotary-shaking conditions at 27° C. and 230 rpm for 48 hours for a seed culture.

About 20 L of a fresh preparation of the same liquid culture medium as used in the above seed culture were placed in a 30 L fermentor, sterilized by heating, and then cooled to 27° C. and inoculated with 1% (v/v) of the seed culture, followed by culturing at 27° C. and pH 6.0 to 8.0 for 48 hours under aeration-agitation conditions. The resultant culture, having about 1.1 units/ml of α-isomaltosyl-transferring enzyme, was centrifuged at 10,000 rpm for 30 min to obtain about 18 L of supernatant. Measurement of the supernatant revealed that it had about 1.1 units/ml of α-isomaltosyl-transferring enzyme activity, i.e., a total enzyme activity of about 19,800 units; about 0.33 units/ml of α-isomaltosylglucosaccharide-forming enzyme activity, i.e., a total enzyme activity of about 5,490 units. It was revealed that both enzymes were secretion polypeptides detected in the culture supernatant.

About 18 L of the culture supernatant described above was salted out with 60% saturated ammonium sulfate solution and allowed to stand at 4° C. for 24 hours, and the formed precipitates were collected by centrifugation at 10,000 rpm for 30 min, dissolved in 10 mM Tris-HCl buffer (pH 8.3), and dialyzed against the same buffer to obtain about 450 ml of crude enzyme solution. The crude enzyme solution had about 15,700 units of α-isomaltosyl-transferring enzyme activity and 4,710 units of α-isomaltosylglucosaccharide-forming enzyme activity. The crude enzyme solution was subjected to ion-exchange column chromatography using "SEPABEADS FP-DA13" gel, disclosed in Experiment 1-1. α-Isomaltosyl-transferring enzyme was eluted as non-adsorbed fraction without adsorbing on "SEPABEADS FP-DA13" gel, and α-isomaltosylglucosaccharide-forming enzyme was adsorbed on "SEPABEADS FP-DA13" gel. Subsequently, α-isomaltosylglucosaccharide-forming enzyme was eluted with a linear gradient of increasing from 0 M to 1 M of sodium chloride, where the enzyme was eluted with the linear gradient of sodium chloride at a concentration of about 0.25 M. Therefore, fractions with α-isomaltosyl-transferring enzyme and with α-isomaltosylglucosaccharide-forming enzyme were separately collected as crude polypeptide having α-isomaltosyl-transferring enzyme activity and that having α-isomaltosylglucosaccharide-forming enzyme activity, respectively.

Further, the polypeptide having α-isomaltosyl-transferring enzyme and that having α-isomaltosylglucosaccharide-forming enzyme were separately purified and prepared by the methods described in the below.

Experiment 3-2

Purification of a Polypeptide having an α-Isomaltosyl-Transferring Enzyme Acticity The crude polypeptide having α-isomaltosyl-transferring activity, obtained in Experiment 3-1, was dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Corp., Div. Amersham International, Arlington heights, Ill., USA. The polypeptide was adsorbed on "SEPHACRYL HR S-200" gel and, when eluted with a linear gradient decreasing from 1 M to 0 M of ammonium sulfate, the enzymatic activity was eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by hydrophobic column chromatography using "BUTYL-TOYOPEARL 650M" gel, a hydrophobic gel commercialized by Tosho Corporation, Tokyo, Japan. The polypeptide was adsorbed on "BUTYL-TOYOPEARL 650M" gel and, when eluted with a linear gradient decreasing from 1 M to 0M of ammonium sulfate, the enzymatic activity was eluted with a linear gradient of ammonium sulfate at about 0.3 M, and fractions with the enzyme activity was collected. The collected solution was dialyzed against 10 mM Tris-HCl buffer (pH 8.0), and the dialyzed solution was centrifuged to remove impurities, and purified by ion-exchange column chromatography using 380 ml of "SuperQ-TOYOPEARL 650C" gel, a ion-exchange gel commercialized by Tosho Corporation, Tokyo, Japan. The polypeptide was eluted as non-adsorbed fraction without adsorbing on "SuperQ-TOYOPEARL 650C" gel. The purified polypeptide specimen having α-isomaltosyl-transferring enzyme activity was obtained by collecting the fractions. The amount of enzyme activity, specific activity and yield of the α-isomaltosyl-transferring enzyme in each purification step are shown in Table 4.

TABLE 4

| Purification step | Enzyme* activity (unit) | Specific activity of enzyme* (unit/mg protein) | Yield (%) |
|---|---|---|---|
| Culture supernatant | 19,000 | 0.33 | 100 |
| Dialyzed solution after salting out with ammonium sulfate | 15,700 | 0.64 | 82.6 |
| Elute from ion-exchange column chromatography | 12,400 | 3.56 | 65.3 |
| Elute from affinity column chromatography | 8,320 | 11.7 | 43.8 |
| Elute from hydrophobic column chromatography | 4,830 | 15.2 | 25.4 |
| Elute from ion-exchange column chromatography | 3,850 | 22.6 | 20.3 |

Note:
The symbol "*" means the α-isomaltosyl-transferring enzyme of the present invention.

The finally purified α-isomaltosyl-transferring enzyme specimen was assayed for purity on gel electrophoresis using a 7.5% (w/v) polyacrylamide gel and detected on the gel as a single protein band, i.e., a high purity specimen.

Experiment 3-3

Purification of α-Isomaltosylglucosaccharide-Forming Enzyme

The crude polypeptide having α-isomaltosylglucosaccharide-forming enzyme activity, obtained in Experiment 3-1, was dialyzed against 10 mM sodium phosphate buffer (pH 7.0) with 1 M ammonium sulfate. The dialyzed solution was centrifuged to remove impurities, and subjected to affinity column chromatography using 500 ml of "SEPHACRYL HR S-200" gel, a gel commercialized by Amersham Corp., Div. Amersham International, Arlington heights, Ill., USA. The enzyme was adsorbed on "SEPHACRYL HR S-200" gel and, when sequentially eluted with a linear gradient decreasing from 1 M to 0 M of ammonium sulfate and a linear gradient increasing from 0 mM to 100 mM of maltotetraose, the enzymatic activity was eluted with a linear gradient of maltotetraose at about 30 mM, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by hydrophobic column chromatography using 350 ml of "BUTYL-TOYOPEARL 650M" gel, a hydrophobic gel commercialized by Tosho Corporation, Tokyo, Japan. The enzyme was adsorbed on "BUTYL-TOYOPEARL 650M" gel and, when eluted with a linear gradient decreasing from 1 M to 0 M of ammonium sulfate, the enzymatic activity was eluted with a linear gradient of ammonium sulfate at about 0.3 M, and fractions with the enzyme activity was collected. The collected solution was dialyzed against 10 mM sodium phosphate buffer (pH 7.0) with 1 M ammonium sulfate, and the dialyzed solution was centrifuged to remove impurities, and purified by affinity chromatography using "SEPHACRLY HR S-200" gel. The amount of enzyme activity, specific activity and yield of the α-isomaltosylglucosaccharide-forming enzyme in each purification step are shown in Table 5.

TABLE 5

| Purification step | Enzyme* activity (unit) | Specific activity of enzyme* (unit/mg protein) | Yield (%) |
|---|---|---|---|
| Culture supernatant | 5,940 | 0.10 | 100 |
| Dialyzed solution after salting out with ammonium sulfate | 4,710 | 0.19 | 79.3 |
| Elute from ion-exchange column chromatography | 3,200 | 2.12 | 53.9 |
| Elute from affinity column chromatography | 2,210 | 7.55 | 37.2 |
| Elute from hydrophobic column chromatography | 1,720 | 10.1 | 29.0 |
| Elute from affinity column chromatography | 1,320 | 12.5 | 22.2 |

Note:
The symbol "*" means the α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, i.e., a high purity specimen.

Experiment 4

Physicochemical Properties of Polypeptide having an α-Isomaltosyl-Transferring Enzyme Activity Experiment 2-1

Action

An aqueous solution containing 10 mM of glucose, 6-O-α-glucosylglucose (isomaltose), $6^2$-O-α-glucosylmaltose (panose), $6^3$-O-α-glucosylmaltotriose (isomaltosylmaltose), $6^4$-O-αglucosylmaltotetraose, or $6^5$-O-α-glucosylmaltopentaose was prepared as substrate solution. To each of the above substrate solutions was added two units/mM-substrate of the purified α-isomaltosyl-transferring enzyme specimen obtained in Experiment 3-2 and incubated at 30° C. and at pH 6.0 for 12 hours. After deionizing by conventional method, the resulting reaction solutions were measured for saccharide composition on HPLC, disclosed in Experiment 2-1. The results are shown in Table 6.

TABLE 6

| Substrate | Saccharide in the reaction mixture | Content (%) |
|---|---|---|
| Glucose | Glucose | 100 |
| 6-O-α-Glucosylglucose | 6-O-α-Glucosylglucose | 100 |
| $6^2$-O-α-Glucosylglucose | Glucose | 31.8 |
| | Isomaltose | 2.0 |
| | $6^2$-O-a-Glucosylglucose | 4.4 |
| | Cyclotetrasaccharide | 43.2 |
| | Isomaltosylpanose | 6.5 |
| | Isomaltosypanoside | 2.4 |
| | others | 9.7 |
| $6^3$-O-α-Glucosylglucose | Maltose | 50.3 |
| | Isomaltose | 1.9 |
| | $6^3$-O-α-Glucosylglucose | 4.5 |
| | Cyclotetrasaccharide | 30.9 |
| | others | 12.4 |
| $6^4$-O-α-Glucosylglucose | Isomaltose | 1.5 |
| | Maltotriose | 60.9 |
| | Cyclotetrasaccharide | 25.8 |
| | $6^4$-O-α-Glucosylglucose | 3.2 |
| | others | 8.6 |
| $6^5$-O-α-Glucosylglucose | Isomaltose | 1.4 |
| | Maltotetraose | 66.6 |
| | Cyclotetrasaccharide | 18.7 |

TABLE 6-continued

| Substrate | Saccharide in the reaction mixture | Content (%) |
|---|---|---|
| | $6^5$-O-α-Glucosylglucose | 4.2 |
| | others | 9.1 |

As evident from the results in Table 6, it was revealed that the polypeptide having α-isomaltosyl-transferring activity from *Bacillus globisporus* N75 acted on saccharides with a glucose polymerization degree of 3 or higher and having both the α-1,6-glucosidic linkage as a linkage at the non-reducing end and the α-1,4 glucosidic linkage other than the linkage at the non-reducing ends such as $6^2$-O-α-glucosylmaltose, $6^3$-O-α-glucosylmaltotriose, $6^4$-O-α-glucosylmaltotetraose, and $6^5$-O-α-glucosylmaltopentaose, and produced mainly cyclotetrasaccharide and maltooligosaccharides which decreased a glucose polymerization degree of 2 from the substrate. In addition to cyclotetrasaccharide, maltooligosaccharide which decreased a glucose polymerization degree of 2 from the substrate, and the remaining substrate, trace isomaltose considered to be a hydrolyzed product and other saccharide which differs from cyclotetrasaccharide, and considered to be a glucosyltransfer product were detected in the reaction mixture. The yield of cyclotetrasaccharide in dry basis from $6^2$-O-α-glucosylmaltose, $6^3$-O-α-glucosylmaltotriose, $6^4$-O-α-glucosylmaltotetraose and $6^5$-O-α-glucosylmaltopentaose were 43.2%, 30.9%, 25.8% and 18.7%, respectively. No product was detected from 6-O-α-glucosylglucose.

Experiment 4-2

N-Terminal Amino Acid Sequence

The polypeptide having α-isomaltosyl-transferring enzyme activity, prepared in Experiment 3-2, had an amino acid sequence of SEQ ID NO:5 at N-terminal side when the amino acid sequence was analyzed by "protein sequencer model 473A", an apparatus of Applied Biosystems, 850 Lincoln Centre Drive, Foster City, U.S.A.

Experiment 4-3

Partial Amino Acid Sequence

A part of a purified specimen of polypeptide having α-isomaltosyl-transferring activity, obtained in Experiment 3-2, was dialyzed against 10 mM Tris-HCl buffer (pH 9.0) at 4° C., and the dialyzed solution was diluted with a fresh preparation of the same buffer to give a concentration of about one mg/ml. One milliliter of the diluted solution as a test sample was admixed with 10 µg of "Lysyl Endopeptidase" commercialized by Wako Pure Chemicals, Ltd, Tokyo, Japan, and incubated at 30° C. for 22 hours to form peptides. The resulting partial hydrolyzate was subjected to HPLC to separate the peptides using "µ-BONDASPHERE C18 column", having a diameter of 3.9 mm and a length of 150 mm, a product of Waters Chromatography Div., MILLIPORE Corp., Milford, USA, pre-equilibrated with 0.1% (v/v) trifluoroacetate containing 4% (v/v) acetonitrile, at a flow rate of 0.9 ml/min and at ambient temperature, and using a linear gradient of acetonitrile increasing from 8% (v/v) to 42.4% (v/v) in 0.1% (v/v) trifluoroacetate over 90 min. Peptide fragments eluted from the column were detected by monitoring the absorbance at a wavelength of 210 nm. Peptide fractions with a retention time of about 21 min, about 38 min, about 56 min, and about 69 min were separately collected and dried in vacuo and then dissolved in a solution of 0.1% (v/v) trifluoroacetate and 50% (v/v) acetonitrile. Five peptide fragments were obtained, and each peptide fragment had amino acid sequences of SEQ ID NO:8 and 11 to 14 when these amino acid sequences were analyzed according to the method described in Experiment 2-2.

Experiment 4-4

Molecular Weight

When a purified specimen of polypeptide having α-isomaltosyl-transferring activity, obtained by the method in Experiment 3-2, was subjected to SDS-PAGE according to the method disclosed in Experiment 2-4, a single protein band having the enzymatic activity was observed at the position corresponding to the molecular weight of about 92,000 to 132,000 daltons in comparison with molecular markers, commercialized by Bio-Rad Laboratories, Hercules, Calif. 94547, U.S.A., and subjected to SDS-PAGE at the same time.

Experiment 4-5

Octimum Temperature

A purified specimen of polypeptide having α-isomaltosyl-transferring activity, obtained by the method in Experiment 3-2, was acted on the substrate in 20 mM acetate buffer (pH6.0) at various temperatures for 30 min, according to the assay method of α-isomaltosyl-transferring enzyme disclosed in Experiment 1-1. As shown in FIG. 5, the polypeptide had an optium temperature at about 50 ° C.

Experiment 4-6

Octimum pH

A purified specimen of polypeptide having α-isomaltosyl-transferring activity, obtained by the method in Experiment 3-2, was acted on the substrate in MacIlvaine buffer of various pHs at 35° C. for 30 min according to the assay method of α-isomaltosyl-transferring enzyme disclosed in Experiment 1-1. As shown inm FIG. 6, the polypeptide had an octimum pH at about 6.0

Experiment 4-7

Thermal Stability

A purified specimen of polypeptide having α-isomaltosyl-transferring activity, obtained by the method in Experiment 3-2, was incubated in 20 mM acetate buffer (pH6.0) at various temperatures for 60 min according to the assay method of α-isomaltosyl-transferring enzyme disclosed in Experiment 1-1. As shown in FIG. 7, the polypeptide had thermal stability of up to about 45° C.

Experiment 4-8 pH Stability

Figure 8:
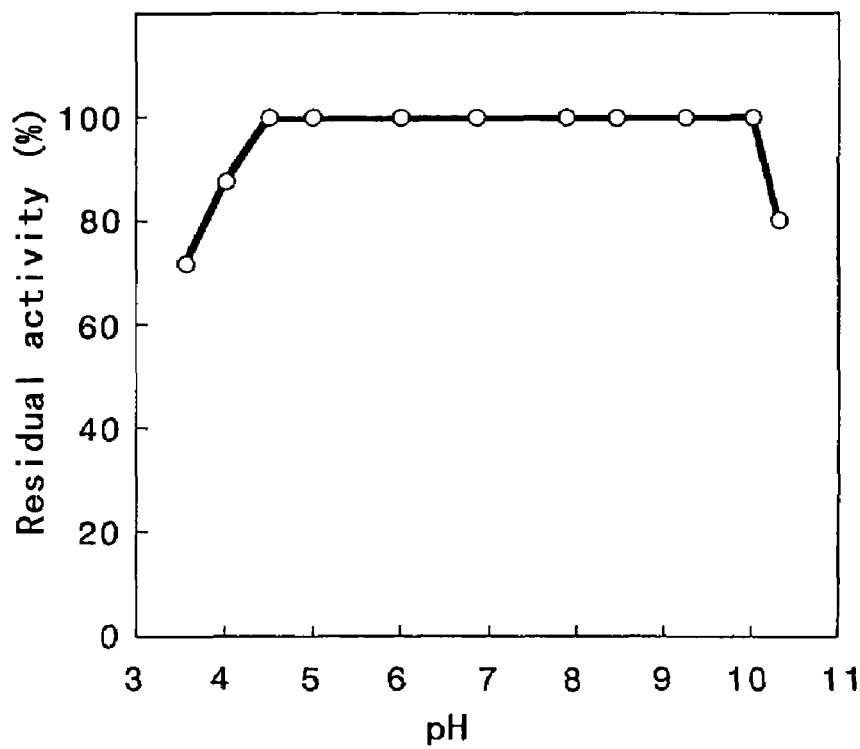
FIG. 8 shows the pH stability of a polypeptide having α-isomaltosyl-transferring enzyme activity from a microorganism of the species *Bacillus globisporus* N75 strain.

A purified specimen of polypeptide having α-isomaltosyl-transferring activity, obtained by the method in Experiment 3-2, was incubated in MacIlvaine buffer or 50 mM disodium carbonate-sodium bicarbonate buffer of various pHs at 4° C. for 24 hours according to the assay method of α-isomaltosyl-transferring enzyme disclosed in Experiment 1-1. As shown in FIG. 8, the polypeptide had pH stability of about 4.5 to about 10.

Experiment 5

Recombinant DNA Containing a DNA Encoding a Polypeptide from *Bacillus globisporus* C11 and Transformant Experiment 5-1

Preparation of Chromosonal DNA from *Bacillus globisporus* C11

A liquid culture medium consisting 2% (w/v) of "PINE-DEX #4", a partial starch hydrolyzate, 1.0% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmyer flasks in a respective amount of 100 ml, sterilized by autoclaving at 121° C. for 20 min, cooled and inoculated with *Bacillus globisporus* C11, FERM BP-7144, followed by culturing under rotary-shaking conditions at 27° C. and 230 rpm for 24 hours. The cells collected from the culture by centrifugation were suspended in TES buffer (pH 8.0), the suspended solution was admixed with lysozyme to give a concentration of 0.05% (w/v), and incubated at 37° C. for 30 min. After freezing the lysate at −80° C. for one hour, the lysate was added with TES buffer (pH 9.0)and heated to 60° C. The solution was added with a mixture of TES buffer and phenol, and was vigorously shaken for five minute in an ice bath, and the supernatant was collected by centrifugation. The supernatant was added to twice the volume of cold ethanol, and the resulting crude precipitate was collected as a crude chromosomal DNA. The crude chromosomal DNA was dissolved in SSC buffer (pH 7.1), and admixed with 7.5 µg of ribonuclease and 125 µg of proteinase, and incubated 37° C. for one hour. The chromosomal DNA was extracted from the reactant by adding chloroform/isoamylalcohol mixture, then added cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 5-2

Preparation of a Recombinant DNA, pBGC1 and a Transformant, BGC1

Figure 9:
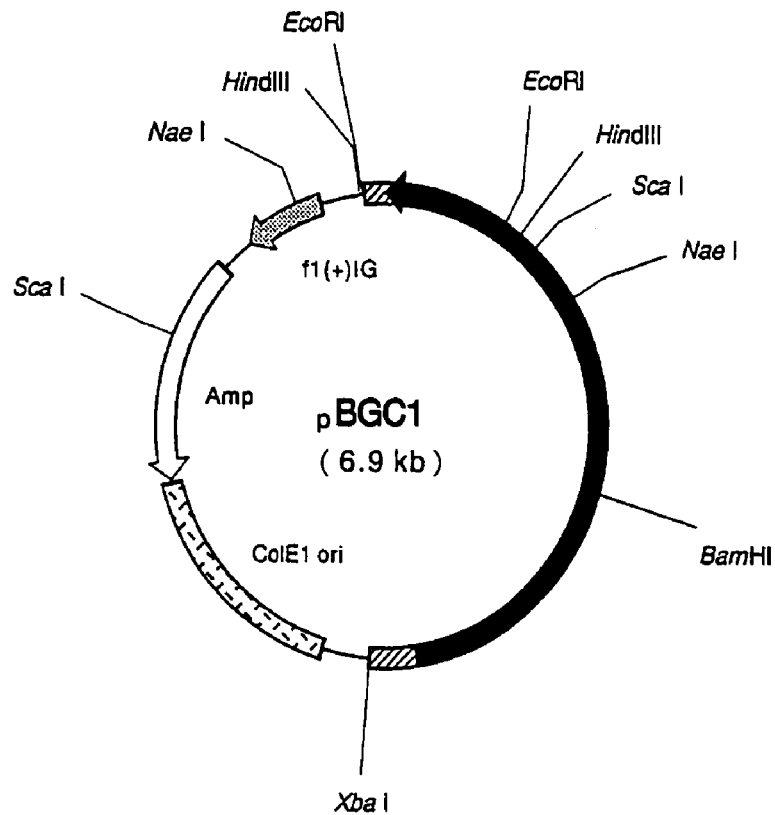
FIG. 9 shows the restriction enzyme map of a recombinant DNA, pBGC1, of the present invention. In the figure, a section indicated with black bold line is a DNA encoding a polypeptide having α-isomaltosyl-transferring enzyme activity from a microorganism of the species *Bacillus globisporus* C11 strain.

One milliliter of purified chromosomal DNA solution, prepared by the method in Experiment 5-1, was admixed with about 35 units of a restriction enzyme, Sau 3AI, and incubated at 37☐ for 20 min for partial digestion of the chromosomal DNA. The resulting DNA fragments corresponding to about 2,000 to 6,000 base pairs were collected by sucrose density-gradient centrifugation. A plasmid vector, Bluescript II SK(+), commercialized by Stratagene Cloning System, was completely digested with a restriction enzyme, Bam HI by conventional method. A recombinant DNA was obtained by ligating 0.5 µg of the digested plasmid vector with about 5 µg of the DNA fragments prepared before by using a "DNA ligation kit", commercialized by Takara Shuzo Co., Ltd., according to the method described in a document attached with the kit. Then, a gene library was prepared by transforming 100 µl portion of the competent cell, "Epicurian Coli XL2-Blue", commercialized by Stratagene Cloning System, with the recombinant DNA by conventional competent cell method. The transformants thus obtained as gene library were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37☐ for 24 hours. About five thousand white colonies grown on the plate were transferred to and fixed on a nylon membrane, "Hybond-N+", commercialized by Amasham Bioscience K.K. An oligonucleotide having a nucleotide sequence of "5'-AAY-TGGTGGATGWSNAA-3'" (SEQ ID NO:17) was chemically synthesized on the bases of an amino acid sequence of first to sixth of SEQ ID NO:8, which disclosed by the method in Experiment 2-3. A synthetic DNA (probe 1) was obtained by labeling the oligonucleotide with radioisotope using [γ-$^{32}$P]ATP and T4 polynucleotide kinase according to the conventional method. Subsequently, four types of transformants showing remarkable hybridization with probe 1 were selected from the colonies fixed on the nylon membrane obtained before, using conventional colony hybridization. The recombinant DNAs were collected from these four types of transformants by conventional method. On the other hand, probe 2 having the nucleotide sequence of "5'-GTNTTYAAYCARTAYAA-3'" (SEQ ID NO:18) was chemically synthesized based on a amino acid sequence of ninth to fourteenth of SEQ ID NO:7 and labeled with radioisotope in the same manner. The recombinant DNAs obtained and probe 2 were used for conventional southern-hybridization, and a recombinant DNA showing a remarkable hybridization with probe 2 was selected. A transformant thus selected was named "BGC1". According to the conventional method, the transformant, BGC1 was inoculated into L-broth medium (pH 7.0) containing 100 µg/ml of ampicillin sodium salt, and cultured under rotary-shaking conditions at 37☐ for 24 hours. After the completion of the culture, cells were collected by centrifugation, and the recombinant DNA was extracted from the cells by conventional alkaline-SDS method. When the nucleotide sequence of the recombinant DNA was analyzed by conventional dideoxy method, it was revealed that the recombinant DNA contained a DNA having the nucleotide sequence of SEQ ID NO:15, 3,869 base pairs, which originated from *Bacillus globisporus* C11 (FERM BP-7144). In the recombinant DNA, a DNA having the nucleotide sequence of SEQ ID NO:15 was shown in FIG. 9 with the part of black-bold line, and was ligated at downstream of recognition site of a restriction enzyme, Xba I.

The amino acid sequence deduced from the nucleotide sequence is as shown in parallel in SEQ ID NO:15. The amino acid sequence was compared with amino acid sequences of polypeptide having α-isomaltosyl-transferring enzyme activity, i.e., the N-terminal amino acid sequence of SEQ ID NO:5 disclosed by the method in Experiment 2-2 and the internal partial amino acid sequences of SEQ ID NO:6 to 10 disclose by the method in Experiment 2-3. An amino acid sequence of SEQ ID NO:5 was completely identical with that of 30th to 48th of the amino acid sequence shown in parallel in SEQ ID NO:15. Amino acid sequences of SEQ ID NO:6, 7, 8, 9, and 10 were completely identical with those of 584th to 597th, 292nd to 305th, 545th to 550th, 66th to 77th, and 390th to 400th of the amino acid sequence shown in parallel in SEQ ID NO:15, respectively. These results indicate that the polypeptide having α-isomaltosyl-transferring enzyme activity contains the amino acid sequence of SEQ ID NO:1, and that the polypeptide is encoded by the DNA having the nucleotide sequence of SEQ ID NO:3 in the case of *Bacillus globisporus* C11 (FERM BP-7144). An amino acid sequence of the first to 29th of that showing in parallel in SEQ ID NO:15 was presumed to be a secretion signal sequence of the polypeptide. According to the results described above, it was revealed that the precursor peptide of the polypeptide before secretion had the amino acid sequence shown in parallel in SEQ ID NO:15, and the amino acid sequence was encoded by the nucleotide sequence of SEQ ID NO:15. The recombinant DNA prepared and confirmed the nucleotide sequence as described above was named "pBGC1".

Experiment 6

Preparation of a Recombinant DNA Containing a DNA Encoding Polypeptide from *Bacillus globisporus* N75 and a Transformant Experiment 6-1

Preparation of Chromosomal DNA from *Bacillus globisporus* N75

A liquid culture medium consisting 2% (w/v) of "PINE-DEX #4", a partial starch hydrolyzate, 1.0% (w/v) of "ASA-HIMEAST", a yeast extract, 0.1% (w/v) of dipotassium phosphate, 0.06% (w/v) of sodium phosphate dodeca-hydrate, 0.05% (w/v) of magnesium sulfate hepta-hydrate, and water was placed in 500-ml Erlenmeyer flasks in a respective amount of 100 ml, sterilized by autoclaving at 121° C. for 20 min, cooled and inoculated with *Bacillus globisporus* N75, FERM BP-7591, followed by culturing under rotary-shaking conditions at 27° C. and 230 rpm for 24 hours. The cells collected from the culture by centrifugation were suspended in TES buffer (pH 8.0), the suspended solution was admixed with lysozyme to give a concentration of 0.05% (w/v), and incubated at 37° C. for 30 min. After freezing the lysate at −80° C. for one hour, the lysate was added with TES buffer (pH 9.0)and heated to 60° C. The solution was added with a mixture of TES buffer and phenol, and was vigorously shook for five minute in an ice bath, and the supernatant was collected by centrifugation. The supernatant was added twice volume of cold ethanol, and resulting Crude precipitate was collected as crude chromosomal DNA. The crude chromosomal DNA was dissolved in SSC buffer (pH 7.1), and admixed with 7.5 μg of ribonuclease and 125 μg of proteinase, and incubated 37° C. for one hour. The chromosomal DNA was extracted from the reactant by adding chloroform/isoamylalcohol mixture, then added cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 6-2

Preparation of a Recombinant DNA, pBGN1 and a Transformant, BGN1

Figure 10:
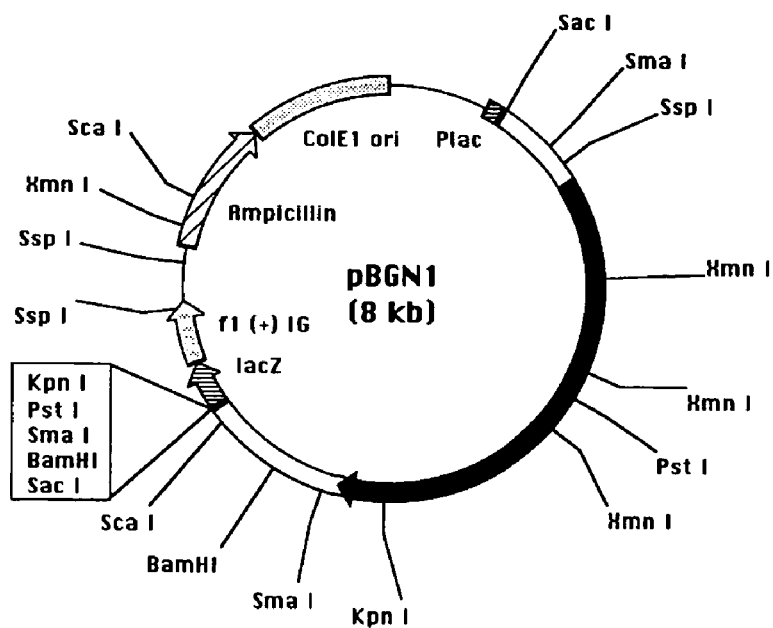
FIG. 10 shows the restriction enzyme map of a recombinant DNA, pBGC1, of the present invention. In the figure, a section indicated with black bold line is a DNA encoding a polypeptide having α-isomaltosyl-transferring enzyme activity from a microorganism of the species *Bacillus globisporus* N75 strain.

One hundred μl (0.1 ml) of purified chromosomal DNA solution, prepared by the method in Experiment 6-1, was admixed with about 100 units of a restriction enzyme, Sac I, and incubated at 37□ for 6 hours to digest the chromosomal DNA. The resulting DNA fragments were separated by agarose gel electrophoresis, and DNA fragments corresponding to about 3,000 to 7,000 base pairs were collected using a DNA purification kit, "GENECLEAN II KIT", commercialized by Quantum Biotechnologies, Carlsbad, Calif. 92008, U.S.A., according to the method described in a document attached with the kit. A plasmid vector, Bluescript II SK(+), commercialized by Stratagene Cloning System, was completely digested with a restriction enzyme, Sac I. A recombinant DNA was obtained by ligating 0.5 μg of the digested plasmid vector with about 5 μg of the DNA fragments prepared before by using a "DNA ligation kit", commercialized by Takara Shuzo Co., Ltd., according to the method described in a document attached with the kit. Then, a gene library was prepared by transforming 100 μl portion of the competent cell, "Epicurian Coli XL2-Blue", commercialized by Stratagene Cloning System, with the recombinant DNA by conventional competent cell method. The transformants thus obtained as gene library were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37° C. for 24 hours. About four thousand white colonies grown on the plate were transferred to and fixed on a nylon membrane, "Hybond-N+", commercialized by Amasham Bioscience K.K. An oligonucleotide having a nucleotide sequence of "5'-AAYTGGTGGATGWSNAA-3'" (SEQ ID NO:17) was chemically synthesized on the bases of an amino acid sequence of first to sixth of SEQ ID NO:8, which disclosed by the method in Experiment 2-3. A synthetic DNA (probe 1) was obtained by labeling the oligonucleotide with radioisotope using [γ-$^{32}$P]ATP and T4 polynucleotide kinase according to the conventional method. Subsequently, two types of transformant showing remarkable hybridization with probe 1 were selected from the colonies fixed on the nylon membrane obtained before, using conventional colony hybridization. The recombinant DNAs were collected from these two types of transformant by conventional method. On the other hand, probe 2 having the nucleotide sequence of "5'-GAYTGGATHGAYTTYTGGTTYGG-3'" (SEQ ID NO:19) was chemically synthesized based on a amino acid sequence of eighth to fifteenth of SEQ ID NO:14 and labeled with radioisotope in the same manner. The recombinant DNAs obtained and probe 2 were used for conventional southern-hybridization, and a recombinant DNA showing a remarkable hybridization with probe 2 was selected. A transformant thus selected was named "BGN1". According to the conventional method, the transformant, BGN1 was inoculated into L-broth medium (pH 7.0) containing 100 μg/ml of ampicillin sodium salt, and cultured under rotary-shaking conditions at 37° C. for 24 hours. After the completion of the culture, cells were collected by centrifugation, and the recombinant DNA was extracted from the cells by conventional alkaline-SDS method. When the nucleotide sequence of the recombinant DNA was analyzed by conventional dideoxy method, it was revealed that the recombinant DNA contained a DNA having the nucleotide sequence of SEQ ID NO:16, 4,986 base pairs, which originated from *Bacillus globisporus* N75 (FERM BP-591). In the recombinant DNA, a DNA having the nucleotide sequence of SEQ ID NO:16 was shown in FIG. 10 with the part of black-bold line, and was ligated at downstream of recognition site of a restriction enzyme, Sac I.

The amino acid sequence deduced from the nucleotide sequence is as shown in parallel in SEQ ID NO:16. The amino acid sequence was compared with amino acid sequences of polypeptide having α-isomaltosyl-transferring enzyme activity, i.e., the N-terminal amino acid sequence of SEQ ID NO:5 disclosed by the method in Experiment 4-2 and the internal partial amino acid sequences of SEQ ID NO:8 and 11 to 14 disclose by the method in Experiment 4-3. An amino acid sequence of SEQ ID NO:5 was completely identical with that of 30th to 48th of the amino acid sequence shown in parallel in SEQ ID NO:16. Amino acid sequences of SEQ ID NO:8, 11, 12, 13, and 14 were completely identical with those of 545th to 550th, 565th to 582nd, 66th to 83rd, 390th to 406th, and 790th to 809th of the amino acid sequence shown in parallel in SEQ ID NO:16, respectively. These results indicate that the polypeptide having α-isomaltosyl-transferring enzyme activity contains the amino acid sequence of SEQ ID NO:2, and that the polypeptide is encoded by the DNA having the nucleotide sequence of SEQ ID NO:4 in the case of *Bacillus globisporus* N75 (FERM BP-7591). An amino acid sequence of the first to 29th of that showing in parallel in SEQ ID NO:16 was presumed to be a secretion signal sequence of the polypeptide. According to the results described above, it was revealed that the precursor peptide of the polypeptide before secretion had the amino acid sequence shown in parallel in SEQ ID NO:16, and the amino acid sequence was encoded by the nucleotide sequence of SEQ ID NO:16. The recombinant DNA prepared and confirmed the nucleotide sequence as described above was named "pBGN1".

Experiment 7

Production of Polypeptides having α-Isomaltosyl-Transferring Enzyme Activity by Transformants Experiment 7-1

A Transformant, BGC1

A liquid culture medium consisting 5 g/L of "PINE-DEX #4", a partial starch hydrolyzate, 20 g/L of polypeptone, 20 g/L of yeast extract, 1 g/L of sodium phosphate dodecahydrate, and water was placed in a 500-ml Erlenmeyer flask in a amount of 100 ml, sterilized by autoclaving at 121° C. for 15 min, and cooled. Then, the liquid medium was sterilely set to pH 7.0, and sterilely admixed with 10 mg of ampicillin sodium salt. A transformant, BGC1, obtained by the method in Experiment 5-2, was inoculated into the above liquid medium, and cultured at 27° C. and for 48 hours under aeration-agitation conditions. To investigate the location of the polypeptide in the culture, cells and supernatant were separately collected by conventional centrifugation. In the case of the cells, whole-cell extract, obtained by ultrasonic disruption, and periplasmic extract, obtained by osmotic shock procedure were prepared separately. In the case of ultrasonic disruption, cells were suspended in 10 mM sodium phosphate buffer (pH 7.0), and then disrupted in an ice bath using a ultrasonic homogenizer, "model UH-600", commercialized by MST Corporation, Aichi, japan. In the case of osmotic shock procedure, cells were washed with 10 mM Tris-HCl buffer (pH 7.3) containing 30 mM sodium chloride, and the washed cells were suspended in 33 mM Tris-HCl buffer (pH 7.3) containing 200 g/L of sucrose and 1 mM EDTA, shook at 27° C. for 20 min, and then centrifuged to collect the cells. Subsequently, the cells were suspended in 0.5 mM magnesium chloride solution precooled to about 4° C., and shaken in ice bath for 20 min to extract periplasmic fraction. α-Isomaltosyl-transferring enzyme activities of culture supernatant, whole-cell extract and periplasmic extract, prepared as described above, were assayed, and those values were expressed in terms of the activities/ml-culture, respectively. The results are shown in Table 7.

TABLE 7

| Sample | α-isomaltosyl-transferring enzyme activity (units/ml-culture) |
|---|---|
| Culture supernatant | 0.0 |
| Whole-cell extract | 3.4 |
| Periplasmic extract | 3.0 |

As evident from the results in Table 7, it was revealed that the transformant, *E. coli* BGC1 produced the polypeptide having α-isomaltosyl-transferring enzyme activity of the present invention intracellularly, and secreted most of it in periplasmic fraction.

As the first control experiment, *E. coli* XL2-Blue was cultured with the same conditions in the case of the transformant described above except for the addition of ampicillin, and a supernatant and a cell-extract were prepared from the culture. As the second control experiment, *Bacillus globisporus* C11, FERM BP-7144, was cultured with the same conditions in the case of the transformant described above except for the addition of ampicillin, and a supernatant and a cell-extract were prepared from the culture. In the first control experiment, the enzyme activity was not detected from either of the culture supernatant and the cell-extract. In the second control experiment, the enzyme activity of the culture supernatant and the cell-extract were about 1.2 units and about 0.1 units, respectively, and the total enzyme activity per one milliliter-culture was about 1.3 units. Compared with the total enzyme activity, 3.4 units/ml-culture, of the transformant BGC1, the enzyme activity was evidently low-level values.

The periplasmic fraction was further purified by salting out, dialysis and successive column chromatographies on "SEPABEADS FP-DA13" gel, "SEPHACRYL HR S-200" gel, and "BUTYL-TOYOPEARL 650M" gel according to the methods described in Experiment 1, and the purified polypeptide was analyzed according to the methods described in Experiment 2. As the results, the molecular weight was about 82,000 to 122,000 daltons by SDS-polyacrylamide gel electrophoresis, the isoelectric point was about 5.1 to 6.1 by polyacrylamide gel isoelectrophoresis, the optimum temperature of α-isomaltosyl-transferring enzyme activity was about 50° C., the optimum pH of the enzyme was about 5.5 to 6.0, the thermal stability was up to about 40° C., and the pH stability was in the range of about pH 4.5 to about 9. These physicochemical properties were practically identical to those of the polypeptide having α-isomaltosyl-transferring enzyme activity prepared in Experiment 1. The results described above indicate that recombinant DNA techniques enable to produce polypeptide having the α-isomaltosyl-transferring enzyme activity of the present invention stably and in large scale and at a relatively low cost.

Experiment 7-2

A Transformant, BGN1

A liquid culture medium consisting 5 g/L of "PINE-DEX #4", a partial starch hydrolyzate, 20 g/L of polypeptone, 20 g/L of yeast extract, 1 g/L of sodium phosphate dodeca-hydrate, and water was placed in a 500-ml Erlenmeyer flask in a amount of 100 ml, sterilized by autoclaving at 121° C. for 15 min, and cooled. Then, the liquid medium was sterilely set to pH 7.0, and sterilely admixed with 10 mg of ampicillin sodium salt. A transformant, BGN1, obtained by the method in Experiment 6-2, was inoculated into the above liquid medium, and cultured at 27° C. and for 48 hours under aeration-agitation conditions. To investigate the location of the polypeptide in the culture, cells and supernatant were separately collected by conventional centrifugation. As described in Experiment 7-1, whole-cell extract, obtained by ultrasonic disruption, and periplasmic extract, obtained by osmotic shock procedure were prepared separately. α-Isomaltosyl-transferring enzyme activities of culture supernatant, whole-cell extract and periplasmic extract were assayed, and those values were expressed in terms of the activities/ml-culture, respectively. The results are shown in Table 8.

TABLE 8

| Sample | α-isomaltosyl-transferring enzyme activity (units/ml-culture) |
| --- | --- |
| Culture supernatant | 0.2 |
| Whole-cell extract | 3.1 |
| Periplasmic extract | 2.9 |

As evident from the results in Table 8, it was revealed that the transformant, E. coli BGN1 produced the polypeptide having α-isomaltosyl-transferring enzyme activity of the present invention intracellularly, and secreted most of it in periplasmic fraction. The enzyme activity was also detected in culture supernatant.

As the first control experiment, E. coli XL2-Blue was cultured with the same conditions in the case of the transformant described above except for the addition of ampicillin, and a supernatant and a cell-extract were prepared from the culture. As the second control experiment, Bacillus globisporus N75, FERM BP-7591, was cultured with the same conditions in the case of the transformant described above except for the addition of ampicillin, and a supernatant and a cell-extract were prepared from the culture. In the first control experiment, the enzyme activity was not detected from either of the culture supernatant and the cell-extract. In the second control experiment, the enzyme activity of the culture supernatant and the cell-extract were about 0.7 units and about 0.1 units, respectively, and the total enzyme activity per one milliliter-culture was about 0.8 units. Compared with the total enzyme activity, 3.3 units/ml-culture, of the transformant BGN1, the enzyme activity was evidently low-level values.

The periplasmic fraction was further purified by salting out, dialysis and successive column chromatographies on "SEPABEADS FP-DA13" gel, "SEPHACRYL HR S-200" gel, and "BUTYL-TOYOPEARL 650M" gel according to the methods described in Experiment 3, and the purified polypeptide was analyzed according to the methods described in Experiment 4. As the results, the molecular weight was about 92,000 to 132,000 daltons by SDS-polyacrylamide gel electrophoresis, the isoelectric point was about 7.3 to 8.3 by polyacrylamide gel isoelectrophoresis, the optimum temperature of α-isomaltosyl-transferring enzyme activity was about 50° C., the optimum pH of the enzyme was about 6.0, the thermal stability was up to about 45° C., and the pH stability was in the range of about pH 4.5 to about 10. These physicochemical properties were practically identical to those of the polypeptide having α-isomaltosyl-transferring enzyme activity prepared in Experiment 3. The results described above indicate that recombinant DNA techniques enable to produce polypeptide having the α-isomaltosyl-transferring enzyme activity of the present invention stably and in large scale and at a relatively low cost.

As described above, a polypeptide having an activity to form a cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end, comprising amino acid sequences of either SEQ ID NO:1 or SEQ ID NO:2, or the amino acid sequences having deletion, replacement or insertion of one or more amino acids of SEQ ID NO:1 or SEQ ID NO:2, is found as one of the product of a long studies by the present inventors, and has unique physicochemical properties in comparison with the enzymes ever known. The present invention intends to create the polypeptide by applying recombinant DNA techniques. The following explain the polypeptide of the present invention, its production processes and its uses in detail with the references of examples.

The polypeptide as referred to in the present invention means the whole polypeptides which have an activity to form a cyclotetrasaccharide from a saccharide with a glucose polymerization degree of 3 or higher and bearing both the α-1,6 glucosidic linkage as a linkage at the non-reducing end and the α-1,4 glucosidic linkage other than the linkage at the non-reducing end, and comprises amino acid sequences of either SEQ ID NO:1 or SEQ ID NO:2, or the amino acid sequences having deletion, replacement or addition of one or more amino acids of SEQ ID NO:1 or SEQ ID NO:2. The polypeptide of the present invention usually comprises a solved amino acid sequence, for example, amino acid sequence of SEQ ID NO:1, SEQ ID NO:2 or homologous amino acid sequences of those. Mutants having the homologous amino acid sequences with SEQ ID NO:1 or SEQ ID NO:2 can be obtained by deleting, replacing or adding one or more, i.e., at least one or two, according to the situation, 1–50, 1–30, or 1–10 amino acids of SEQ ID NO:1 or SEQ ID NO:2 without altering the inherent physicochemical properties of the enzyme practically. Even using the same DNA, the post-translational modification of the polypeptide by extra-/intra-cellular enzymes of host is affected by various conditions such as kinds of host, nutrients or composition of culture media, temperatures or pHs for the cultivation of a transformant having the DNA. In such conditions, it is possible to arise some mutants having deletion or replacement of one or more, i.e., at least one or two, according to the situation, 1–30, 1–20, or 1–10 amino acids of N-terminal region of SEQ ID NO:1 or SEQ ID NO:2, further, or having addition of one or more, i.e., at least one or two, according to the situation, 1–30, 1–20, or 1–10 amino acids to those N-terminus, without altering the inherent activity. It is proper that the polypeptide of the present invention includes these mutants as far as they have desired physicochemical properties.

The polypeptide of the present invention can be obtained by the steps of introducing the DNA of the present invention into appropriate hosts, and collecting from the culture of the transformants obtained. The transformant usable in the present invention is a transformant containing a DNA comprising, for example, nucleotide sequence, from the 5'-terminus, of SEQ ID NO:3, SEQ ID NO:4, that having deletion, replacement or insertion of one or more nucleotides of those, anti-sense nucleotide sequence of those, or that having replacement of one or more nucleotides based on gene-degeneracy without altering the amino acid sequence encoded. The nucleotide sequence having replacement of one or more, i.e., at least one or two, according to the situation, 1–190, 1–60, or 1–30 nucleotides of SEQ ID:3 or SEQ ID NO:4 based on gene-degeneracy without altering the amino acid sequence encoded can be used as the nucleotide sequence described above.

The DNA of the present invention comprises a DNA originated from the nature and that synthesized artificially as far as the DNA has the nucleotide sequences described above. Microorganisms belonging the genus Bacillus, for example, Bacillus globisporus C11 (FERM BP-7144) and Bacillus globisporus N74 (FERM BP-7591) were usable as the natural sources. A gene containing the DNA of the present invention can be obtained from the cells of these microorganisms. Specifically, a gene containing the DNA can be released extracellularly by the steps of inoculating the microorganism into a nutrient medium, culturing about one to three days under aerobic conditions, collecting the cells from the culture, treating the cells with cell-lysis enzymes such as lysozyme and β-glucanase or with ultrasonication. In addition to the methods described above, use of protein-hydrolyzing enzymes such as proteinases, detergents such as sodium dodecyl sulfate and freeze-thaw method are also applicable. The objective DNA can be obtained from the disrupted cells using conventional methods in the art, for example, such as phenol-extraction, alcohol-precipitation, centrifugation and ribonuclease-treatment. To synthesize the DNA artificially, chemical synthesis of the DNA based on the nucleotide sequence of SEQ ID NO:3 or SEQ ID NO:4 is applicable. PCR-method is also applicable to obtain the DNA using a gene containing the DNA as template and appropriate chemically synthetic DNA as a primer. The DNA can be obtained by the steps of inserting the chemically synthetic DNA encoding SEQ ID NO:1 or SEQ ID NO:2 into appropriate autonomously replicable vector, introducing the resultant recombinant DNA into appropriate hosts, culturing the resultant transformant, collecting the cells from the culture, and collecting the recombinant DNA containing the DNA from the cells.

The DNAs are usually introduced into host-cells as the form of recombinant DNAs. Recombinant DNAs are usually constructed by a DNA and an autonomously replicable vector, and can be relatively easily prepared by the conventional recombinant DNA techniques if the DNA is obtained. The vectors, for instance, plasmid vectors such as pBR322, pUC18, Bluescript II SK(+), pUB110, pTZ4, pC194, pHV14, TRp7, YEp7 and pBS7; or phage vectors such as λgt·λc, λgt·λb, ρ11, φ1 and φ105 can be used. To express the DNAs of the present invention in E. coli, pBR322, pUC18, Bluescript II SK(+), λgt·λc and λgt·λb are preferable. To express the DNAs of the present invention in B. subtilis, pUB110, pTZ4, pC194, ρ11, φ1 and φ105 are preferable. Plasmids, pHV14, TRp7, YEp7 and pBS7 are useful in the case of replicating the recombinant DNAs in two or more hosts. In order to insert the DNA into these vectors, conventional method used in the art can be used. Specifically, the DNA is inserted into a vector by the steps of cleaving a gene containing the DNA and autonomously replicable vectors by restriction enzymes and/or ultrasonication and ligating the resulting DNA fragment and the resulting vector fragment. The ligation of the DNA fragment and the vector fragment is easy by using a type II-restriction enzymes, particularly, such as Sau 3AI, Eco RI, Hind III, Ban HI, Sal I, Xba I, Sac I and Pst I, for cleaving genes and vectors. After the annealing of the both, if necessary, the desired recombinant DNA is obtainable by ligating them in vivo or in vitro using a DNA ligase. The recombinant DNA, thus obtained, is unlimitedly replicable by the steps of introducing into appropriate hosts and culturing the resultant transformants.

The recombinant DNA thus obtained can be introduced into appropriate host-microorganisms such as E. coli, B. subtilis, Actinomyces and yeasts. The desired clones can be obtained from the transformants by applying the colony-hybridization method or selecting by the steps of culturing in nutrient media containing saccharides with a glucose polymerization degree of 3 or higher and bearing both the α-1,6 glucosidic linkage residue as a linkage at the non-reducing end and the α-1,4 glucosidic linkage other than the linkage at the non-reducing end, and selecting strains producing cyclotetrasaccharide from the saccharides.

The transformants, thus obtained, produce the polypeptide of the present invention extra/intracellularly when cultured in nutrient media. Conventional liquid media which are supplimented with carbon sources, nitrogen sources and minerals, furthermore, if necessary, with trace-nutrients such as amino acid and vitamins, are usually used as the nutrient media. Examples of carbon sources are saccharides including starch, starch hydrolyzate, glucose, fructose, sucrose, α,α-trehalose, α,β-trehalose and β,β-trehalose. Examples of nitrogen sources are nitrogen-containing inorganic- or organic-substances including ammonia, ammonium salts, urea, nitrate, peptone, yeast extract, defatted soybean, corn-steep liquor and meat extract. Cultures containing the polypeptide are obtainable by the steps of inoculating the transformants into the nutrient media, culturing for about one to six days under aerobic conditions such as aeration and agitation conditions while keeping the temperature and pH, usually, at 20–40° C., and pH 2–10. Although the culture can be used intact for enzyme preparation, the polypeptides of the present invention are usually, if necessary, separated from cells or cell debris and purified before use by filtration or centrifugation after extracting from cells using osmotic shock procedure or detergent-treatment, or disrupting cells by ultrasonication or using cell-lysis enzymes. The polypeptides can be purified by applying the purification procedures for polypeptide commonly used, for example, appropriate combination of one or more procedures such as concentration, salting out, dialysis, precipitation, gel filtration chromatography, ion-exchange chromatography, hydrophobic chromatography, affinity chromatography, gel electrophoresis and isoelectrofocusing.

The polypeptides of the present invention have unique properties of forming a cyclotetrasaccharide from saccharides with a glucose polymerization degree of 3 or higher and bearing both the α-1,6-glucosidic linkage as a linkage at the non-reducing end and the α-1,4 glucosidic linkage other than the linkage at the non-reducing end, and comprising amino acid sequences of SEQ ID NO:1, SEQ ID NO:2 or the amino acid sequences having deletion, replacement or insertion of one or more amino acids of SEQ ID NO:1 or SEQ ID NO:2. Cyclotetrasaccharide produced by the action of the polypeptide of the present invention shows no amino-carbonyl reactivity and less browning and deterioration because of its non-reducibility. The saccharide also has an inclusion ability of volatile substances such as ethyl alcohol and acetic acid because of its cyclic structure. Furthermore, cyclotetrasaccharide has useful features such as mild and low sweetness, which less spoil the inherent tastes of foods by excessive sweetness, low-fermentability and low digestibility good for dietary-fibers.

The following explains the formation of cyclotetrasaccharide. Cyclotetrasaccharide can be obtained by acting the polypeptide of the present invention on the substrates, saccharides with a glucose polymerization degree of 3 or higher and bearing both the α-1,6 glucosidic linkage as a linkage at the non-reducing end and α-1,4 glucosidic linkage other than the linkage at the non-reducing end. The saccharides can be obtained as transfer-products by acting α-glucosidase, dextrindextranase or α-isomaltosylglucosaccharide-forming enzyme which is disclosed in PTC/JP01/06412 by the present inventors on starch, starchy compounds such as amylopectin, amylose and glycogen, or those partial hydrolyzates obtained by using acids and/or amylases. The saccharides can also be obtained by acting β-amylase and pullulanase on pullulan. Examples of these saccharide are one or more saccharides with a glucose polymerization degree of 3 or higher and bearing both the α-1,6 glucosidic linkage as a linkage at the non-reducing end and α-1,4 glucosidic linkage other than the linkage at the non-reducing end such as $6^2$-O-α-glucosylmaltose, $6^3$-O-β-glucosylmaltotriose, $6^4$-O-α-glucosylmaltotetraose and $6^5$-O-α-glucosylmaltopentaose.

In the process for the production of cyclotetrasaccharide, the polypeptide of the present invention can be advantageously added to act in the beginning, course, or end of the formation of the saccharide with a glucose polymerization degree of 3 or higher and bearing both the α-1,6 glucosidic linkage as a linkage at the non-reducing end and the α-1,4 glucosidic linkage other than the linkage at the non-reducing end. Usually, the polypeptide of the present invention is allowed to act on appropriate solutions containing one or more saccharides described above as the substrate with keeping desired temperature and pH until when desired amount of cyclotetrasaccharide is formed. Although the enzymatic reaction proceeds under the substrate concentration of about 0.1% (w/w), one percent or higher substrate concentration (throughout the specification, "%(w/w)" is abbreviated as "%" hereinafter, unless specified otherwise), more preferably, 5–50% is used for an industrial scale production. The temperatures for the enzymatic reaction used in the present invention are those which proceed the enzymatic reaction, i.e., those up to about 60° C., preferably, about 30° C. to about 50° C. The pHs for the enzymatic reaction are usually set to 4.5 to 8, preferably about 5.5 to about 7. Since the amount of the polypeptide of the present invention is closely related to the time for the reaction, those can be appropriately set depending on the enzymatic reaction efficiency. The polypeptide can be advantageously used as an immobilized polypeptide by immobilizing it to appropriate carriers using conventional procedures.

The reaction mixture, obtained from the reaction described above, usually includes cyclotetrasaccharide, glucose, maltodextrins such as maltose, a saccharide having a glucose polymerization degree of 3 or higher and having both the α-1,6 glucosidic linkage as a linkage at the non-reducing end and the α-1,4 glucosidic linkage other than the linkage at the non-reducing end, and can be used intact as cyclotetrasaccharide-containing solution. After allowing the polypeptide of the present invention to act the substrate, if necessary, contaminating oligosaccharides in the solution can be hydrolyzed by one or more enzymes selected from the group comprising α-amylase, β-amylase, glucoamylase, and α-glucosidase. Usually, the sugar solution can be used after further purification. One or more conventional methods, for example, selected from the group of decolorization with activated charcoal, desalting by H— or OH—form ion exchanger resin, and column chromatographies such as ion-exchange column chromatography, activated charcoal column chromatography, and silica gel column chromatography, separation using organic solvents such as alcohol and acetone, membrane separation using adequate separability, fermentation by microorganism capable of utilizing or decomposing the contaminating saccharides without utilizing cyclotetrasaccharide, such as *Lactobacillus, Acetobacter* and yeast, and alkaline-treatment to decompose the remaining reducing sugars can be advantageously used as the purification procedures. Particularly, ion-exchange chromatography is preferably used as an industrial scale production method; column chromatography using strong-acid cation exchange resin as disclosed, for example, in Japanese Patent Kokai Nos. 23,799/83 and 72,598/98. Using the column chromatography, the contaminating saccharide can be removed to advantageously produce cyclotetrasaccharide with an improved content of the objective saccharide or saccharide compositions comprising the same. In this case, any one of fixed-bed, moving bed, semi-moving bed, batch, semi-continuous, and continuous methods can be appropriately used.

The resulting cyclotetrasaccharide or saccharide compositions comprising the same with an improved content are aqueous solutions containing cyclotetrasaccharide, usually 10% or more, d.s.b., preferably 40% or more, d.s.b. Usually, the resulting cyclotetrasaccharide or saccharide compositions comprising the same can be concentrated into syrup products, and optionally they can be further dried into powdery products. To produce cyclotetrasaccharide crystals, usually saccharide solution comprising cyclotetrasaccharide purified as described above, preferably cyclotetrasaccharide solution, having a concentration of about 40% or more, d.s.b., can be used. In the case to produce cyclotetrasaccharide penta- to hexa-hydrate crystals, usually, the saccharide solutions are brought to supersaturated solution, for example, having a concentration of about 40–90%, and are placed in a crystallizer, and then gradually cooled while stirring in the presence of 0.1–20%, d.s.b., of a seed crystal with a temperature keeping super-saturation, preferably, 10–90° C., to produce massecuites containing the crystals. In the case to produce cyclotetrasaccharide mono-hydrate or anhydrous crystals, the super-saturation conditions of higher temperature and higher concentration are used. The methods to collect cyclotetrasaccharide crystals and molasses with such crystals include, for example, conventional methods such as separation, block pulverization, fluidized granulation, and spray drying methods. Cyclotetrasaccharide mono-hydrate and anhydrous crystals can be produced by dehydrating and drying cyclotetrasaccharide penta- to hexahydrate crystals. The resulting cyclotetrasaccharide crystal or high cyclotetrasaccharide content powder is non-reducing or less reducing white powder having delicate and mild low-sweetness, and is stable saccharide having high tolerance to acid and thermal stability. The powder is almost free of browning, smelling and deterioration of materials even when mixed or processed therewith: the materials are particularly, for example, amino acid-containing substances such as amino acids, oligopeptides, and proteins. Furthermore, the powder has low hygroscopicity and is capable of preventing adhesion and solidification of powdery substances.

Since cyclotetrasaccharide has inclusion ability, it effectively inhibits the dispersion and quality deterioration of flavorful components and effective ingredients. Therefore, cyclotetrasaccharide can be advantageously used as flavor-retaining agent and stabilizer. For such a purpose, if necessary, the combination use of cyclotetrasaccharide and other cyclic sacchride(s) such as cyclodextrins, branched cyclodextrins, cyclodextrans and cyclofructans can be advantageously used to improve the stabilizing effects.

Since cyclotetrasaccharide is not hydrolyzed by amylase and α-glucosidase, it is substantially free of assimilation by the body when orally administered. Also, the saccharide is not substantially assimilated by intestinal bacteria, and therefore it can be used as an extremely-low caloric water-soluble dietary fiber. In other words, although cyclotetrasaccharide has a weight and volume to give a feeling of fullness, it is not substantially assimilated when orally administered. Therefore, it can be advantageously used as low-caloric food material and dietary food material. Cyclotetrasaccharide can be also used as a sweetener substantially free from causing dental caries because it is scarcely assimilated by dental caries-inducing bacteria.

Cyclotetrasaccharide per se is a natural sweetener with a good acid-tolerance, alkaline-tolerance and thermal stability but with no toxicity and harm. Because of these, in the case of crystalline product, it can be advantageously used for tablets and sugar-coated tablets in combination with binders such as pullulan, hydroxyethyl starch, and polyvinylpyrrolidone. Furthermore, cyclotetrasaccharide has properties of osmosis-controlling ability, filler-imparting ability, gloss-imparting ability, moisture-retaining ability, viscosity, syneresis-preventing ability, solidification-preventing ability, flavor-retaining ability, stability, crystallization-preventing ability for other sugars, insubstantial fermentability, starch retrogradation-preventing ability, protein denaturation-preventing ability, lipid deterioration-preventing ability, etc.

Thus, cyclotetrasaccharide and the saccharide compositions comprising the same can be used intact as a sweetener, low-fermentable food material, low-digestive food material, low-cariogenic food material, low-caloric food material, taste-improving agent, flavor-improving agent, quality-improving agent, preventive of syneresis, preventive of solidification, flavor-retaining agent, preventive of starch retrogradation, preventive of protein denaturation, preventive of lipid deterioration, stabilizer, excipient, inclusion agent, base of pulverization, etc. If necessary, the combination use of cyclotetrasaccharide and conventional materials can be advantageously used as various compositions, for example, food products, tobacco, cigarette, feeds, pet foods, cosmetics, and pharmaceuticals. seasoning, color-imparting agent, flavor-imparting agent, reinforcing agent, emulsifying agent, preventive of oxidation, preventive of ultraviolet rays, and efficacy components of medicine can be appropriately used as the conventional materials.

Cyclotetrasaccharide and the saccharide compositions comprising the same can be used intact as sweeteners. If necessary, they can be advantageously used in combination with other sweeteners, for example, powdery syrup, glucose, fructose, isomerized sugar, sucrosd, maltose, α,α-trehalose, α,β-trehalose, β,β-trehalose, honey, maple sugar, erythritol, xylitol, sorbitol, maltitol, deihydrochalcone, stevioside, α-glycosyl stevioside, sweetener of *Momordica grosvenori*, glycyrrhizin, thaumatin, L-aspartyl L-phenylalanine methyl ester, saccharine, acesulfame K, sucralose, glycine and alanine; and fillers such as dextrin, starch, and lactose. Particularly, cyclotetrasaccharide and the saccharide compositions comprising the same can be suitably used as a low caloric sweetener, dietary sweetener, or the like in combination with one or more low-caloric sweeteners such as erythritol, xylitol, and maltitol; and/or one or more sweeteners with a relatively-high sweetening power such as α-glycosyl stevioside, thaumatin, L-aspartyl L-phenylalanine methyl ester, saccharine, acesulfame K, and sucralose.

Powdery and/or crystalline products of cyclotetrasaccharide and the saccharide compositions comprising the same can be arbitrarily used intact or, if necessary, after mixing with fillers, excipients, binders, etc., and them formed into products with different shapes such as granules, spheres, sticks, plates, cubes, and tablets.

Cyclotetrasaccharide and the saccharide compositions comprising the same well harmonize with other tastable materials having sour-, salty-, bitter-, astringent-, delicious, and bitter-taste; and have a high acid- and heat-tolerance. Thus, they can be favorably used as sweeteners, taste-improving agent, flavor-improving agent, quality-improving agent, etc., to sweeten and/or improve the taste, flavor, and quality of food products in general, for example, a soy sauce, powdered soy sauce, miso, "funmatsu-miso" (a powdered miso), "moromi" (a refined sake), "hishlo"(a refined soy sauce), "furikake" (a seasoned fish meal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, cyclotetrasaccharide and the saccharide compositions comprising the same can be arbitrarily used to sweeten and improve the taste, flavor, and quality of "wagashi" (Japanese cakes) such as "senbei" (a rice cracker), "arare" (a rice cake cube), "okoshi" (a millet and rice cake), "gyuhi" (a starch paste), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of urchin), "ika-no-shiokara" (salted guts of squid), "su-konbu" (processed tangle), "saki-surume" (dried squid strips), "fugu-no-mirin-boshi" (a dried mirin-seasoned shellfish), seasoned fish flour such as of Pacific cod, sea bream, shrimp, etc.; "tsukudani" (foods boiled down in soy sauce) such as those of laver, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, fruit liquor, and sake; soft drinks such as a coffee, cocoa, juice, carbonated beverage, sour milk beverage, and beverage containing a lactic acid bacterium; instant food products such as instant pudding mix, instant hot cake mix, instant juice, instant coffee, "sokuseki-shiruko" (an instant mix of azuki-bean soup with rice cake), and instant soup mix; and other foods and beverages such as solid foods for babies, foods for therapy, drinks, beverage containing amino acids, peptide foods, and frozen foods.

Cyclotetrasaccharide and the saccharide compositions comprising the same can be arbitrarily used to improve the taste preference or to reduce the calorie of feeds and pet foods for animals and pets such as domestic animals, poultry, honey bees, silk worms, and fish; and also they can be arbitrarily used as a sweetener and taste-improving agent, taste-curing agent, quality-improving agent, and stabilizer in other products in a paste or liquid form such as tobacco, cigarette, tooth paste, lipstick, rouge, lip cream, internal liquid medicine, tablet, troche, cod-liver oil in the form of drop, oral refrigerant, cachou, gargle, cosmetic and pharmaceutical. When used as a quality-improving agent or stabilizer, cyclotetrasaccharide and the saccharide compositions comprising the same can be arbitrarily used in biologically active substances susceptible to lose their effective ingredients and activities, as well as in health foods, cosmetics, and pharmaceuticals containing the biologically active substances. Example of such biologically active substances are liquid preparations containing cytokines such as α-, β-, and γ-interferons, tumor necrosis factor-α (TNF-α), tumor necrosis factor-β (TNF-β), macropharge migration inhibitory factor, colony-stimulating factor, transfer factor, and interleukin 2; liquid preparations containing hormones such as insulin, growth hormone, prolactin, erythropoietin, and follicle-stimulating hormone; biological preparations such as BCG vaccine, Japanese encephalitis vaccine, measles vaccine, live polio vaccine, small pox vaccine, tetanus toxoid, Trimeresurus antitoxin, and human immunoglobulin; antibiotics such as penicillin, erythromycin, chloramphenicol, tetracycline, streptmycin, and kanamycin sulfate; vitamins such as thiamin, ribofravin, L-ascorbic acid, cod liver oil, carotenoide, ergosterol, tocopherol; solution of enzymes such as lipase, esterase, urokinase, protease, β-amylase, isoamylase, glucanase, and lactase; extracts such as ginseng extract, turtle extract, chlorella extract, aloe extract, bamboo-leaf extract, peach-leaf extract, loquat-leaf extract, citron-peel extract, and propolis extract; biologically active substances such as living microorganisms paste of virus, lactic acid bacteria, and yeast, and royal jelly. By using cyclotetrasaccharide and the saccharide compositions comprising the same, the above biologically active substances can be arbitrary prepared in health foods, cosmetics, and pharmaceuticals in a liquid, paste, or solid form, which have a satisfactorily-high stability and quality with less fear of losing or inactivating their effective ingredients and activities.

The methods for incorporating cyclotetrasaccharide or the saccharide composition comprising the same into the aforesaid compositions are those which can incorporate cyclotetrasaccharide and the saccharide compositions into a variety of compositions before completion of their processing, and which can be appropriately selected from the following conventional methods; mixting, kneading, dissolving, melting, soaking, penetrating, dispersing, applying, coating, spraying, injecting, crystallizing, and solidifying. In order to exercise the various characteristics of cyclotetrasaccharide, particularly, inclusion ability, taste-improving ability, and flavor-improving ability, the amount of cyclotetrasaccharide or the saccharide compositions comprising the same to be preferably incorporated into the final compositions is usually in an amount of 0.1% or more, desirably, 1% or more.

The following examples explain in detail the production processes for the polypeptide of the present invention, cyclotetrasaccharide obtainable thereby, and saccharides comprising the same:

EXAMPLE 1

Production of a Polypeptide

A liquid medium containing 5 g/L of "PINE-DEX #4", a partial starch hydrolyzate, 20 g/L of polypeptone, 20 g/L of yeast extract, 1 g/L of sodium phosphate, and water was placed in a 500-ml Erlenmeyer flask in an amount of 100 ml, sterilized at 121° C. for 15 min, and cooled. Then, the liquid medium was sterilely set to pH 7.0, and admixed with ampicillin sodium salt to give a final concentration of 100 μg/ml. A transformant, BGC1, obtained by the method in Experiment 5-2, was inoculated into the above liquid medium, and cultured at 27° C. and at 230 rpm for 24 hours to obtain the seed culture. Subsequently, about 18 L of a fresh preparation of the same liquid culture medium as used above seed culture was placed in a 30-L fermentor, sterilized with the same manner, cooled to 27° C., and then admixed with ampicillin to give a concentration of 50 μg/ml, and inoculated with 1%(v/v) of the seed culture, followed by culturing at 27° C. for 48 hours under aeration-agitation conditions. After disrupting cells in the culture by ultrasonication and removing the cell-debris by centrifugation, the activity of the polypeptide of the present invention in the resulting supernatant was assayed. The supernatant had about 3,100 units/L of α-isomaltosyl-transferring enzyme activity. About 74 ml of enzyme solution containing about 135 units/ml of the polypeptide of the present invention, having α-isomaltosyl-transferring enzyme activity, whose specific activity is about 30 units/mg-protein, was obtained by purifying the supernatant according to the method described in Experiment 1.

EXAMPLE 2

Production of a Polypeptide

According to the method described in Example 1, BGN1, a transformant obtained in Experiment 6-2, was seed-cultured, and then main-cultured using a 30-L fermentor. After disrupting cells in the culture by ultrasonication and removing the cell-debris by centrifugation, the activity of the polypeptide of the present invention in the resulting supernatant was assayed. The supernatant had about 3,000 units/L of α-isomaltosyl-transferring enzyme activity. About 150 ml of enzyme solution containing about 72 units/ml of the polypeptide of the present invention, having α-isomaltosyl-transferring enzyme activity, whose specific activity is about 30 units/mg-protein, was obtained by purifying the supernatant according to the method described in Experiment 3.

EXAMPLE 3

Production of a Powdery Product Containing Cyclotetrasaccharide

To an aqueous solution containing 10% panose, commercialized by Hayashibara Biochemical Laboratories Inc., set at pH 6.0 and 35° C., enzyme polypeptide obtained by the method described in Example 1 was added to give a concentration 2 units/g-panose and incubated for 36 hours. The reaction mixture was heated to 95° C. and kept for 10 minute, and then cooled and filtered to obtain a filtrate. According to the conventional manner, the resulting filtrate was decolored with activated charcoal, desalted and purified with ion exchangers in H- and OH- forms, and then concentrated and dried into a powdery products containing cyclotetrasaccharide in a yield of about 91%, d.s.b.

Since the product contains, on a dry solid basis, 34.0% glucose, 2.1% isomaltose, 2.3% panose, 45.0% cyclotetrasaccharide, 4.8% isomaltosylpanose, 1.8% isomaltosylpanoside, and 10.0% of other saccharides and has a mild sweetness, an adequate viscosity, moisture-retaining ability, and inclusion ability, it can be advantageously used in a variety of compositions such as food products, cosmetics, and pharmaceuticals as a sweetener, taste-improving agent, quality-improving agent, syneresis-preventing agent, stabilizer, excipient, inclusion agent, and base of pulverization.

EXAMPLE 4

Production of a Syrupy Composition Containing Cyclotetrasaccharide

"SUNMALT®", a powdery maltose commercialized by Hayashibara Co., Ltd., was dissolved into water to give a concentration of 30% and admixed with 0.08%, d.s.b., of "TRANSGLUCOSIDASE L AMANO™", an α-glucosidase commercialized by Amano Pharmaceutical Co., Ltd., and then set to pH 5.5, followed by the enzymatic reaction at 55° C. for 18 hours. After stopping the reaction by heating, the reaction mixture was set to pH 6.0 and 35° C., and admixed 2 units/g-dry solid basis of enzyme polypeptide obtained in Example 1, and then incubated for 36 hours. The reaction mixture was heated to 95° C. and kept for 10 minute, and then cooled and filtered to obtain a filtrate. According to the conventional manner, the resulting filtrate was decolored with activated charcoal, desalted and purified with ion exchangers in H— and OH— forms, and then concentrated into a 70% syrup in a yield of about 92%, d.s.b.

Since the product contains, on a dry solid basis, 32.5% glucose, 15.7% maltose, 9.8% isomaltose, 4.0% maltotriose, 0.3% panose, 1.6% isomaltotriose, 17.5% cyclotetrasaccharide, 1.2% isomaltosylpanose, 0.7% isomaltosylpanoside, and 16.7% of other saccharides and has a mild sweetness, an adequate viscosity, moisture-retaining ability, and inclusion ability, it can be advantageously used in a variety of compositions such as food products, cosmetics, and pharmaceuticals as a sweetener, taste-improving agent, quality-improving. agent, syneresis-preventing agent, stabilizer, excipient, inclusion agent, and base of pulverization.

EXAMPLE 5

Production of a Crystalline Powder of Cyclotetrasaccharide

A potato starch was prepared into a 15% starch suspension, admixed with calcium carbonate to give a final concentration of 0.1%, adjusted to pH 6.0, and admixed with 0.2%/g-starch of "THERMAMYL 60 L", an α-amylase commercialized by Novo Industries A/S, Copenhagen, Denmark, and then heated at 95° C. for 15 min. After autoclaving at 2 kg/cm2 for 30 min, the reaction mixture was cooled to 35° C., admixed with 7.5 units/g-starch of the polypeptide of the present invention, obtained in Example 1, 2 units/g-starch of α-isomaltosylglucosaccharide-forming enzyme obtained by the method in Experiment 1-3, and 10 units/g-starch of cyclomaltodextrin glucanotransferase commercialized by Hayashibara Biochemical Laboratories Inc., followed by the enzymatic reaction for 48 hours. After heating to 95° C. for 30 min, the reaction mixture was adjusted at 5%, pH 5.0, and 45° C., admixed with 1,500 units/g-starch of "TRANSGLUCOSIDASE L AMANO™", an α-glucosidase and 75 units/g-starch of "GLUCOZYME", a glucoamylase preparation commercialized by Nagase Biochemicals, Ltd, Kyoto, Japan, and then enzymatically reacted for 24 hours. The reaction mixture was heated to 95° C. and kept for 10 minute, and then cooled and filtered to obtain a filtrate. According to the conventional manner, the resulting filtrate was decolored with activated charcoal, desalted and purified with ion exchangers in H— and OH— forms, and then concentrated into a 60% syrup. The resulting syrup contained, on a dry solid basis, 27.5% glucose, 65.1% cyclotetrasaccharide, and 7.5% of other saccharides. The resulting saccharide solution was subjected to a column chromatography using "AMBERLITE CR-1310 (Na-form)", a strong acid cation-exchanger resin commercialized by Japan Organo Co., Ltd., Tokyo, Japan. The resin was packed into four jacketed stainless steel columns having a diameter of 5.4 cm, which were then cascaded in series to give a total gel bed depth of 20 m. Under the conditions of keeping the inner column temperature at 60° C., the saccharide solution was fed to the columns in a volume of 5%(v/v) and fractionated by feeding to the columns hot water heated to 60° C. at an SV (space velocity) of 0.13 to obtain high cyclotetrasaccharide content fractions while monitoring the saccharide composition of eluate by HPLC, and then collected the high cyclotetrasaccharide content fractions. The high cyclotetrasaccharide content solution was obtained in a yield of about 21%, d.s.b. The solution contained about 98%, d.s.b. of cyclotetrasaccharide.

The solution was concentrated to give a concentration of about 70% and then placed in a crystallizer, admixed with about 2% crystalline cyclotetrasaccharide penta- or hexahydrate as seed crystal, and gradually cooled to obtain a massecuite with a crystallinity of about 45%. The massecuite was sprayed from a nozzle equipped on top of drying tower at high pressure of 150 kg/cm$^2$. Simultaneously, hot air heated to 85° C. was drawn down from the upper part of the drying tower, and the resulting crystal powder was collected on a transporting wire conveyor provided on the basement of the tower and gradually moved out of the tower while blowing thereunto a hot air heated to 45° C. The resulting crystalline powder was injected to an ageing tower and aged for 10 hours while a hot air was being blown to the contents to complete crystallization and drying to obtain a crystalline powder of cyclotetrasaccharide penta- or hexahydrate.

Since the product has a relatively low reducibility, does substantially neither cause the amino-carbonyl reaction nor exhibit hygroscopicity, and has a satisfactory handleability, mild low sweetness, adequate viscosity, moisture-retaining ability, inclusion ability, and substantially non-digestibility, it can be advantageously used in a variety of compositions such as food products, cosmetics, and pharmaceuticals as a sweetener, low calorie food, taste-improving agent, flavor-improving agent, quality-improving agent, syneresis-preventing agent, stabilizer, excipient, inclusion agent, and base of pulverization.

EXAMPLE 6

Production of a Crystalline Powder of Cyclotetrasaccharide

A corn starch was prepared into a 28% starch suspension, admixed with calcium carbonate to give a concentration of 0.1%, adjusted to pH 6.5, and admixed with 0. 3%/g-starch of "THERMAMYL 60 L", an α-amylase commercialized by Novo Industries A/S, Copenhagen, Denmark, and then heated at 95° C. for 15 min. After autoclaving at 2 kg/cm$^2$ for 30 min, the reaction mixture was cooled to 50° C., admixed with 6 units/g-starch of the polypeptide of the present invention, obtained in Example 2, 1.8 units/g-starch of α-isomaltosylglucosaccharide-forming enzyme obtained by the method in Experiment 3-3, and one units/g-starch of cyclomaltodextrin glucanotransferase commercialized by Hayashibara Biochemical Laboratories Inc., followed by the enzymatic reaction for 72 hours. After heating to 95° C. for 30 min, the reaction mixture was adjusted to pH 5.0, and 50° C., admixed with 300 units/g-starch of "TRANSGLUCOSIDASE L AMANO™", an α-glucosidase, reacted for 24 hours, and then admixed with 10 units/g-d.s.b., of "GLUCOZYME", a glucoamylase preparation commercialized by Nagase Biochemicals, Ltd, Kyoto, Japan, and 20 units/g- d.s.b., of "NEO-SPITASE PK2", an α-amylase preparation, and then reacted for 17 hours. The reaction mixture was heated to 95° C. and kept for 30 minute, and then cooled and filtered to obtain a filtrate. According to the conventional manner, the resulting filtrate was decolored with activated charcoal, desalted and purified with ion exchangers in H— and OH— forms, and then concentrated into a 60% syrup. The resulting syrup contained, on a dry solid basis, 35.1% glucose, 51.1% cyclotetrasaccharide, and 13.8% of other saccharides. The resulting saccharide solution was fractionated by a column chromatography using a strong acid cation-exchanger resin described in Example 5, and then collected the high cyclotetrasaccharide content fractions in a yield of about 39%, d.s.b. The solution contained about 80%, d.s.b., of cyclotetrasaccharide.

The solution was continuously crystallized while concentrating. The resulting massecuite was separated by a basket-type centrifuge to obtain crystals which were then sprayed with a small amount of water to obtain a high purity cyclotetrasaccharide, penta- or hexa-hydrate, in a yield of about 23%, d.s.b.

Since the product has a relatively low reducibility, does substantially neither cause the amino-carbonyl reaction nor exhibit higroscopicity, and has a satisfactory handleability, mild low sweetness, adequate viscosity, moisture-retaining ability, inclusion ability, and substantially non-digestibility, it can be advantageously used in a variety of compositions such as food products, cosmetics, and pharmaceuticals as a sweetener, low calorie food, taste-improving agent, flavor-improving agent, quality-improving agent, syneresis-preventing agent, stabilizer, excipient, inclusion agent, and base of pulverization.

INDUSTRIAL APPLICABILITY

As described above, the present invention is an invention providing a novel polypeptide which have α-isomaltosyl transferring activity, and its process and uses. The polypeptide of the present invention can be stably provided in large amount and at a relatively low cost by recombinant DNA techniques. Therefore, According to the present invention, a cyclotetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→}, saccharide mixture comprising the same, and a variety of compositions comprising the same can be stably produced in an industrial scale and at a relatively low cost. Since the cyclotetrasacchride has are latively low reducibility, does substantially neither cause the amino-carbonyl reaction nor exhibit higroscopicity, and has a satisfactory handleability, mild low sweetness, adequate viscosity, moisture-retaining ability, inclusion ability, and substantially non-digestibility, it can be advantageously used in a variety of compositions such as food products, cosmetics, and pharmaceuticals as a sweetener, low calorie food, taste-improving agent, flavor-improving agent, quality-improving agent, syneresis-preventing agent, stabilizer, excipient, inclusion agent, and base of pulverization.

The present invention, having these outstanding functions and effects, is a significantly important invention that greatly contributes to this art.

The invention claimed is:

1. An isolated DNA, which encodes a polypeptide comprising the amino acid sequence of SEQ ID NO:2; wherein the polypeptide has an enzymatic activity of producing, through α-isomaltosyl-transferring reaction, a saccharide having a structure of cyclo{ 6)-α-D-glucopyranosyl-(1 3)-α-D-glucopyranosyl-(1 6)-α-D-glucopyranosyl-(1 3)-α-D-glucopyranosyl-(1 } from a saccharide having a glucose polymerization degree of 3 or higher and having both α-1,6 glucosidic linkage as a linkage at the non-reducing end and α-1,4 glucosidic linkage other than the linkage at the non-reducing end, represented by the chemical formula 1:

$$6''\text{-}O\text{-}\alpha\text{-glucosyl-Gn} \qquad \text{Chemical formula 1}$$

(wherein "Gn" means an α-1,4-glucan having a glucose polymerization degree of "n", and "n" means an integer of 2 or greater.).

2. The isolated DNA of claim 1, which comprises the nucleotide sequence of SEQ ID NO:4; or the nucleotide sequence having replacement of one or more nucleotides of SEQ ID NO:4 without changing the amino acid sequence of SEQ ID NO:2 based on genetic code degeneracy, or fully complementary nucleotide sequences thereof.

3. The isolated DNA of claim 1, which originates from a microorganism of the genus *Bacillus*.

4. A replicable recombinant DNA, which comprises the DNA of claim 1 and an autonomously replicable vector.

5. The replicable recombinant DNA of claim 4, wherein said autonomously-replicable vector is a plasmid vector, Bluescript II SK(+).

6. An isolated transformed cell, which is constructed by introducing the recombinant DNA of claim 4 into an appropriate host-microorganism selected from the group consisting of *Escherichia coli, Bacillus subtilis, Actinomyces* and yeasts.

7. The tranaformant isolated transformed cell of claim 6, wherein said host is *Escherichia coli*.

8. A process for producing a polypeptide comprising the amino acid sequence of SEQ ID NO: 2 comprising the steps of culturing the isolated transformed cell of claim 6 and collecting the polypeptide from the resulting cell culture.

9. The process of claim 8, wherein the polypeptide is collected by one or more techniques selected from the group consisting of centrifugation, filtration, concentration, salting out, dialysis, concentration, separatory precipitation, ion-exchange chromatography, gel filtration chromatography, hydrophobic chromatography, affinity chromatography, gel electrophoresis, and isoelectric focusing.

* * * * *